United States Patent
Kinet

(10) Patent No.: US 6,171,803 B1
(45) Date of Patent: Jan. 9, 2001

(54) ISOLATION, CHARACTERIZATION, AND USE OF THE HUMAN β SUBUNIT OF THE HIGH AFFINITY RECEPTOR FOR IMMUNOGLOBULIN E

(75) Inventor: Jean Pierre Kinet, Bethesda, MD (US)

(73) Assignee: The United States Government as represented by the Department of Health and Human Services, Washington, DC (US)

( * ) Notice: Under 35 U.S.C. 154(b), the term of this patent shall be extended for 0 days.

(21) Appl. No.: 09/103,663

(22) Filed: Jun. 23, 1998

Related U.S. Application Data

(62) Division of application No. 07/869,933, filed on Apr. 16, 1992, now Pat. No. 5,770,396.

(51) Int. Cl.$^7$ .................................................. G01N 33/53

(52) U.S. Cl. ........................... 435/7.1; 435/7.2; 436/501

(58) Field of Search ....................... 435/7.1, 7.2; 436/501

(56) References Cited

U.S. PATENT DOCUMENTS

| | | |
|---|---|---|
| 4,171,299 | 10/1979 | Hamburger . |
| 4,477,446 | 10/1984 | Jones et al. . |
| 4,620,948 | 11/1986 | Builder et al. . |
| 4,940,782 | 7/1990 | Rup et al. . |
| 4,946,788 | 8/1990 | Delespesse . |
| 4,962,035 | 10/1990 | Leder et al. . |
| 5,091,313 | 2/1992 | Chang . |
| 5,770,396 | 6/1998 | Kinet . |

FOREIGN PATENT DOCUMENTS

| | | |
|---|---|---|
| 0 286 700 A1 | 10/1988 | (EP) . |
| 0 321 601 A1 | 6/1989 | (EP) . |
| 90/04640 | 5/1990 | (WO) . |
| 93/21317 | 10/1993 | (WO) . |

OTHER PUBLICATIONS

Adamczewski et al., Evidence for Two Distinct Kinase/Phosphatase Pathways in the Activation of Receptors Coupled to Non–Receptor–Kinases: The High Affinity IgE Receptor as a Model, *J. Biol. Chem.* 267:18126–18132 (1992).
Alber, Gottfried, Structure–Function Relationships in the Mast Cell High Affinity Receptor for IgE, *J. Biol. Chem.* 266:22613–22620 (1991).
Alcaraz et al., Phase Separation of the Receptor for Immunoglobulin E and Its Subunits in Triton X–114, *J. Biol. Chem.* 259:14922–14927 (1984).
Alcaraz et al., Further Characterization of the Subunits of the Receptor with High Affinity for Immunolgobulin E, *Biochemistry* 26:2569–2575 (1987).
Baranes, D., and Razin, E., Protein Kinase C Regulates Proliferation of Mast Cells and the Expression of the mRNAs of fos and jun Proto–oncogenes During Activation by IgE–Ag or Calcium Ionophor A23187, *Blood* 78:2354–2364 (1991).
Basciano et al., Monoclonal Antibodies that Inhibit IgE Binding, *J. Biol. Chem.* 261:11823–11831 (1986).
Benhamou et al., Tyrosine Phosphorylation Coupled to IgE Receptor–Mediated Signal Transduction and Histamine Release, *PNAS USA* 87:5327–5330 (1990).
Benhamou et al., Protein–Tyrosine Kinase p72$^{eyk}$ in High Affinity IgE Receptor Signaling, *J. Biol. Chem.* 268:23318–23324 (1993).
Bieber et al., Human Epidermal Langerhans Cells Express the High Affinity Receptor for Immunoglobulin E (FcεRI), *J. Exp. Med.* 175:1285–1290 (1992).
Blank et al., Complete Structure and Expression in Transfected Cells of High Affinity IgE Receptor, *Nature* 337:187–189 (1989).
Blank et al., Characterization of Truncated α Chain Products from Human, Rat, and Mouse High Affinity Receptor for Immunoglobulin E, *J. Biol. Chem.*. 266:2639–2646 (1991).
Burton et al., T Cell Receptor Variable Gene Expression: Analysis in Ragweed–Sensitive Patients During Allergen Exposure, *Int. Arch. Allergy Appl. Imunol.* 306–310 (1990).
Fong et al., Distinct Forms of the β Subunit of the GTP–Binding Regulatory Proteins Identified by Molecular Cloning, *PNAS USA* 84:3792–3796 (1987).
Goetze et al., Enzymatic Cleavage Products of the α Subunit of the Receptor for Immunoglobulin E, *Biochemistry* 20:6341–6349 (1981).
Hakimi et al., The α Subunit of the Human IgE Receptor (FcεRI) is Sufficient for High Affinity IgE Binding, *J. Biol. Chem.* 265:22079–22081 (1990).
Hewick et al., A Gas–Liquid Solid Phase Peptide and Protein Sequenator, *J. Biol. Chem.* 256:7990–7997 (1981).
Hill, M.R., and Cookson, W.O.C.M., A New Variant of the β Subunit of the High–Affinity Receptor for Immunoglobulin E (FcεRI–β E237G): Associations with Measures of Atopy and Bronchial Hyper–Responsiveness, *Human Molecular Genetics* 5:959–962 (1996).
Hill et al., FcεRI–β Polymorphism and Risk of Atopy in a General Population Sample, *British Medical Journal* 331:776–779 (1995).

(List continued on next page.)

Primary Examiner—John Ulm
(74) *Attorney, Agent, or Firm*—Klarquist Sparkman Campbell Leigh & Whinston, LLP

(57) ABSTRACT

The present invention relates to nucleic acid sequences, encoding amino acid sequences of the α, β, and γ subunits of the high affinity receptor for immunoglobulin E, and for amino acid sequences of the subunits. The invention further relates to a method of producing the receptor by expressing cDNA for its α, β, and γ subunits in a host cell simultaneously. Aspects of the invention are methods and compositions to inhibit the function of the human beta subunit, thereby treating or preventing allergic reactions.

4 Claims, 52 Drawing Sheets

OTHER PUBLICATIONS

Howard et al., CD3 ζ Subunit can Substitute for the γ Subunit of Fc_ε Receptor Type I in Assembly and Functional Expression of the High–Affinity IgE Receptor: Evidence for Interreceptor Complementation, *PNAS USA* 87:7015–7019 (1990).

Hutchcroft et al., FcεRI–Mediated Tyrosine Phosphorylation and Activation of the 72–kDa Protein–Tyrosine Kinase, PTK72, In RBL–2H3 Rat Tumor Mast Cells, *PNAS USA* 89:9107–9111 (1992).

Jacobs et al., Isolation and Characterization of Genomic and cDNA Clones of Human Erythropoietin, *Nature* 313:806–810 (1985).

Kannellopoulos et al., Composition and Subunit Structure of the Cell Receptor for Immunoglobulin E, *J. Biol. Chem.* 255:9060–9066 (1980).

Kinet et al., Dissociation of the Receptor for Immunoglobulin E in Mild Detergents, *Biochemistry* 24:4117–4124 (1985).

Kinet et al., Noncovalently and Covalently Bound Lipid on the Receptor for Immunoglobulin E, *Biochemistry* 24:7342–7348 (1985).

Kinet et al., A cDNA Presumptively Coding for the α Subunit of the Receptor with High Affinity for Immunoglobulin E, *Biochemistry* 26:4605–4610 (1987).

Kinet et al., Isolation of cDNA Clones Coding for the α Subunit of the Receptor with High Affinity for IgE, (Abstract No. 6006) *Fed. Proc.* 46 (1987).

Kinet et al., Isolation and Characterization of cDNAs Coding for the β Subunit of the High Affinity Receptor for Immunoglobulin E, *PNAS USA* 85:6483–6487 (1988).

Kishi, K., A New Leukemia Cell Line with Philadelphia Chromosome Characterized as Basophil Precursors, *Leukemia Research* 9:381–390 (1985).

Kochan et al., Isolation of Gene Coding for the Alpha Subunit of the Human High Affinity IgE Receptor, *Nucleic Acids Research* 16:3584 (1988).

Kurosaki et al., The βSubunit of the FcεRI is Associated with the FcγRIII on Mast Cells, *J. Exp. Med.* 75:447–451 (1992).

Küster et al., Characterization and Expression of the Gene for the Human Fc Receptor γ Subunit, *J. Biol. Chem.* 265:6448–6452 (1990).

Küster H., The Gene and cDNA for the Human High Affinity Immunoglobulin E Receptor Beta Chain and Expression of the Complete Human Receptor, *J. Biol. Chem.* 267 (1992).

Le Coniat et al., The Human Genes for the α and γ Subunits of the Mast Cell Receptor for Immunoglobulin E are located on Human Chromosome Band 1q23, *Immunogenetics* 32:183–186 (1990).

Letourneur et al., Characterization of the Family of Dimers Associated with Vc Receptors (FcεRI and FcγRIII), *The Journal of Immunology* 147:2652–2656 (1991).

Letourneur et al., T–cell and Basophil Activation Through the Cytoplasmic Tail of T–Cell–Receptor ζ Family Proteins, *Immunology* 88:8905–8909 (1991).

Li et al., FcεRI–Mediated Tyrosine Phosphorylation of Multiple Proteins, Including Phospholipase Cγ1 and the Receptor $\beta\gamma_2$ Complex, in RBL–2H3 Rat Basophilic Leukemia Cells, *Molecular and Cellular Biology* 12:3176–3182 (1992).

Lui et al., Identification of an IgE–binding Protein by Molecular Cloning, *PNAS USA* 82:4100–4104 (1985).

Maekawa et al., Determination of the Sequence Coding for the Beta Subunit of the Human High–Affinity IgE Receptor, *FEBS Letters* 302:161–165 (1992).

Maekawa et al., Determination of the Sequence Coding for the Beta Subunit of the Human High–Affinity IgE Receptor, DDBJ Database Entry Hsigerb, Accession No. D10583; Feb. 25, 1992.

Metzger et al., Analysis of the Structure and Function of the Receptor for Immunoglobulin E, *Molecular Immunology* 21:1167–1173 (1984).

Metzger et al., The Receptor with High Affinity for Immunoglobulin E, *Ann. Rev. Immunol.* 4:419–470 (1986).

Metzger et al., Emerging Picture of the Receptor with High Affinity for IgE, *Int. Arch. Allergy Appl. Immunol.* 14–17 (1989).

Metzger et al., The Receptor with High Affinity fir IgE, *Ciba Foundation Symposium* 147:93–113 (1989).

Miller et al., Cloning and Characterization of Complementary DNA for Human Tryptase, *J. Clin. Invest.* 84:118–1195 (1988).

Miller et al., Expression of High–Affinity Binding of Human Immunoglobulin E by Transfected Cells, *Science* 244:334–337 (1989).

Nilson et al., Enhancement of IgE Synthesis in the Human Myeloma Cell Line U–266 with an IgE Binding Factor from a Human T–Cell Line, *Scand. J. Immunol.* 34:721–726 (1991).

Paolini et al., Phosphorylation/Dephosphorylation of High–Affinity IgE Receptors: A Mechanism for Coupling/Uncoupling a Large Signaling Complex, *PNAS USA* 89:10733–10737 (1992).

Ra et al., Complete Structure of the Mouse Mast Cell Receptor for IgE (FcεRI) and Surface Expression of Chimeric Receptors (Rat–Mouse–Human) on Transfected Cells, *J. Biol. Chem.* 264:15323–15327 (1989).

Ra et al., A Macrophage Fcγ Receptor and the Mast Cell Receptor for IgE Share an Identical Subunit, *Nature* 341:752–754 (1989).

Ravetch et al., Structural Heterogeneity and Functional Domains of Murine Immunoglobulin G Fc Receptors, *Science* 234:718–725 (1986).

Samelson, L.E., and Klausner, R.D., Tyrosine Kinases and Tryosine–Based Activation Motifs, *J. Biol. Chem.* 267:24913–24916 (1992).

Sasada et al., Secretion of Human EGF and IgE in Mammalian Cells by Recombinant DNA Techniques; Use of a IL–2 Leader Sequence, *Cell Structure and Function* 13:129–141 (1988).

Shimizu et al., Human and Rat Mast Cell High Affinity Immunoglobulin E Receptors: Characterization of Putative α–chain Gene Products, *PNAS USA* 85:1907–1911 (1988).

Sofer, G. and Britton, V.J., Designing an Optimal Chromatographic Purification Scheme for Proteins, *Bio Techniques* Nov./Dec.:198–203 (1983).

Stryer, L. (Ed.), "The Genetic Code," in: *Biochemistry*, $2^{nd}$ Edition, Chapter 26, W.H. Freeman and Company, San Francisco (1981).

Suggs et al., Use of Synthetic Oligonucleotides as Hybridization Probes: Isolation of Cloned cDNA Sequences for Human $\beta_2$–Microglobulin, *PNAS USA* 78:6613–6617 (1981).

Tepler et al., The Gene for the Rat Mast Cell High Affinity IgE Receptor α Chain, *J. Biol. Chem.* 264:5912–5915 (1989).

Varin–Blank et al., Surface Expression of Mutated Subunits of the High Affinity Mast Cell Receptor for IgE, *J. Biol. Chem.* 265:15685–15694 (1990).

Wang et al., Epidermal Langerhans Cells From Normal Human Skin Bind Monomeric IgE via FcεRI, *J. Exp. Med.* 175:1353–1365 (1992).

Weiss A., T Cell Antigen Receptor Signal Transduction: A Tale of Tails and Cytoplasmic Protein–Tyrosine Kinases, *Cell* 73:209–212 (1993).

Yamamoto et al., Similarity of Protein Encoded by the Human c–erb–B–2 Gene to Epidermal Growth Factor Receptor, *Nature* 319:230–234 (1986).

Young, R.A. and Davis R.W., Yeast RNA Polymerase II Genes: Isolation with Antibody Probes, *Science* 222:778–782 (1983).-

FIG. 1A

```
TACTAAGAGT CTCCAGCATC CTCCACCTGT CTACCACCGA GCATGGGCCT ATATTGAAG                60

CCTTAGATCT CTCCAGCACA GTAAGCACCA GGAGTCCATG AAGAAG ATG GCT CCT               115
                                                    Met Ala Pro
                                                     1

GCC ATG GAA TCC CCT ACT CTA CTG TGT GTA GCC TTA CTG TTC TTC GCT              163
Ala Met Glu Ser Pro Thr Leu Leu Cys Val Ala Leu Leu Phe Phe Ala
 5                  10                  15

CCA GAT GGC GTG TTA GCA GTC CCT CAG AAA CCT AAG GTC TCC TTG AAC              211
Pro Asp Gly Val Leu Ala Val Pro Gln Lys Pro Lys Val Ser Leu Asn
20                  25                  30                  35

CCT CCA TGG AAT AGA ATA TTT AAA GGA GAG AAT GTG ACT CTT ACA TGT              259
Pro Pro Trp Asn Arg Ile Phe Lys Gly Glu Asn Val Thr Leu Thr Cys
        40                  45                  50

AAT GGG AAC AAT TTC TTT GAA GTC AGT TCC ACC AAA TGG TTC CAC AAT              307
Asn Gly Asn Asn Phe Phe Glu Val Ser Ser Thr Lys Trp Phe His Asn
            55                  60                  65

GGC AGC CTT TCA GAA GAG ACA AAT TCA AGT TTG AAT ATT GTG AAT GCC              355
Gly Ser Leu Ser Glu Glu Thr Asn Ser Ser Leu Asn Ile Val Asn Ala
70                  75                  80
```

FIG. 1B

```
AAA TTT GAA GAC AGT GGA GAA TAC AAA TGT CAG CAC CAA CAA GTT AAT    403
Lys Phe Glu Asp Ser Gly Glu Tyr Lys Cys Gln His Gln Gln Val Asn
 85                  90                  95

GAG AGT GAA CCT GTG TAC CTG GAA GTC TTC AGT GAC TGG CTG CTC CTT    451
Glu Ser Glu Pro Val Tyr Leu Glu Val Phe Ser Asp Trp Leu Leu Leu
100                 105                 110                 115

CAG GCC TCT GCT GAG GTG ATG GTG ATG GAG GGC CAG CCC CTC TTC AGG    499
Gln Ala Ser Ala Glu Val Met Val Met Glu Gly Gln Pro Leu Phe Arg
                120                 125                 130

TGC CAT GGT TGG AGG AAC TGG GAT GTG TAC AAG GTG ATC TAT TAT AAG    547
Cys His Gly Trp Arg Asn Trp Asp Val Tyr Lys Val Ile Tyr Tyr Lys
        135                 140                 145

GAT GGT GAA GCT CTC AAG TAC TGG TAT GAG AAC CAC AAC ATC TCC ATT    595
Asp Gly Glu Ala Leu Lys Tyr Trp Tyr Glu Asn His Asn Ile Ser Ile
150                 155                 160

ACA AAT GCC ACA GTT GAA GAC AGT GGA ACC TAC TAC TGT ACG GGC AAA    643
Thr Asn Ala Thr Val Glu Asp Ser Gly Thr Tyr Tyr Cys Thr Gly Lys
165                 170                 175

GTG TGG CAG CTG GAC TAT GAG TCT GAG CCC CTC AAC ATT ACT GTA ATA    691
Val Trp Gln Leu Asp Tyr Glu Ser Glu Pro Leu Asn Ile Thr Val Ile
180                 185                 190                 195
```

FIG. 1C

```
AAA GCT CCG CGT GAG AAG TAC TGG CTA CAA TTT TTT ATC CCA TTG TTG    739
Lys Ala Pro Arg Glu Lys Tyr Trp Leu Gln Phe Phe Ile Pro Leu Leu
            200                     205                     210

GTG GTG ATT CTG TTT GCT GTG GAC ACA GGA TTA TTT ATC TCA ACT CAG    787
Val Val Ile Leu Phe Ala Val Asp Thr Gly Leu Phe Ile Ser Thr Gln
            215                     220                     225

CAG CAG GTC ACA TTT CTC TTG AAG ATT AAG AGA ACC AGG AAA GGC TTC    835
Gln Gln Val Thr Phe Leu Leu Lys Ile Lys Arg Thr Arg Lys Gly Phe
            230                     235                     240

AGA CTT CTG AAC CCA CAT CCT AAG CCA AAC CCC AAA AAC AAC TGATATAATT 887
Arg Leu Leu Asn Pro His Pro Lys Pro Asn Pro Lys Asn Asn
            245                     250                 255

ACTCAAGAAA TATTTGCAAC ATTAGTTTTT TTCCAGCATC AGCAATTGCT ACTCAATTGT    947

CAAACACAGC TTGCAATATA CATAGAAACG TCTGTGCTCA AGGATTATA GAAATGCTTC   1007

ATTAAACTGA GTGAAACTGG TTAAGTGGCA TGTAATAGTA AGTGCTCAAT TAACATTGGT  1067

TGAATAAATG AGAGAATGAA TAGATTCATT TATTAGCATT GTAAAAGAGA TGTTCAATTT  1127

CAATAAAATA AATATAAAAC CATGTAAAAA AAAAAAAAAA AAAAAAA               1174
```

```
ACGTTTCTGT GTAACAATAT CTTTTATTCC TGGATAGTCC AATTA ATG AAA AAA   54
                                              Met Lys Lys
                                              -3

ATG GAC ACA GAA AAT AAG AGC AGA GCA GAT CTT GCT CTC CCA AAC CCA  102
Met Asp Thr Glu Asn Lys Ser Arg Ala Asp Leu Ala Leu Pro Asn Pro
 1               5                  10                  15

CAA GAA TCC CCC AGC GCA CCT GAC ATT GAA CTC TTG GAA GCG TCC CCT  150
Gln Glu Ser Pro Ser Ala Pro Asp Ile Glu Leu Leu Glu Ala Ser Pro
            20                  25                  30

CCT GCA AAA GCT CTA CCA GAG AAG CCA GCC TCA CCC CCA CCA CAG CAG  198
Pro Ala Lys Ala Leu Pro Glu Lys Pro Ala Ser Pro Pro Pro Gln Gln
            35                  40                  45
```

FIG. 6B

```
ACA TGG CAG TCA TTT TTG AAG AAA GAG TTG GAG TTC CTG GGC GTA ACC        246
Thr Trp Gln Ser Phe Leu Lys Lys Glu Leu Glu Phe Leu Gly Val Thr
         50                  55                  60

CAA GTT CTG GTT GGT TTG ATA TGC CTT TGT TTT GGA ACA GTT GTC TGC        294
Gln Val Leu Val Gly Leu Ile Cys Leu Cys Phe Gly Thr Val Val Cys
 65                  70                  75                  80

TCC ACA CTC CAG ACT TCA GAC GAC TTT GAC GAC GAA GTG CTT TTA TAT        342
Ser Thr Leu Gln Thr Ser Asp Asp Phe Asp Asp Glu Val Leu Leu Tyr
             85                  90                  95

AGA GCA GGC TAC CCA TTC TGG GGT GCA GTG CTG ▶TTT GTT TTG TCT GGA       390
Arg Ala Gly Tyr Pro Phe Trp Gly Ala Val Leu Phe Val Leu Ser Gly
                100                 105                 110

TTT TTG TCA ATT ATG TCC GAA AGG AAA AAC ACA CTG TAT CTG GTG AGA        438
Phe Leu Ser Ile Met Ser Glu Arg Lys Asn Thr Leu Tyr Leu Val Arg
         115                 120                 125

GGC AGC CTG GGA GCA AAC ATT GTC AGC ATC GCT GCA GGC TTG GGG            486
Gly Ser Leu Gly Ala Asn Ile Val Ser Ile Ala Ala Gly Leu Gly
             130                 135                 140

ATC GCC ATA TTG CTC ATT CTC AAT CTG AGC AAC AAC TCC GCT TAT ATG AAC    534
Ile Ala Ile Leu Leu Ile Leu Asn Leu Ser Asn Asn Ser Ala Tyr Met Asn
 145                 150                 155                 160
```

FIG. 6C

```
TAC TGC AAG GAT ATA ACC GAA GAC GAT GGT TGC TTC GTG ACT TCT TTC     582
Tyr Cys Lys Asp Ile Thr Glu Asp Asp Gly Cys Phe Val Thr Ser Phe
                165                     170                 175

ATC ACA GAA CTG GTG TTG ATG TTG CTG TTT CTC ACC ATC CTG GCC TTT     630
Ile Thr Glu Leu Val Leu Met Leu Leu Phe Leu Thr Ile Leu Ala Phe
            180                     185                 190

TGC AGT GCC GTG CTG CTC ATT ATC TAT AGG ATT GGA CAA GAA TTT GAG     678
Cys Ser Ala Val Leu Leu Ile Ile Tyr Arg Ile Gly Gln Glu Phe Glu
        195                     200                 205

CGT AGT AAG GTC CCC GAT GAC CGT CTC TAT GAA GAA TTA CAT GTG TAT     726
Arg Ser Lys Val Pro Asp Asp Arg<Leu Tyr Glu Glu Leu His Val Tyr
    210                     215                 220

TCA CCA ATT TAC AGT GCG TTG GAA GAC ACA AGG GAA GCG TCC GCA CCA     774
Ser Pro Ile Tyr Ser Ala Leu Glu Asp Thr Arg>Glu Ala Ser Ala Pro
225                     230                     235             240

GTG GTT TCA TAAGAATCAA GGGGCCAGGA CAATCTGATT CCAGTCTAGT            823
Val Val Ser>
```

FIG. 6D

```
CTTGAGAGTC GATCTTTTTG CAACATTATG GCAACATTTC TGTTTCCTCC GCACTCTATC    883
AACTTTTCAA TTGGATTGTT CTGTAGATAC CCCTGTTTCA GTTATGATGC CTCTGGTCTT    943
TAATTATCTC CCTTTTTGTG GATATCGTTC AATCCAGTTT TCTTGTTTTG TGTCACAGTC   1003
TCACATACAA CCTTTCTGGA AAGTCATCAA AAACAAGCTA GCTTTTATTG CATGTCTACT   1063
TTCATGAACA AAAGGAAGGA GGAGTTATTT TGAGAGTTTA ACTAAACTTA GATAATCAGG   1123
TAATATTTGA CTCTTAGTTC ATTTAGAAT TCTCAACAAT ACTTGTGCAT GATATATGCC   1183
CACCATATCA AGCCTTCTAT ATATATTTAA TATGGTATTT ACTTTTCTAT GTAGATAGAT   1243
TTTCCACCCT CAATAATAAT GGGTTTTTCA GAGACATAAA GCTTTATGAA AAGACACATA   1303
```

FIG. 6E

```
TTATCTAATT CATGGGTATA TTCACTAATA CAGTTGTTGC TCAGTGGTGT TTACTACTTG  1363
GTGGGTAGTA GGTAATAGAG AACATTATTA AATCATTCAG TGTAGTGAGA TGCATAGGTA  1423
AAATCAGGGA CACTGTGAGT GTGTATATCT TTTGGTAAGA CATGTGTGAA AATGAAGAAT  1483
AAACTGATGA AGACTTGAGC TGGAAAGTAG TCAATGGGAA TGACAAGAAA TGATTGTGTA  1543
TAACACTTGT AGATAAATAA CTACCAACAA TTGGTAGAGA TTGCCATGTA TGCCTAAAAT  1603
CTCCCAGCCC AAGGCCAGCC TCTGTTACAC AGTGAGTTAG AGGCCAGTCT GGGCTACACA  1663
AGATCATACA TCAAAGGACG AAAGAAGATG TTGGTTCAAA CTGTTAACAC AGTAAGGAT  1723
ATTTAAACAA ACAGAAGTTT GACTGATATA TTGAGTGCTT GAGTTTTTAA TAAAACTGAA  1783
TGAATAACAT TGCGGGGGAG GGGAGCCAGTG ATGCAGAAGT CTGGATGATG GAGGAGTAGC  1843
AGAATCAGAT GAAACATTGA AACGTATTTC CAGACTTTTG TTCTGAGATG GTTATAAGAG  1903
```

FIG. 6F

```
CAATCACCAT TAAATGAAGA AGGTCAAGAC ACCAAAAGAA TTATTTTGAG ATAGAATTAA    1963
GACAGTCAAA ATCCACATGC CTATACTTAG AAGGTGAAGT AAGGATCAAA AGTAGAAAGC    2023
CTAACGATTA GTTGGAAAAG CATATTACGT TAGGCAGCAG ATGTCTATAG TGGAGAAAAG    2083
TTAAACAAGG AGAAATAATG AACCACCAGA GACTCTACAT GTTGGTTTGG GAAATAAGAG    2143
AAAATAGCAA TTCTAAACGA ATGCAAACTC TGAAGAAGCA TTTCCCAAAG GGTGTGGGCA    2203
GAGGACCAGA ACATTTGCAA ATGTACCTAG AGAGCAAACC TGAATAGGAG GTAAAATGGG    2263
GGAAAAGCAG CTAAGAAAAT GATTTTGTTG CTGTTATTTA GATTTTAAAA GAAACAAAAA    2323
GAGTCATTAA AAATCTGTTT GCTGGGATCA GTTATTGTGT TCTCTGTGTA TGTCCAAAGT    2383
ACAGGTAACT TTTCTAAATC TTCCTGTAAG GCTCACCCTCA TATGTCTCTT CACATAGCCA    2443
CACCCTTGAT TCACAGTTAC TCTACCACAG TAGTAAACTG TGCTTGTGGT CTCCCTTATG    2503
TATCTTCACT AGTGTTTATA AAATAAATCA GAATTATTTA AA                       2545
```

FIG. 6G

```
GTG AGA ACA TAT CTG TAATTGTTTC TGAAATGATG CTAACCAGAG ATTTTATTTT      55
Val Arg Thr Tyr Leu
 1               5

AATCAAAGAC AACTAATTTT CTTTTAATCA AGTGCTTATC TCTAGCCTTT CAATAATATC   115

TACAGTTCTT CATTATATG CACATAGCCA TCTATAAATG TAGTTTCCAA AGCACTCTCT   175

ACATATACTC ATTAACAAGA GCAAATACAC TCACCACAGT TAACTATGGT TTAACCCATT   235

ACTATACTTT TATTGACTGA AAACCTTGAG ACTGTACAAA AAAAAAAAA A            286
```

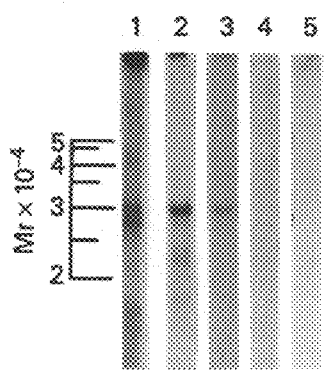 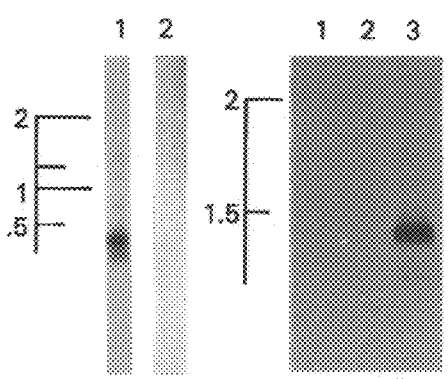 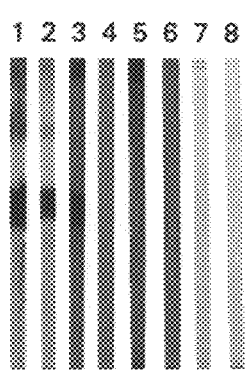
FIG. 7A  FIG. 7B  FIG. 7C  FIG. 7D

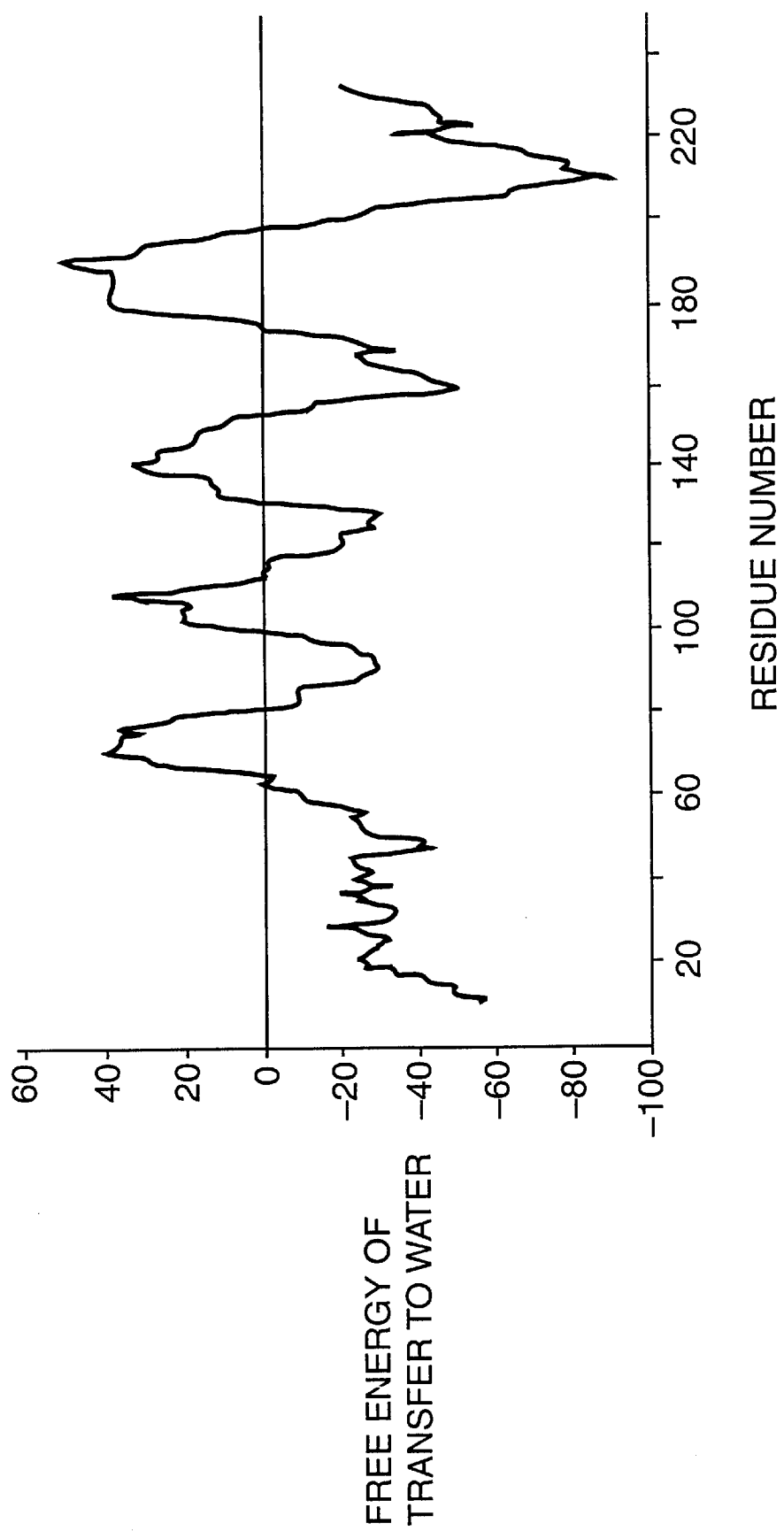

FIG. 9

```
AGCGCTGCAGCCCCCGCCCAGG ATG ATC CCA GCG GTG ATC TTG TTC          46
                        M   I   P   A   V   I   L   F          -11

TTG CTC CTT TTG GTG GAA GAA GCA GCT GCC CTA GGA GAG CCG CAG     91
 L   L   L   L   V   E   E   A   A   A   L   G   E   P   Q      5
                                    -1 +1

CTC TGC TAT ATC CTG GAT GCC ATC CTG TTT TTG TAT GGT ATT GTC    136
 L   C   Y   I   L   D   A   I   L   F   L   Y   G   I   V     20

CTT ACC CTG CTC TAC TGT CGA CTC AAG ATC CAG GTC CGA AAG GCA    181
 L   T   L   L   Y   C   R   L   K   (I   Q   V   R)  (K   A    35

GAC ATA GCC AGC CGT GAG AAA TCA GAT GCT GTC TAC ACG GGC CTG    226
 D   I   A   S   R)  (E   K   S   D   A   V   Y)  T   G   L     50

AAC ACC CGG AAC CAG GAG ACA TAT GAG ACT CTG AAA CAT GAG AAA    271
 N   T   R   (N   Q   E   T   Y   E   T   L   K)  H   E   K     65

CCA CCC CAA TAG CTTTACAACACGTGTTCTCAGCTGCATTCCTTTTCCGCTTTTA    326
 P   P   Q   -                                                   68

ATTCTCTCCTCCTGCCCCTCATGATTGACGTGGCTGTGTGCTACCCTCCGTGCTTCTGGAACTAG    385
CTGACCTTATTCCCAGAACCATGCTAGGCTCTAAATCAATGTCCCCATATCCACCAAAG          444
ACTTACTCACTGACATTTCTCTCTCCCATCCTTTGCTTCCTCTCTTCCTTCC                503
CTGATCCTCTGTGCTCACTAAACAATGGGAAGGGATTACCCCCCAATAAAGCTGCCAGA          562
GATCACGCTCAAAAAAAAAAAA                                              586
```

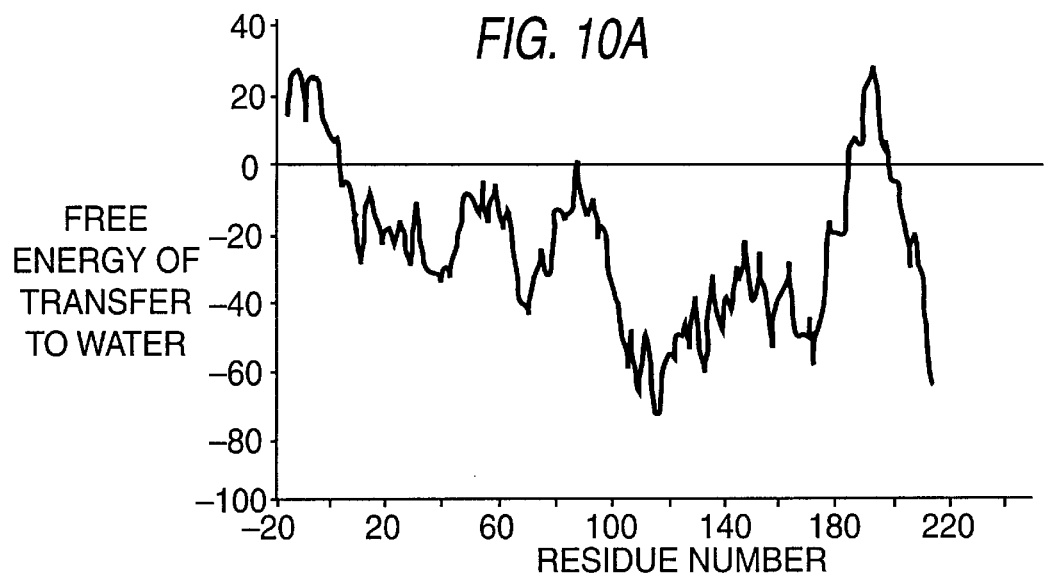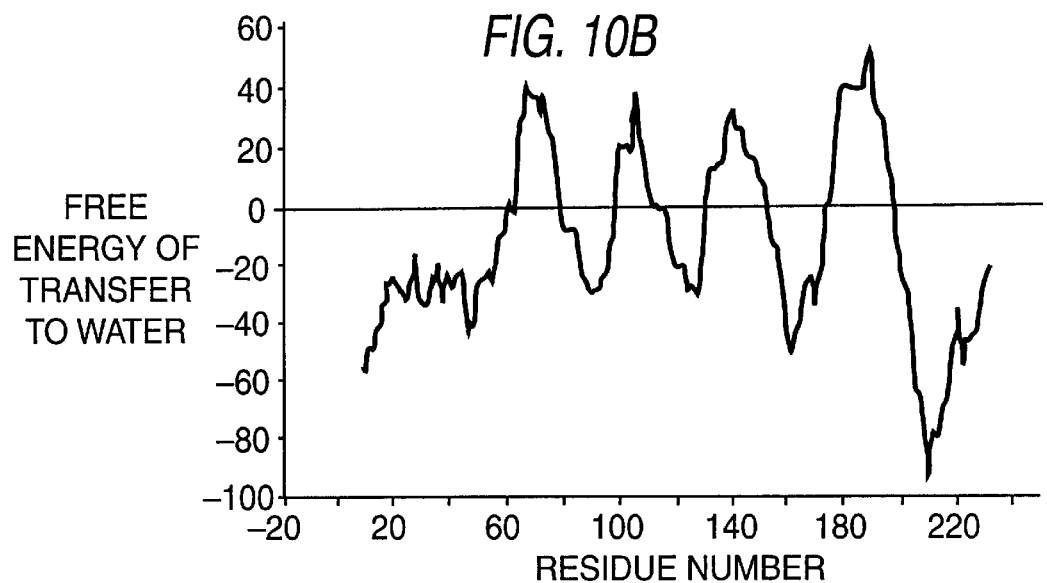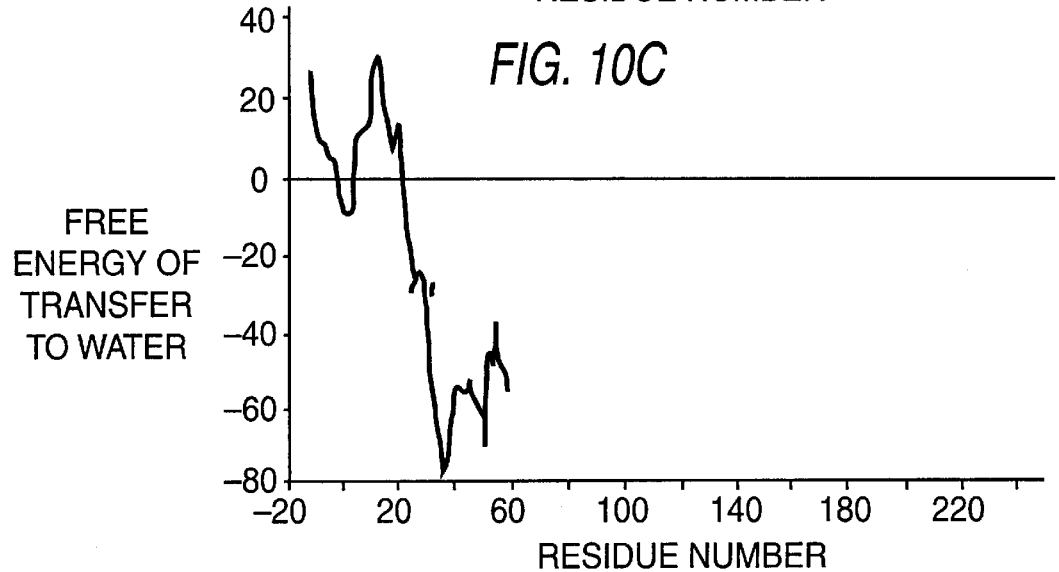

FIG.IIA
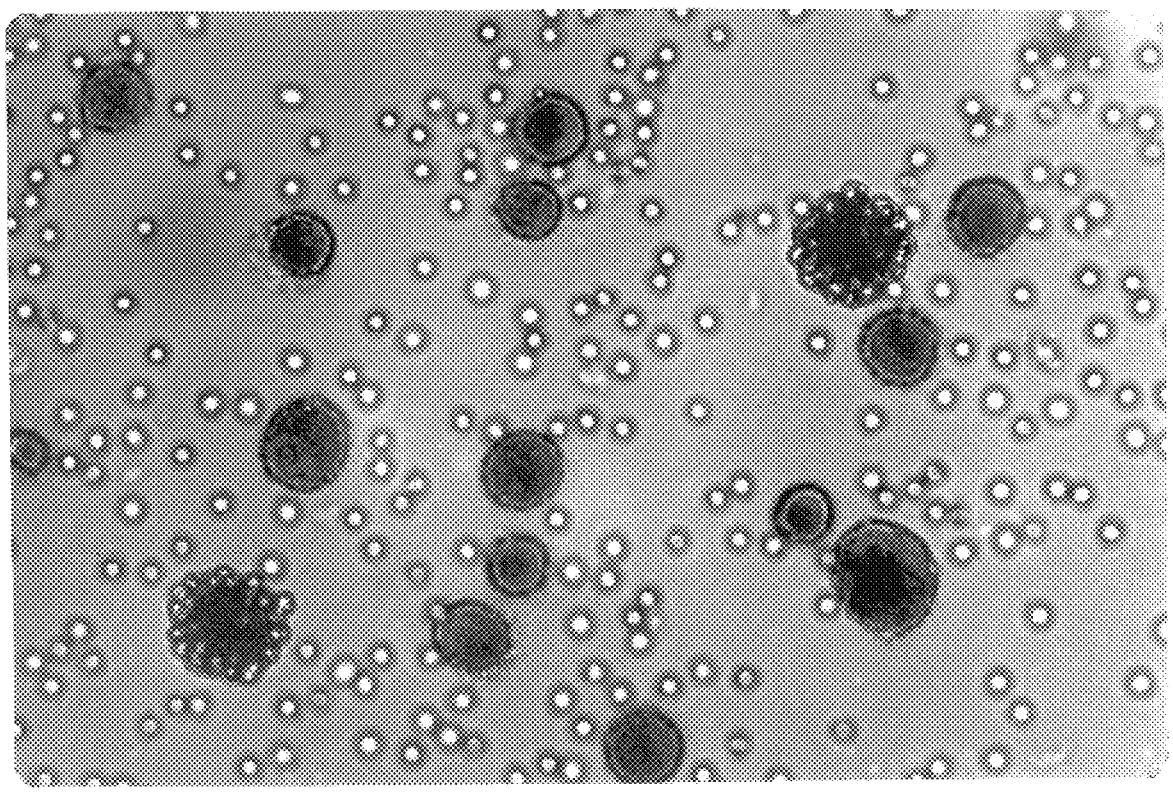

TO FIG. 12B →

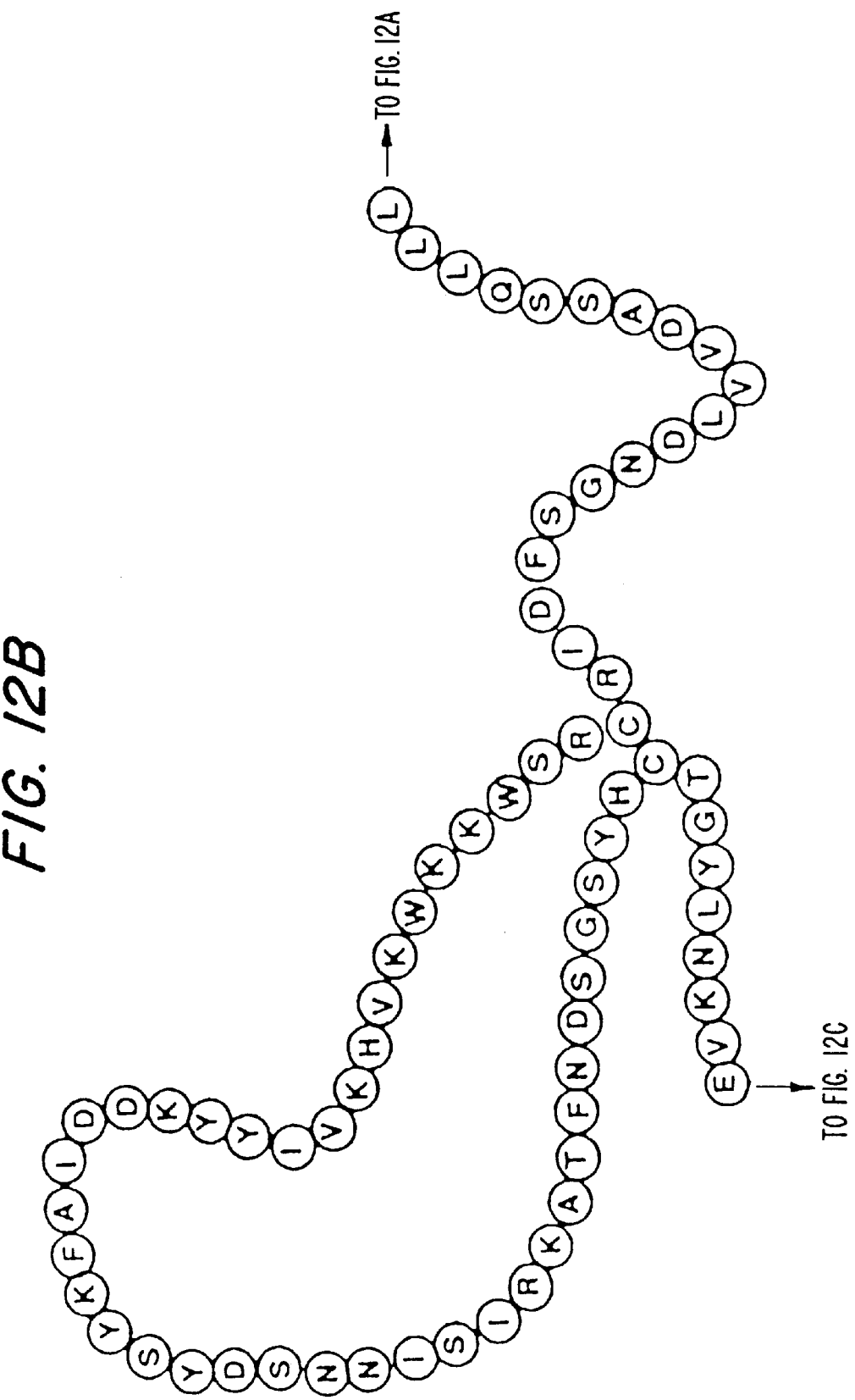

FIG. 14A

```
AAGCTTTTCA AAGGTGCAAT TGGATAACTT CTGCCATGAG AAATGGCTGA ATTGGGACAC    60
AAGTGGGGAC AATTCCAGAA GAAGGGCACA TCTCTTTCTT TTCTGCAGTT CTTTCTCACC   120
TTCTCAACTC CTACTAAAAT GTCTCATTTT CAGGTTCTGT AAATCCTGCT AGTCTCAGGC   180
AAAATTATGC TCCAGGAGTC TCAAATTTTC TTATTTCATA TTAGTCTTTA TTTAGTAGAC   240
TTCTCAATTT TTCTATTCAT CACAAGTAAA AGCCTGTTGA TCTTAATCAG CCAAGAAACT   300
TATCTGTCTG GCAAATGACT TATGTATAAA GAGAATCATC AATGTCATGA GGTAACCCAT   360
TTCAACTGCC TATTCAGAGC ATGCAGTAAG AGGAAATCCA CCAAGTCTCA ATATAATAAT   420
ATTCTTTATT CCTGGACAGC TCGGTTAATG AAAAAATGGA CACAGAAAGT AATAGGAGAG   480
CAAATCTTGC TCTCCCACAG GAGCCTTCCA GGTAGGTACA AGTATTATT TTTTTCTACC   540
```

FIG. 14B

```
CTCAGTCACT TGTGGCAGGG GAAGTCATAG TCACGGTGCT TAGGAGATGA AACTTTATTG    600
ATTTAGGCAT GGATCCATCT AGTTTAATTA ATATATTGGG TATGAGGAAG CTACTTGCTG    660
TACTTTCCAT GTGGTTCTCT CTCCCTGGAG AGGAACATTT TTACTCAGCT TGCAAACTGG    720
AAATAGATTT TCTCACATTA GAAGCTCATT TTCTGGGTAT GAGACAGGAG AGTTCATACT    780
GTGTATGTAG ATCTCTGGCT TCTGGGTCTG ACATGTGCTG AGGGACACAT ATCCTTCACA    840
CATGCTTTTA TAAATACTTG ATAAAGTAAC CTGCTTCTTG ATTGGTCTTT ATAATCCATA    900
AGCTGTGGGA TGCTTCTCTG AAGATGAAAA TAGTAATAGA GTCCCATCTA GCTATTCAAA    960
GCCATTCCTT CATTGTATTC TGTGCACATG AAGTTGGGGT TTGTTACTGA CAAAATATAT   1020
TCAGATACAT TTCTATGTTA AAAGGATTGT GAGATGCATA GGTAAATGTG TTTATTTTCA   1080
GTTTACTTG TCAACATAGA TGAATGAGAA AGAACTTGAA AGTAACACTG GATTAAGAAT   1140
```

FIG. 14C

```
AGGAAAATTT GGCATGGATT TTGCCTCCATT TTGTCCCATC TAATCACTTG GATAGTGTTC    1200
AGGTGTTCTT GGTCAGTTAC TTGGATGCTC TGAGCTTTAG TTTCTTGGTG ATTACAATGA    1260
AGATTTGAAT TACAGGATGG CTTTGAAAAA ATAAACAAAA CTCCCCTTTC TGTCTGTCGA    1320
GAATGTTGCA CAGGGAGTTA CAGAATGTTC TCATGACTGA ATTGCTTTTA AATTTCACAG    1380
TGTGCCTGCA TTTGAAGTCT TGGAAATATC TCCCCAGGAA GTATCTTCAG GCAGACTATT    1440
GAAGTCGGCC TCATCCCCAC CACTGCATAC ATGGCTGACA GTTTTGAAAA AAGAGCAGGA    1500
GTTCCTGGGG GTGAGTGAGC CTCCTCCAAC TTTGACTAGA GTAAGGGTTG GGTCTAGAAA    1560
AGAATATTGA GTTGCATCAA CTGTTTTCCC ACTTGGATTC ATGAGAGGTG TTAGGTCCTT    1620
TAAAAAACAT GGTAGATAAA AAATTGCTAG TAACTGGGTC CTTTTGGGAA GAGCCAGAAG    1680
CATTTCCTCA TAAAGACTTT AAATTGCTAG GACGAGAATG GCCAACAGGA GTGAAGGATT    1740
CATAACTTTA TCTTTACTTA GATGTAAAGA ACAATTACTG ATGTTCAACA TGACTACATA    1800
CATAAAGGCG CATGGAGAAA AGTATTGGCC TTCCATGCAT TAGGTAGTGC TTGTATCAAT    1860
TCTTATAGTG GCTAGGGTAT CCTGGAAAAT CTTACGTGTG GATCATTTCT CAGGACAGTC    1920
TAGGACACTA ACGCAGTTTC TCATGTTTGG CTTCTATTAT TAAAAAATGA TACAATCTCG    1980
```

FIG. 14D

```
GGAAAATTT TTTGATTTTC ATGAAATTCA TGTGTTTTTC TATAGGTAAC ACAAATTCTG      2040
ACTGCTATGA TATGCCTTTG TTTGGAACA GTTGTCTGCT CTGTACTTGA TATTTCACAC      2100
ATTGAGGGAG ACATTTTTC ATCATTAAA GCAGGTTATC CATTCTGGGG AGCCATATTT       2160
GTGAGTATAT ATCTATAATT GTTTCTGAAA TAACACTGAA CATAGGTTTT TCTCTTTCTC     2220
AGATCTAACC AGTTGTTTAT TCCCAGTATT AAGATGATAT TTATAATTCT TAATTATAAA     2280
TATATGTGAG CATATATAAC ATAGATATGC TCATTAACAA CAACAAAAGA TTCTTTTTAC     2340
AATTAACGGT GGGTTAAACA TTTAGCCCAC AGTTTTATCC CATGAGAAAC CTGAATCTAA     2400
TACAAGTTAA ATGACTTGCC TAAGGGCCAC TTGACTAATA ACTATTCATC CTAAACTTTC     2460
AGAATCCAAC TCCAGGAACA TACTTCTAGC ACTATTCATC AATAAAGTTA TATGATAAAT     2520
ACATACAACT TTATCTGTCA ACTAAAAATA ACAACAGAGG CTGGGCATGG TGGCTCACAC     2580
CCGTAATCCC AGCACTTTGG GAGGCTGAGG CAGGTGGATC ACCTGAGGTC AGGAGTTTGA     2640
```

FIG. 14E

| | | | | | |
|---|---|---|---|---|---|
| GACCAGCCTG | ACCAACATGG | TGAAACCTCA | TCTCTACTAA | ATATAAAAAA | TTAGCTGAGT | 2700 |
| GTGATAGTGC | ATACCTGTAA | TCCAGCTACT | TAAGAGGCTG | AGGCAGGAGG | CTTGTTTGAA | 2760 |
| CCTGGAAGGC | AGAGGTTGCA | GTGAGCTGAG | ATTGTGCCAT | TGCACTCCAG | CCTGGGCAAT | 2820 |
| AAGTGCGAAC | TCTGTCTCAA | AATAATAATA | ATAATAAATA | AAAATAAAGT | TGTCTTCATG | 2880 |
| AAAAATGAGG | AAAGAGATTG | CTGGGGTGAG | AAACATTAAG | ATCAATGGGC | ATATGGTGAC | 2940 |
| CTTCTATGCC | CTAGAAACTC | TTTTANGGTA | TTTCTCCCTG | GTATCTCTTT | TACNCATCGT | 3000 |
| TCTATCTGGA | AAAATAGGTG | GATGAGTGAG | ATAATAACGG | TATATACTTT | TTAAAGGTCT | 3060 |
| AATTGACATA | TATAAATTGC | AAGTATTTCA | GATGTCAATT | TGCTAACCTT | GACACACATA | 3120 |
| GACACACATG | AAAACATCAC | CACATTAATA | CAATGTATGT | ATCCATCATT | CCAAAAGCTT | 3180 |
| CCCTGTGTAT | CTTGTTAACT | CTTTCTTCCT | CCCTCCACTC | CTTGTCCCTC | CGTTCCCAAG | 3240 |
| AAAACATTGA | TCTGCTTCCT | GTGAATATAA | ATTAACTTAC | ATTTTTTAGA | GCTTTATATA | 3300 |
| AGTATGTTCT | CTTTACTGTT | TGTCTTCCTT | CGCTGCACAG | TTATTTTGAG | ATTCTTCAAG | 3360 |

FIG. 14F

```
AGTATGTTCT CTTTACTGTT TGTCTTCCTT CGCTGCACAG TTATTTTGAG ATTCTTCAAG    3360
TTTTTCTTT  ATATCGATAC TTCATTCACA AGAATATATT TTAATTCTAG ACTATGTCAC    3420
ATTGACTTTG TCGTCTGCTA AATCCCTAGT GCTCAGATGA CTTGTTCAGG ACTCTCCTTG    3480
AACCTGTACC TCTGTTANAT TGAAACTTGT CTCTACTGTC TTTTTATTTC AAACACAGCT    3540
TATTAGGTGT CTCTCAACCC ATCAAACNCA CAATCTGAGT CTTTAGGAGA TTGCTTTGAA    3600
TTTGTGCTAT TGACTTATAT NTATATNAAA TNTGTAAATG TTTGGTAAAA ATATCATCAT    3660
GTACNTTTTC ATAATTACGC TATNTNCACA TGATATATGT CAGACTCTGG AAATATGCAT    3720
GCCACAGACA CGTGTTTCTT GCCTAAAGGG GCTGATGGAA GACNCACATA CNAATAGACG    3780
ATTGCAGTAG AATGAGAGTG GTGGTCTAAN CAGTACATGT CCTGATGTTG CTCGGACAGT    3840
TACTACNCCA AGAGTACCCC CTGCATTGTC AGGGTTAGCA TCTCCTGGAA GCCTCATGTA    3900
AATGAAGAAT TTCATGCTCC ATCCAGGACC TAATGAATAA GAATCTGCAT TTTAGCAAGA    3960
CCCTCATATG ATTCATATAC ACTTTTTTTT TTTTTTTTA  GATGGAGTCT CACTCTGTC    4020
```

FIG. 14G

| | | | | |
|---|---|---|---|---|
| GCCCAGGCTG | GAGTGCAATG | GCATGATCTT | GGCTCACTGC | AACCCTCTGCC | TCCCGGGTTC | 4080
| AAGTGATTCT | CCTGTCTCAG | CCTCCCTAGT | AGCTGGGACT | ACAGGTGCAT | GCCACAGTGG | 4140
| CTGGCTAATT | TTTGTATTTT | TAGTAGAGAC | AGGGTTTCAC | CATTTTGGTC | AGGCTGGTCT | 4200
| TGAACTCATG | ACCTCCGGTG | ATTCCCCCGC | CTCGGCTTCC | CAAAGTGCTG | GGATTACAGA | 4260
| CATGAGCCAC | CACACCCGCC | TTATTCGTAT | ACNCATTTAA | TTCTGAGAAG | CACTCTATAG | 4320
| AAAATAAGAA | TAAGAAAATA | TTGGGCTCAC | AGGTGACATT | AATAAGTAAC | TTTATCGAGT | 4380
| ACCCCAAATT | TTACCTATGT | TTGGAAGATG | GGGTTAAAAG | GACACATTGA | AAACAAGAAC | 4440
| TCATTGTGGC | TTTTTTTTCC | TCCTTTTTGA | ACAGTTTTCT | ATTTCTGGAA | TGTTGTCAAT | 4500
| TATATCTGAA | AGGAGAAATG | CAACATATCT | GGTGAGTTGC | CCGTTTCTGT | CTTGTCCAT | 4560
| CCTTGAAAAG | ATAAGAAGAA | CAGAGTTTTA | AGAGTCTTAA | GGGAAACACA | TCTTTGTCTC | 4620
| CTATATTACT | TGTGAATGTG | GATATATGAT | TTTGTTTCAA | TCTATTTTGT | GTCCTAAGGC | 4680

FIG. 14H

```
TTTTGCAAC AGAAGTTGGA TATATCATTA GAAACATAAA TTGTACCATT TAACATACAT    4740
GAAGTTTATG TTTACCTTGA CGTCTCTCTA AAAAGTGTCC TACACCGGCA TTGTCCTTGT    4800
AGGCATATTC ACATGATCAA ATAAAATAAT TAGTTTTCAA TTAAGGAGAA TATTTGAGGA    4860
AAGACCGTAC GTGTTCATGT GGTTCCTGAA GGCAGTCCAG TGAGAAAGTA ATATATGCTT    4920
CATTAAACAA TGCGGACATT TTCAGGGTTT CCCTTTTTAA CCAAAATTTG GAAGCAATGT    4980
GGAATTACT GGATGCATCC AGCCCTGAAA TGAAGATAGG TTTATTGAAT GTGCCAGCAA    5040
GTGCAGGCCC AGTCTCGAGT GTTCTTCATT ATTATCAGGT GAGAGGAAGC CTGGGAGCAA    5100
ACACTGCCAG CAGCATAGCT GGGGAACGG GAATTACCAT CCTGATCATC AACCTGAAGA    5160
AGAGCTTGGC CTATATCCAC ATCCACAGTT GCCAGAAATT TTTGAGACC AAGTGCTTTA    5220
TGGCTTCCTT TTCCACTGTA TGTATTTTT TTTGTGTGGG AAGACTAAGA TTCTGGGTCC    5280
TAATGTAAGT AAGAAGCCCT CTTCTCCCTGT TCCATGAACA CCATCCTTTT CTGTAACTTC    5340
```

FIG. 14I

```
TATTACACAG TATAGTGGTT CTGTAAGTTC ACACAGCCCA GGGAGATGCT GGCTGCCCAC   5400
TCCCCTCAAC CCAGGCAAAT TCCTCGGGGT TAAAGTTATC TACTGCAAGT GACGATCTCT   5460
GGGTTTTCT GTGCCTGTGT TTGTGTGTGT GTGTGTGTGT GTATGTGTCA   5520
CTTAAAAGG ACTGGTCAGA TGGTAGGGAG ATGAAAACAG GAGATGCTAT AAGAAAATAA   5580
ACTTTTGGGG CGAATACCAA TGTGACTCTT TTTGTTTGTC ATTTGTTGCT GTTCAATAGG   5640
AAATTGTAGT GATGATGCTG TTTCTCACCA TTCTGGGACT TGGTAGTGCT GTGTCACTCA   5700
CAATCTGTGG AGCTGGGGAA GAACTCAAAG GAAACAAGGT AGATAGAAGC CCGATATAAA   5760
ATCTTGAATG ACAGGTTAAC GAATTGGAGC TTTATTCCTT AAAATATGGC CTGGGTTTTC   5820
TGAAACATTT CTTCCAGAAA ATAGTTTCTC CAAGTTTTAT TACTTTGGTT TACAAATCTC   5880
ACATTAAAT CACATTTTAT ACCATAAGTA GCACACATTT CATAATATTC CTCTGAATGA   5940
GGGTTGGGAT AATAGGACTG ATATGTTAGA AATGCCTTAA AGTGTGTGGA GCATGAGAGA   6000
TGGATGTACA GAAGGCTTGT GAGGAAACCA CCCAGGTATC TGGCCTTGTT TTCTGCCCCA   6060
```

FIG. 14J

```
GAACTAGCCG CCTATTCCTG TTTCTGTTTT ATTCCTTTGT TTCTTGACTT TTCCTTTCCA    6120
ACTTGCTCTA AAACCTCAGT TTTCTTTCCT TTCTGATTCA TGACTACCAA ATGTTTTCAC    6180
TTGCCTCACC CGTCCATTAC ACCTTTGATA AGAACCACCA GACCTTGTGC TCATGTACTT    6240
GCCCATGTCT GATGGAAGAA ACATACTCTC TCCATCTGTC CACTTTCCTG AGGCATTCAA    6300
GTCTAGCCAC CTTTTAAAAT CACTCTCCCTC CAGGCTGGGC ACGGTGTCAC GCCTGTAATC    6360
TCAGCACTTT GTGAGGCTGA GGAGGGCGGA TCACTTGAAG TCAGGAGTTC AAAACCAGCC    6420
TGGCCAAATG GCAAAACCAA ATCTTCTTCA ATTATAACCA AATCTTAAAC CAAATCTCTA    6480
CTAAAAAATA CAACAAAACA AAACAACAAC AACAAAAACA GAAAAGGAAA CATTAGCCCA    6540
GCGTGGTGGC AGGTACCTGA GGTTCCAGAT ACTGGGAGG CTGAAGCAGG AGAATCGCTT    6600
GAGCCCAAGA GATGGAGGTT GCAGTGAGCC GAGATCATGC CACTGCACCA CAGCCAGGGT    6660
GACAGAGCCA TACTTCCCAG CACATTGGGA GGCCAAAGCT GAAGAATAAT TTGAGGTGAG    6720
```

FIG. 14K

```
GATTTGGAGA CCAGCCTGGC CAACATGGTG AAACTCCGTC TGTACTAAAA ATATAAAACT  6780
TAGTGGGGCA TGGGGGCACA CACCTGTAAT TTCAGCTACT TAGGAGGCTG AGGCAGGAGA  6840
ATTGCTTGAA CCCGGGAGGC GGAAGTTGCA GTGAGCCAAG ATCGTGGCCA CTGCACTCCA  6900
GCCTGGGTGA CATAGTGAGA TTCTGTCTCA AAAAAAATAA AAGAAATTTA AAAAATCACT  6960
CTCTTCCAAA GATAGATAAA TAAGACAGCA GATATACTAA GGAATAACCT CACCAACTTG  7020
TCATTGACTG ACATGATTTC TTTTGGCCCA CTTGGCCAGC TAGTCTGTT  TGGTTTTCTG  7080
GAAATGAAAG AAATAATCAG AGTTTAATGA CAGAGAGCGT GAGACCCAGA AAGACAAAAG  7140
TAGATGAGGT AAGTCTCTTG AGCGAGACTT CTAGGGATGG GAAATTGTG  GTGATTGATA  7200
TGAAATGATT TTTCCCTTAT CAGGTTCCAG AGGATCGTGT TTATGAAGAA TTAAACATAT  7260
ATTCAGCTAC TTACAGTGAG TTGGAAGACC CAGGGGAAAT GTCTCCTCCC ATTGATTTAT  7320
AAGAATCACG TGTCCAGAAC ACTCTGATTC ACAGCCAAGG ATCCAGAAGG CCAAGGTTTT  7380
```

FIG. 14L

```
GTTAAGGGGC TACTGGAAAA ATTTCTATTC TCTCCACAGC CTGCTGGTTT TACATTAGAT   7440
TTATTCGCCT GATAAGAATA TTTTGTTTCT GCTGCTTCTG TCCACCTTAA TATGCTCCTT   7500
CTATTTGTAG ATATGATAGA CTCCTATTTT TCTTGTTTTA TATTATGACC ACACACATCT   7560
CTGCTGGAAA GTCAACATGT AGTAAGCAAG ATTTAACTGT TTGATTATAA CTGTGCAAAT   7620
ACAGAAAAAA AGAAGGCTGG CTGAAAGTTG AGTAAAACTT TGACAGTTTG ATAATATTTG   7680
GTTCTTAGGG TTTTTTTTTT TTTTAGCATT CTTAATAGTT ACAGTTGGGC ATGATTTGTA   7740
CCATCCACCC ATACCCACAC AGTCACAGTC ACACACACAT ATGTATTACT TACACTATAT   7800
ATAACTTCCT ATGCAAATAT TTTACCACCA GTCAATAATA CATTTTTGCC AAGACATGAA   7860
GTTTATAAAA GATCTGTATA ATTGCCTGAA TCACCAGCAC ATTCACTGAC ATGATATTAT   7920
TTGCAGATTG ACAAGTAGGA AGTGGGGAAC TTTTATTAAG TTACTCGTTG TCTGGGGAGG   7980
TAAATAGGTT AAAAACAGGG AAATTATAAG TGCAGAGATT AACATTTCAC AAATGTTTAG   8040
TGAAACATTT GTGAAAAAAG AAGACTAAAT TAAGACCTGA GCTGAAATAA AGTGACGTGG   8100
```

FIG. 14M

```
AAATGGAAAT AATGGTTATA TCTAAAACAT GTAGAAAAAG AGTAACTGGT AGATTTTGTT   8160
AACAAATTAA AGAATAAAGT TAGACAAGCA ACTGGTTGAC TAATACATTA AGCGTTTGAG   8220
TCTAAGATGA AAGGAGAACA CTGGTTATGT TGATAGAATG ATAAAAAGGG TCGGGCGCGG   8280
AGGCTCACGC CTGTAATCCC AGCCCTTTGG GAGGCCGAGG TGGGCAGATC ACGAAGTCAG   8340
TAGTTTGAGA CCAGCCTGGC CAACATAGTG AAACCCCGTC TCTACTAAAA ATACAAAAAA   8400
AAAATTAGCT GGGTGTGGTG GCAGTCACCT GTAGTCCCAG CTACTTGGGA GGATGAGGCA   8460
GGAGAATCGC TTGAACCTGG GAGGCGGAGG TTGCAGTGAG CCGAGATCGC ACCAGTGCAC   8520
TCCAGCCTTG GTGACAATGG GAGACTCCAT CTCAAAAAAA AAAAAAAAAA AAAAAGATA   8580
AAAAGTCAGA AATCTGAAAA GTGGAGGAAG AGTACAAATA GACCTAAATT AAGTCTCATT   8640
TTTTGGCTTT GATTTGGGG AGACAAAGGG AAATGCAGCC ATAGAGGGCC TGATGACATC   8700
CAATACATGA GTTCTGGTAA AGATAAAATT TGATACACGG TTTGGTGTCA TTATAAGAGA   8760
```

FIG. 14N

```
AATCATTATT AAATGAAGCA AGTTAACACT CTAAGAGAAT TATTTGAGA TAGAAGTGAA    8820
GCTAAGCTAA ACTTCACATG CCTATAATTG GAGGGAAAAA CTAAGGATAA AATCTAGCCT    8880
AGAAGATACA ATAATTAGTC ATAAACATGC ATTGTGAAAC TGTAGAGAGC AGGTAGCCCA    8940
AAATAGAGAA AGATTAGATA AAGAGAAAAT AAGTATCCAT CAGAGACAGT ATCTCTAGGC    9000
TTGGGCAAGA GAAAAGTCCA CAGTGATAAG CAACTCCACC TAAGGCATGA ATATGCGGCA    9060
GAGAAAACAG CAATAGTGAA TGAATGCAAA AGGTGCTGAG CAAATTCCAC ACATGAGTAT    9120
TGTGCATGAA TAAATGAATA AAACATTTGC AAAGACCTTT AGAGAAAGAG AATGGGAGCA    9180
TATGTGCGAA ATAAGATAGT TGATTATGAA TAGAAGGTAG TAGTTTATGT TGAAGAAAAG    9240
AAAAATTCTG TTTATAAAAG AAGGAAAAGA TAGTTTATGT GAGAGTATTA GTATATAAGAG    9300
TCCTACAGAT GGACTGAAAA AAATCAGTCT GAGAGTATTA GTCACAATTA ATGAAATAAT    9360
TACATTTTAT GTATTGAGGA AAAAGGTGAC AAAAGGTGAC AGTAGATGT TAATTTCCCT    9420
```

FIG. 140

```
AGATTGTGAA AGTGATCACG ACAATCACAC AACAAATAAT TAAGTGACTT GGTATGCTTT    9480
ATTAATTGT AGGGCCTGAG GTTTCCATT CTCATTTTC TAAAATACAA TTTTGTTTCT       9540
CCAAATTTGA CAGCAGAATA AAAACCCTAC CCTTTCACTG TGTATCATGC TAAGCTGCAT    9600
CTCTACTCTT GATCATCTGT AGTATTAAT CACATCACTT CCATGGCATG GATGTTCACA    9660
TACAGACTCT TAACCCTGGT TTACCAGGAC CTCTAGGAGT GGATCCAAATC TATATCTTTA  9720
CAGTTGTATA GTATATGATA TCTCTTTTAT TTCACTCAAT TTATATTTTC ATCATTGACT   9780
ACATATTTCT TATACACAAC ACACAATTTA TGAATTTTTT CTCAAGATCA TTCTGAGAGT   9840
TGCCCCACCC TACCTGCCTT CCCACCCTCAG AATTGTCTTT GCAGACACAG AGCACAATGC  9900
TGGGGTTCTC TTCACACTAT CACTGCCCCA AATTGTCTTT CTAAATTCA ACTTCAATGT    9960
CATCTTCTCC ATGAAGACCA CTGAATGAAC ACCTTTTCAT CCAGCCTTAA TTTCTTGCTC  10020
CATAACTACT CTATCCCACG ATGCAGTATT GTATCATTAA TTATTAGTGT GCTTGTGACC  10080
TCCTTATGTA TTCTCAATTA CCTGTATTTG TGCAATAAAT TGGAATAAATG TAACTTGATT 10140
```

FIG. 14P

```
TCTTATCTGT GTTTGTGTTG GCATGCAAGA TTTAGGTACT TATCAAGATA ATGGGGAATT   10200
AAGGCATCAA TAAAATGATG CCAAAGACCA AGAGCAGTTT CTGAAGTCCT CCTTTTCATC   10260
AGCTCTTTAT CAAACAGAAC ACTCTATAAA CAACCCATAG CCAGAAAACA GGATGTAGGA   10320
ACAATCACCA GCACACTCTA TAAACAACCC ATAGCCAGAA AACAGAATGT AAGGACAATC   10380
ACCAGCCATC TTTGTCAAT  AATTGATGGA ATAGAGTTGA AAGGAACTGG AGCATGAGTC   10440
ATATTTGACC AGTCAGTCCT CACTCTTATT TACTTGCTAT GTAAACTTGA GAAAGCTTTT   10500
TTCTCTTTGT GAACCTCAGG TTTTACATCT GAAAATGAGA ATTTTCAAT  AAAAGATTCC   10560
TAACTGGTCT TTCTGTTCCC ATATTCTGTG ATTTTTCAAT ATTTAGGATT TTTGGTAATC   10620
ACAATTACTT AGTTGTGGT  TGAGATAGCA ACACGAATCA GAACTATTTG GTGGACATAT   10680
TTTCAAAGGA GTAGCTCTCC ACTTTGGGTA AAGAAGTGAT GCNGGTCGTG GTGGCTCACG   10740
```

FIG. 14Q

```
CCTGTAATCC CAGCACTTTA GGGAGGCCAA GGCGGGTGGA TCACGAGGTC AGGAGATCGA    10800
GACCATCCTG GCTAACACGG TGAAACCCCG TCTCTACTAA AAATACAAA AAATTAGCCA     10860
GGCGTGGTGG CGGGCGCCTG TAGTCCCACG TACTCGGGAG GCTGAGGCAG GAGAATGGCA    10920
TGAACCAGGG AGGCGGAGCT TGCCGTGAGC CGAGATAGCG CCACTGCAGT CCCTCCTGGG    10980
CAAAAGAGCA AGACTGCGTC TCAAAAAAAA AAAAAAAAA AAAAAAGAA GTGTGTGGAG      11040
TAGCAGGACA CCTGCAACAA TAATATTTTT CTAAATCCCT CTGAAAAATG CTAATCAAAG    11100
GGTTTTTTC CTAAAAATTG TCTTAGAAAT AAAATTTCCC CTTTGGGAGA CCGAGGCTGG     11160
CAGATCACGA GGTCAGGAGA TAGAGACCAC GGTGAAACCC CGTCTCTACT AAAAATACTA    11220
AAAATTAGCC GGGNGTGGT GGTGGGTACA CCTGTAGTCC CAGCTACTTG GAGGCTGAGG     11280
CTGGAGAATC ACGTGAAC                                                  11298
```

FIG. 19A

```
human  MDTES NRRAN LA--L PQEPS SVPAF EVLEI SPQEV SSGRL
rat    MDTEn ksRAd LAlpn PQEsp saPdi ElLEa SPp-a kalp-
       ^^^^  . ^^  ^^    ^^^^   ^^ ^^ ^^ ^^ ^^ ^ .  : :  . .
mouse  MDTEn rsRAd LAlpn PQEsS saPdi ElLEa SP--- --a--
       ^^^^  . ^^  ^^    ^^^^   ^^ ^^ ^^ ^^ ^^    .  .

human  SVL DISHI EGDIF SSFKA GYPFW GAIFF SISGM LSIIS
rat    StL qtSdf ddevl llyrA GYPFW GAvlF vlSGf LSImS
       ^ ^  . . .  . .     ^ ^^^^^ ^^ ^^  ^^ ^  ^^^ ^
mouse  SVL yvSdf deevl llykl GYPFW GAvlF vlSGf LSIIS
       ^^^  . . .  . ^^ . .   ^^^^^ ^^ ^^  ^^ ^  ^^^^^ human  S CQKFF ETK-C FMASF STEIV VMMLF LTILG LGSAV SLTIC
rat    - Ckdit EddgC FvtSF iTElV lMlLF LTILa fcSAV lLily
         ^ . .  . . ^ ^ . ^^ ^ ^^ ^ ^^^ ^^^^   ^^^^  ^ . ^
mouse  - Cknvt EddgC FvASF tTElV lMMLF LTILa fcSAV lfTIy
         ^ . .   . . ^ ^^ ^^ ^ ^^ ^^^^^ ^^^^   ^^^^  ^ ^ ^
```

FIG. 19B

```
LKSAS SPPLH TWLTV LKKEQ EFLGV TQILT AMICL CFGTV VC eKpAS pPPqq TWqsf LKKEl EFLGV TQvLv qlICL CFGTV VC
 ^.^^ .^^ ^ ^^  ..  ^^^^  ^^^^^ ^^^^. .^^^^ ^^^^^ ^^
-K-A- aPPkq TWrTf LKKEl EFLGa TQILv qlICL CFGTi VC
 ^ ^  .^^ ^ ^^ ^.  ^^^^  ^^^^. ^^^^. .^^^^ ^^^^^ ^^

ERRNA TYLVR GSLGA NTASS IAGGT GITIL IINLK KSLAY IHIH

ERkNt lYLVR GSLGA NivSS IAaGl GIaIL IlNLs nnsAY mn-y
^^^^.  ^^^^ ^^^^^ ^..^^ ^^.^  ^^.^^ ^^^^. ..  ^^ ^^ .
ERkNt lYLVR GSLGA NivSS IAaGT GIamL IlNLt nnfAY mn-n
^^^^.  ^^^^ ^^^^^ ^..^^ ^^.^^ ^^.^^ ^^^^. ..^^^ ^^ ^

GAGEE LKGNK VPEDR VYEEL NIYSA TYSEL EDPGE MSPPI DL riGqE fersK VPdDR lYEEL hvYSp iYSaL EDtrE aSaPv vs
.^^^ ^. .^ ^^^^^ ^^^^^ ^^^^. .^^.^ ^^. ^  .^.^^
riGqE LeskK VPdDR lYEEL NvYSp iYSEL EDkGE tSsPv Ds
.^^^ ^...^ ^^^^^ ^^^^^ ^^^^. .^^^^ ^^.^^ .^.^^ ^
```

ISOLATION, CHARACTERIZATION, AND USE OF THE HUMAN β SUBUNIT OF THE HIGH AFFINITY RECEPTOR FOR IMMUNOGLOBULIN E

This application is a Divisional Application of U.S. application Ser. No. 07/869,933, filed Apr. 16, 1992, now U.S. Pat. No. 5,770,396.

BACKGROUND OF THE INVENTION

1. Field of the Invention

The present invention relates to DNA segments encoding the α, β, and γ subunits of the high affinity receptor for immunoglobulin E (IgE). The invention further relates to a method of producing the receptor by expressing DNA encoding its α, β, and γ subunits in a host cell simultaneously.

2. Related Art

Receptors that bind the Fc region of immunoglobulins ("Fc receptors") mediate immunoglobulin transport across membranes, stimulate a variety of cellular activities induced by antigen-antibody complexes, and possibly regulate the biosynthesis of antibodies. Three of the receptors (the receptor for polymeric immunoglobulin (Mostov et al. (1984) Nature (London) 308:37–43), the Fc receptors on macrophages and lymphocytes (Ravetch et al. (1986) Science 234:718–725), and the high affinity $Fc_\epsilon$ receptor on mast cells and basophils (Kinet et al. (1987) Biochemistry 26:4605–4610; Shimizu et al. (1988) Proc. Natl. Acad. Sci USA 85:1907–1911; Kochan et al. (1988) Nucleic Acids Res. 16:3584) share a common feature: their immunoglobulin-binding portion contains two or more immunoglobulin-like domains.

The high affinity IgE receptor $Fc_\epsilon RI$ is responsible for initiating the allergic response. Binding of allergen to receptor-bound IgE leads to cell activation and the release of mediators (such as histamine) responsible for the manifestations of allergy. This receptor is a tetrameric complex $\alpha\beta\gamma_2$ which is found on the surface of mast cells and basophils. The α and β subunits have not been detected in other hematopoietic cells although the γ chains of FceRI are found in macrophages, NK cells and T cells where they associate with the low affinity receptor for IgG (FcγRIII) or with the T cell antigen receptor.

The genes for α and γ, both have been localized on human (Le Coniat, 1990) and mouse chromosome 1. (Huppi, 1988; Kinet et al. 1987; Kochan et al. 1988; Shimizu et al. 1988; Ra et al. 1989.) The gene for mouse β has been localized on mouse chromosome 19 and is believed to be a single gene (Huppi, 1989). The structures of the α gene in the rat (Tepler, 1989) and of the γ gene (Kuster, 1990), but not of the β gene have been characterized in the human.

The receptor with high affinity for the IgE $Fc_\epsilon RI$ is found exclusively on mast cells, basophils, Langerhans cells, and related cells. Aggregation of IgE occupied $Fc_\epsilon RI$ by antigen triggers both the release of preformed mediators such as histamine and serotonin, as well as stimulation of the synthesis of leukotrienes. It is the release of these mediators that results in the allergic condition.

The most thoroughly characterized $Fc_\epsilon FI$ is that of the rat basophilic leukemia (FEL) cell line. It consists of three different subunits: (1) a 40–50 Kilodalton (Kd) glycoprotein alpha chain which contains the binding site for IgE, (2) a single 33 Kd beta chain and (3) two 7–9 Kd disulfide linked gamma chains (H. Metzger et al., Ann. Rev. Immunol. 4:419–470 (1986).

Complementary DNA (cDNA) for the rat α subunit has been isolated (J.-P. Kinet et al., Biochemistry 26:4605–4610 (1987)). However, previously there has been no disclosure of the isolation and characterization of the β and γ subunits nor has it been possible to express IgE-binding by transfected cells (J.-P. Kinet et al., Biochemistry 26:4605–4610 (1987); A. Shimizu et al., Proc. Natl. Acad. Sci. USA 85:1907–1911 (1988)).

Molecular cloning of some of the subunits in rodents and humans has permitted the reconstitution of surface expressed receptor complexes by trasfection. One of the surprising findings from these studies was the differential requirement for surface expression among different species. Cotransfection of the three chains, α, β and γ is required to promote efficient surface expression of the rat (Blank, 1989) or mouse receptor (Ra., 1989). By contrast, some surface expression of the human αγ complex can be achieved by cotransfecting α and γ alone suggesting that β may not be necessary (Miller, 1989). This result and previous inability to clone the gene for the human β subunit raised the possibility that human beta might not exist and that αγ complexes might exist naturally in human cells.

The high affinity IgE receptor $Fc_\epsilon RI$ is a tetrameric hetero-oligomer composed of an α chain, a β chain and two disulfide-linked γ chains (chains and subunits will be used interchangeably herein). The β chain contains four transmembrane (TM) segments and long cytoplasmic domains which are thought to play an important role in intracellular signalling. It was very difficult to determine whether a human beta subunit even existed, and if so, to isolate its gene. The present invention has overcome these difficulties and surprisingly provided cDNA clones for the human β subunit of $Fc_\epsilon RI$.

The invention still further provides a method of producing the complete human $Fc_\epsilon RI$ receptor, and for inhibiting formation of the receptor or its function, by inhibiting the β subunit.

SUMMARY OF THE INVENTION

It is an aspect of this invention to provide nucleic acid segments encoding $Fc_\epsilon RI$ subunits.

It is an aspect of this invention to provide nucleic acid sequences encoding the α, β, and γ subunits of $Rc_\epsilon RI$. In particular, this invention relates to DNA sequences. An aspect of the present invention is the structural characterization and the sequence of the complete human β gene and cDNA. Successful cloning of the human beta was not expected and was fraught with failures. Attempts to clone the human beta by simply using a rodent beta probe to screen various cDNA libraries failed to isolate a cDNA clone encoding human beta. Only a very short fragment (153 bp) with homology to rodent beta was isolated. However because this fragment may have been a portion of a beta-like molecule such as CD20, known to be homologous to beta in that region, PCR techniques were used to clone the human beta by using the information from the rodent beta sequence. However, although the homologies between human and rodent beta were 69% in the coding region, that was not sufficient for a PCR reaction. Human beta isolated by this method also failed.

The existence of human beta was questioned because human beta was believed not necessary for expression of the alpha-gamma complex. Studies of gene transfer indicated that the transfer by transfection of the three genes for alpha, beta and gamma was necessary for the expression of the rat and mouse receptor. However, transfection of human alpha and gamma was sufficient to promote the surface expression of the human receptor in fibroblasts suggesting that the human beta was not necessary for the surface expression of the human receptor. That result raised the interesting question of the existence of human beta.

Human beta was not necessary for the function of the alpha-gamma complex. Transfection of the cytoplasmic tail of gamma is sufficient for cell activation. Several groups made the observation that the cytoplasmic domain in the gamma chain was sufficient to mediate a number of biochemical signals leading to cell activation. These signals include tyrosine kinase activation, hydrolysis of phosphoinositides, calcium mobilization, production of IL2 in T cells, degranulation of mast cells and cell killing. It was demonstrated that the cytoplasmic domains of gamma contain a motif of 10–12 amino-acid residues responsible for cell activation. This motif is sufficient to trigger many different signals in different cells. It is transferable, and seemed to be interchangeable. Again these findings raised the question of the existence of human beta. If the gamma chain is sufficient for cell activation, perhaps there was no need for a beta.

The inability to clone the human beta or even to detect transcripts for human beta in human cells (by using rat or mouse probes) also raised the question of the existence of human beta.

Cloning required inventive methods and persistence. The 153 bp fragment used to screen further cDNA libraries did not work. However, assuming that the 153 bp could be part of human beta even though the homology was only about 70%, a 25 kb genomic clone was found. Smaller inserts were found which seemed to hybridize specifically with oligonucleotide probes corresponding with rat beta sequences. All these inserts (a total of 11 kb) were sequenced to reconstitute the different exons in the quest for those encoding human beta. Using what should be the beginning of the first exon from the putative human beta gene, a putative cDNA human beta sequence was generated by PCR (by using first strand reverse transcripts from human basophils as templates for the PCR reaction.)

It was demonstrated that the gene and cDNA isolated encoded human beta. The isolated gene and cDNA could correspond to a beta-like or CD20-like molecule which is homologous to rodent beta. However, the homology of 69% is not a criteria for the demonstration that these sequences encode human beta. Co-expression of alpha, beta and gamma in transfectants was preferred for the demonstration that the cDNA generated is indeed encoding human beta. However these experiments were not successful for the following reasons:
1. Co-transfection of human alpha and gamma is sufficient for surface expression and functional reconstitution of the receptor on fibroblasts.
2. When human beta cDNA is co-transfected with alpha and gamma, the efficiency of transfection is not increased.

Therefore conditions were used where co-transfection of alpha and gamma does not work to see if human beta and not CD20 could promote expression of the complete complex. This was done by truncation of the cytoplasmic tail of human gamma. In these conditions, co-transfection of human alpha with truncated human gamma does not result in the expression of the complex. However, co-transfection of human beta (but not of CD20) with alpha and truncated gamma resulted in the expression of a functional complex capable of binding IgE. This assay showed that human beta could associate specifically with the two other chains.

The new results demonstrated the previously unsuspected importance of human beta. The two FIGS. 20 and 21 show the results obtained from FACS analysis (IgE binding) of cells transfected as explained herein. In FIG. 21 the transfection of human alpha and gamma in COS-7 cells is shown to be sufficient for expression of the alpha-gamma complex on the surface of the transfectants. It also shows that human beta and not rat beta associate efficiently with human alpha and that therefore, rat beta cannot replace human beta.

In FIG. 20 transfection of alpha-gamma in KU812 showed very little expression of receptors. The level of expression is similar to the level obtained after transfection of beta and gamma. Therefore this level may be attributable to the endogenous alpha (for beta and gamma transfection) or to the endogenous beta (for alpha and gamma transfection). By contrast the level of expression after co-transfection of the three cDNAs is very substantial.

The conclusions are:
1. In mast cells and basophils, what regulates the level of expression of the receptor may be different than in fibroblasts.
2. In human mast cells and basophils, receptor expression requires the presence of alpha, beta and gamma whereas in transfected fibroblasts, human alpha and gamma are sufficient.

The beta subunit gene spans approximately 10 kb and contains seven exons. There is a single transcription initiation site preceded by a TATA box. The first exon codes for the 5' untranslated region and a portion of the N-terminal cytoplasmic tail. Transmembrane (TM) 1 is encoded in exon 2 and 3, TM 2 in exon 3 and 4, TM 3 in exon 5 and TM 4 in exon 6. The seventh and final exon encodes the end of the C-terminal cytoplasmic tail and the 3' untranslated sequence. The human β gene appears to be a single copy gene.

Two corresponding transcripts, detected as a doublet around 3.9 kb, are present in cells of mast cell and basophil lineage from different individuals but not in the other hematopoietic cells tested. The human β protein is homologous to rodent β. The consensus amino acid sequences for human, mouse and rat β show 69% identical residues.

It is a further aspect of the invention to provide polypeptides corresponding to the α, β, and γ subunits of $Fc_eRI$, more particularly to the human β subunit isolated from its natural environment. This may be defined to include the amino acid sequences of the polypeptides either produced by recombinant methods, or synthesized by apparatus known to those of skill in the art, or isolated and purified by protein isolation and purification methods. The polypeptides comprise the entire amino acid sequence, or selected portions thereof, for example, portions (domains) of the human beta subunit that are essential for (1) assembly of the receptor; (2) cell activation, and/or (3) complexing with the alpha and gamma subunits. "Natural environment" may be defined to include the subunits in the cells in which they naturally occur, in the form and with other types of proteins and cellular components generally in structural or functional association with the subunits.

It is another aspect of the invention to provide a recombinant DNA molecule comprising a vector and a DNA segment encoding the α, β, or γ subunits of $Fc_eRI$.

It is a further aspect of the invention to provide a cell that contains the above-described recombinant DNA molecule.

It is another object of the invention to provide a method of producing polypeptides having amino acid sequences corresponding to the α, β, and γ subunits of $Fc_eRI$, both in rodent and human species.

Analysis of the surface expression of transfected receptors in fibroblast-like cells indicates that human αγ and αβγ complexes are expressed with comparable efficiency. Unexpectedly, assembly rules were different in other human cells. In addition, human β interacts with human α slightly more efficiently than does rat β. by contrast, both rat and mouse β interact with their corresponding α chains much more efficiently than does human β, demonstrating a strong species specificity of the α-β interaction in rodents.

It is a further object of the invention to provide a method of producing a functional Fc$_\epsilon$RI receptor.

In one embodiment, the present invention relates to DNA segments that code for polypeptides having amino acid sequences corresponding to the α, β, and γ subunits of Fc$_\epsilon$RI.

In another embodiment, the present invention relates to polypeptides having amino acid sequences corresponding to the α, β, and γ subunits of Fc$_\epsilon$RI.

In a further embodiment, the present invention relates to recombinant DNA molecules comprising a vector and a DNA segment that codes for a polypeptide having an amino acid sequence corresponding to the α, β or γ subunits of Fc$_\epsilon$RI.

In yet another embodiment, the present invention relates to a cell that contains the above-described recombinant DNA molecule.

In a further embodiment, the present invention relates to a method of producing polypeptides having amino acid sequences corresponding to the α, β, and γ subunits of Fc$_\epsilon$RI.

In another embodiment, the present invention relates to a method of producing a functional FCERI receptor comprising introducing into a host cell DNA segments encoding the α, β, and γ subunits of Fc$_\epsilon$RI; and effecting expression of said DNA segments under conditions such that said receptor is formed. Expression of the receptor on the surface of cells COS-7 or CHO os achieved by the present invention when the cDNA for all three subunits of FCERI are simultaneously cotransfected. This success in expression of IgE binding permits detailed analysis of the IgE-receptor interaction and thus enables the development of therapeutically effective inhibitors.

An aspect of the invention is to stem the cascade of allergic responses resulting from aggregation of the high affinity receptor for IgE, by inhibiting the essential participation of the human beta subunit. The beta subunit is the target to inhibit receptor aggregation and/or the function of the translate signal. Such an inhibition has widespread applications for prevention and treatment of allergic diseases because the undesirable events cascading from the receptor-IgE interaction are allergen independent and arise from various cell types: mast cells, basophils, Langerhans cells and the like.

Inhibitors of beta include chemical preparations that attack the structure or function of the chain, anti-sense nucleic acid sequences, amino acid sequences capable of binding to the beta subunit polypeptide, and monoclonal antibodies directed to the subunit.

Effective amounts of the beta subunit inhibitors will be determined after in vitro cell assays, assays in animal models, and clinical trials.

Effective amounts of the inhibitors will be combined with a pharmaceutically acceptable carrier. Because of the variety of cell types in which the allergic response is related to the Fc$_\epsilon$RI, and because the reaction is allergen independent, route of administration may be either systemic or atopic.

Candidate inhibitor substances are tested by methods disclosed herein.

In vitro assays for inhibitor substances are provided through host cells transfected with nucleic acid sequences for encoding the human alpha, beta and gamma subunits, complexed or incubated with inhibitors. Cell activation effected by the Fc$_\epsilon$RI receptor is triggered and compared in the presence versus absence of inhibitors. Many assays are available.

Further objects and advantages of the present invention will be clear from the following description and examples.

BRIEF DESCRIPTION OF THE DRAWINGS

FIGS. 1A–1C. The nucleotide sequence (SEQ ID NO:10) and predicted amino acid sequence (SEQ ID NO:11) of human Fc$_\epsilon$RI alpha cDNA are shown.

FIG. 2. The amino acid sequence homology of rat Fc$_\epsilon$RI alpha subunit (R, SEQ ID NO:12), human Fc$_\epsilon$RI alpha subunit (H, (SEQ ID NO:13); and mouse Fc$_\epsilon$RI alpha subunit (M, (SEQ ID NO:14) are shown. The regions of identity between the three are boxed. The number one position corresponds to the site of the predicted mature N-terminus of each protein.

FIGS. 6. (A–F) Nucleotide (SEQ ID NO:22) and deduced amino acid (SEQ ID NO:23) sequences of the cDNA coding for the β subunit. Beginning at the arrowhead (▼), an alternative sequence (FIG. 6G) was observed in six clones. The putative transmembrane domains are underlined. The tryptic peptides of the β subunit, from which the amino acid sequences were determined directly, are bracked (< >). A putative poly (A) signal near the end is underlined. (FIG. 6G) continuation of the nucleotide sequence (SEQ ID NO:24) of the deleted form of β cDNA, 3' to the junction indicated in B (▼).

FIG. 7. Expression of cDNA coding for the β subunit. (A) Comparison of in vivo and in vitro translation products. RBL cells were grown in [$^{35}$S]cysteine containing medium. The detergent extract of the cells was precipitated with mAbβ(JRK) and, after vigorous washing, extracted with sample buffer and electrophoresed (lane 1). This experiment employed concentrations of detergent high enough to dissociate the receptor completely. A transcript from the β cDNA was treated in vitro in [$^{35}$S]methionine-containing medium (lanes 2, 3 and 5).

Figure 3:
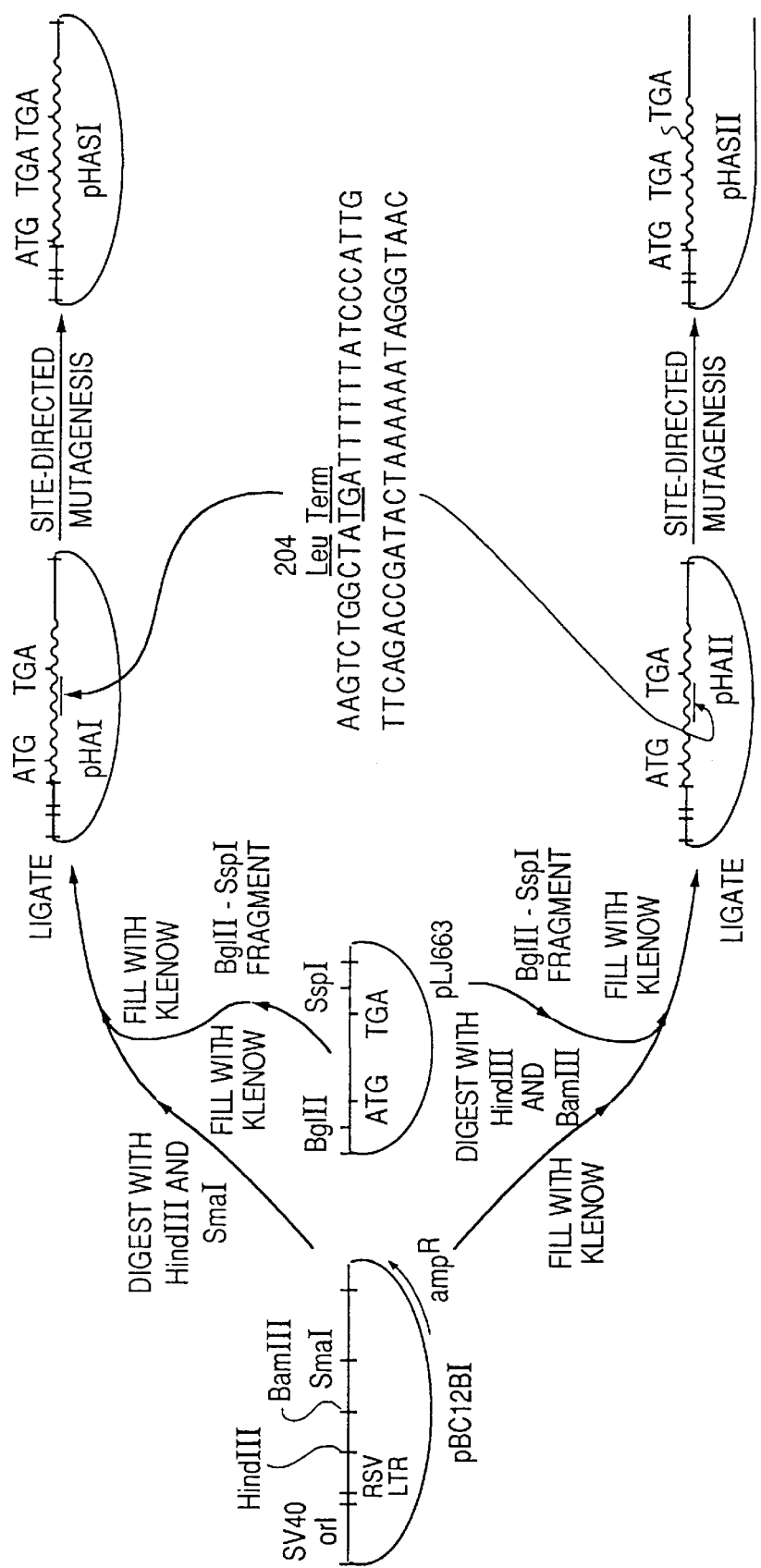
FIG. 3. A flow chart showing the construction of eukaryotic expression vectors which direct the synthesis of a complete biologically active Fc$_\epsilon$RI alpha chain (pHAI, pHAII) or a soluble, secreted, biologically active Fc$_\epsilon$RI alpha chain (pHASI, pHASII) is presented. The sequence shown in this Figure is also disclosed in SEQ ID NO:20. The sequences shown in the pEVA construct are also shown in SEQ ID NOs. 15–17; the sequences shown in the pEVHA construct are also shown in SEQ ID NOs. 18–19; the sequences shown in the pEVHAS construct are also shown in SEQ ID NOs 20–21.

A control incubation contained no cDNA (lane 4). The mixtures were allowed to react with monoclonal antibodies to the β subunit after a clearing immunoprecipitation. The specific washed precipitates were dissolved in sample buffer and electrophoresed: lanes 2 and 4, mAbβ(JRK); lane 3, mAbfl(NB); lane 5, irrelevant monoclonal antibody [mAbβ (LB)]. An autoradiograph of the 12.5% polyacrylamide gel on which the specimens were analyzed under reducing conditions is shown. (B) Localization of one epitome to the NH$_2$-terminal peptide of the β subunit. A β cDNA-containing vector was digested with HhaI before transcription using T7 polymerase. The resulting mRNA was translated to generate an NH$_2$-terminal peptide of the β subunit β(amino acid 1-21) labeled with [$^{35}$S]methionine. The mixture was allowed to react with mAbβ(JRK) (lane 1) and the irrelevant mAb(LB) (lane 2). The precipitates were analyzed on a 17% gel under nonreducing conditions. (C) Expression by *E. coli* of a COOH-terminal fragment of the β subunit. A HinfI fragment, containing nucleotides 499–787, was subcloned into an *E. coli* expression vector (Crowl et al. (1985) Gene 38:31–38) and extracts were prepared. The proteins were electrophoresed as in A and transferred to nitrocellulose paper. The latter was allowed to react sequentially with monoclonal antibody mAbβ(NB), developed with alkaline phosphatase-conjugated goat anti-mouse IgG (Fc), and developed in the usual way (Rivera et al, (1988) Mol. Immunol.). An enlargement of the lower half of the immunoblot is shown. Lane 1, extract from transformant without insert; lane 2, extract from transformant with insert in wrong direction; lane 3, extract from transformant with insert correctly oriented. (D) Reactivity of β subunits with polyclonal antibodies induced by *E. coli*-expressed HinfI fragments. Purified IgE-receptor complexes were electrophoresed, transferred to nitrocellulose paper, and allowed to react with antibodies and subsequently with an appropriate alkaline phosphatase-conjugated anti-immunoglobulin antibody. Lane 1, mAbβ(JRK); lane 2, mAbβ(NB); lane 3, immune serum to fragment A; lane 5, immune serum to fragment B; lanes 4 and 6, preimmune sera corresponding to the immune sera in lanes 3 and 5, respectively; lanes 7 and 8, second antibody only. This gel was run without molecular weight standards.

FIG. 8. Hydropathicity plot of predicted sequence for the β subunit. The procedure and hydropathicity scale recommended by Englemen et al. (Englemen et al. (1986) Annu. Rev. Biophys. Biophys. Chem. 15:321–353) was used. The net hydropathicity value for the 20 amino acids for each successive "window" is plotted at the position corresponding to the 10th residue. A net free energy of >20 kcal (1 cal=4.18 J) for transfer to water suggests a transmembrane segment (Engelman et al. (1986) Annu. Rev. Biophys. Biophys. Chem. 15:321–353).

FIG. 9. Nucleotide sequence (SEQ ID NO:26) of the γ subunit of rat Fc$_\epsilon$RI and the amino acid sequence (SEQ ID NO:27) that it predicts. The putative transmembrane domain is underlined. Amino acid residues are numbered starting with the first residue of the mature protein. Residues 5' to residue 1 have negative numbers and include the residues encoding a putative signal peptide according to the criteria of G. von Heijne (Nucleic Acids Res. 14:4683–4690 (1986)). The N-terminal and C-terminal cleavage sites are indicated by an arrow. The four tryptic peptides which were covered and sequenced are bracketed. An asterisk denotes an ambiguous residue in the sequence of the first tryptic peptide.

FIG. 10. Hydropathicity plot of predicted sequences of Fc$_\epsilon$RI α subunit (FIG. 10A), β subunit (FIG. 10B) and γ subunit (FIG. 10C). The hydropathicity scale is according to Engelman et al. (Ann. Rev. Biophys. Biophys. Chem. 15:321–353 (1986)). The summed hydropathicity values for the 20 amino acids in successive "windows" is plotted at the position corresponding to the tenth residue.

Figure 11B:
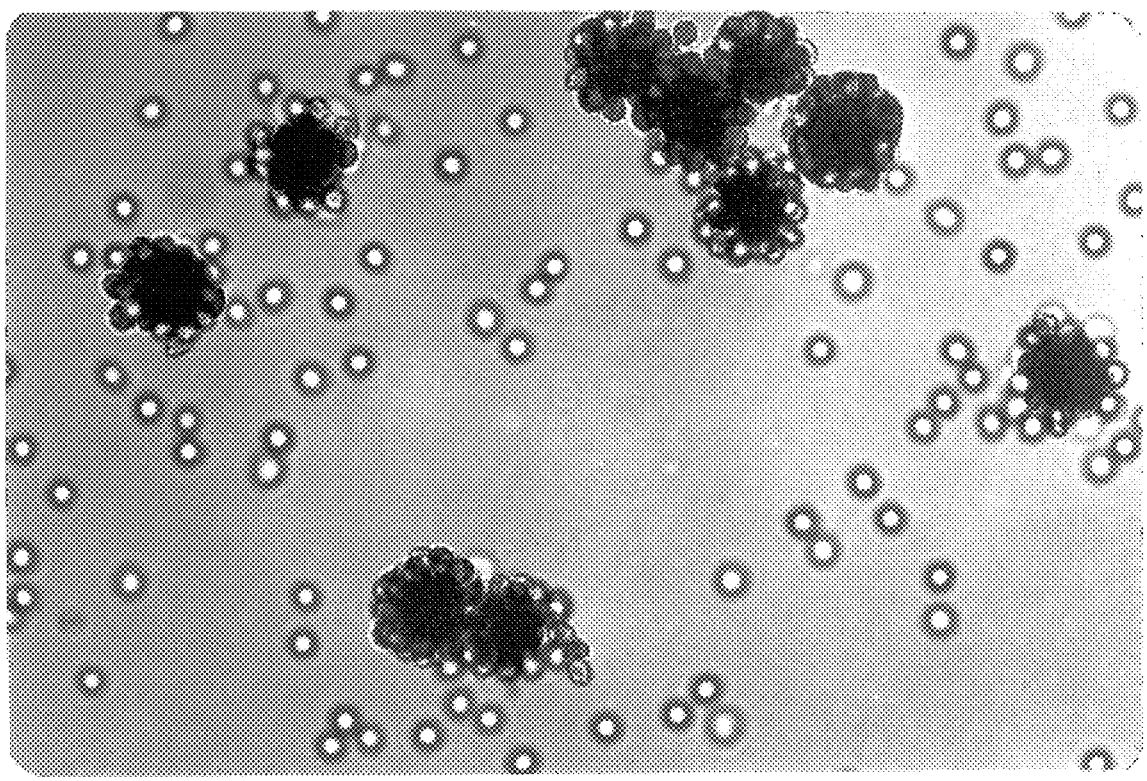
Figure 11C:
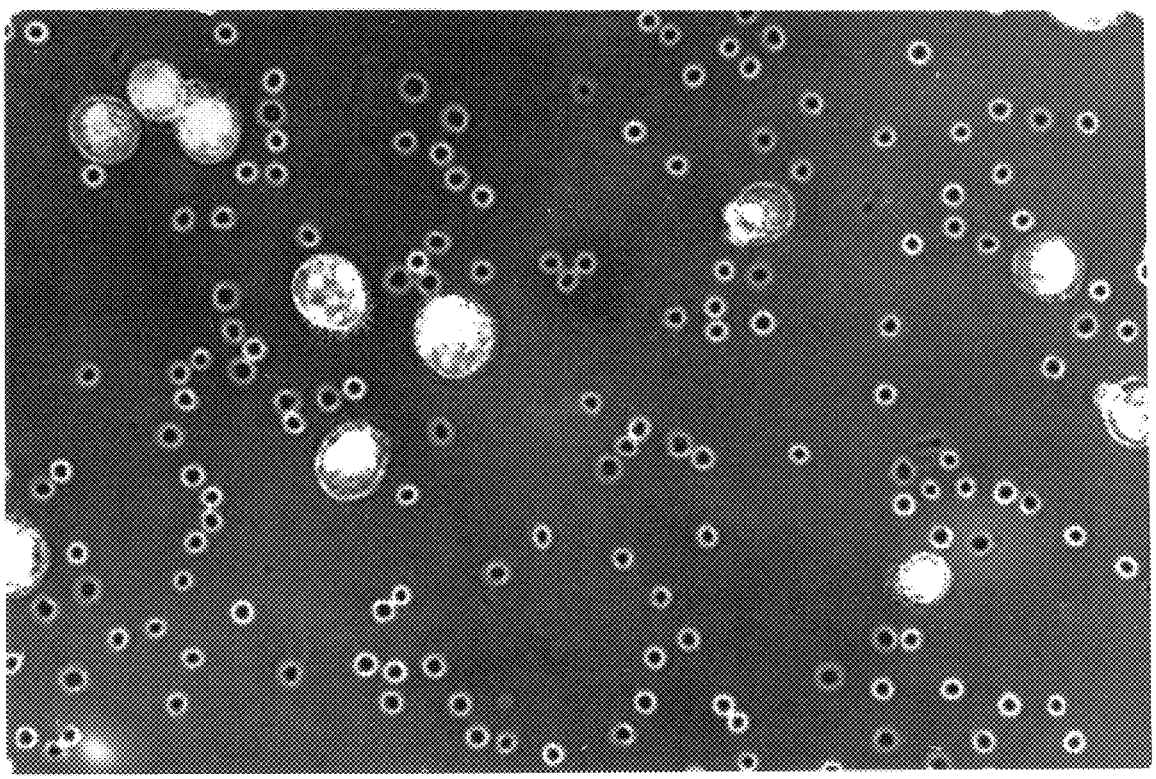
Figure 11D:
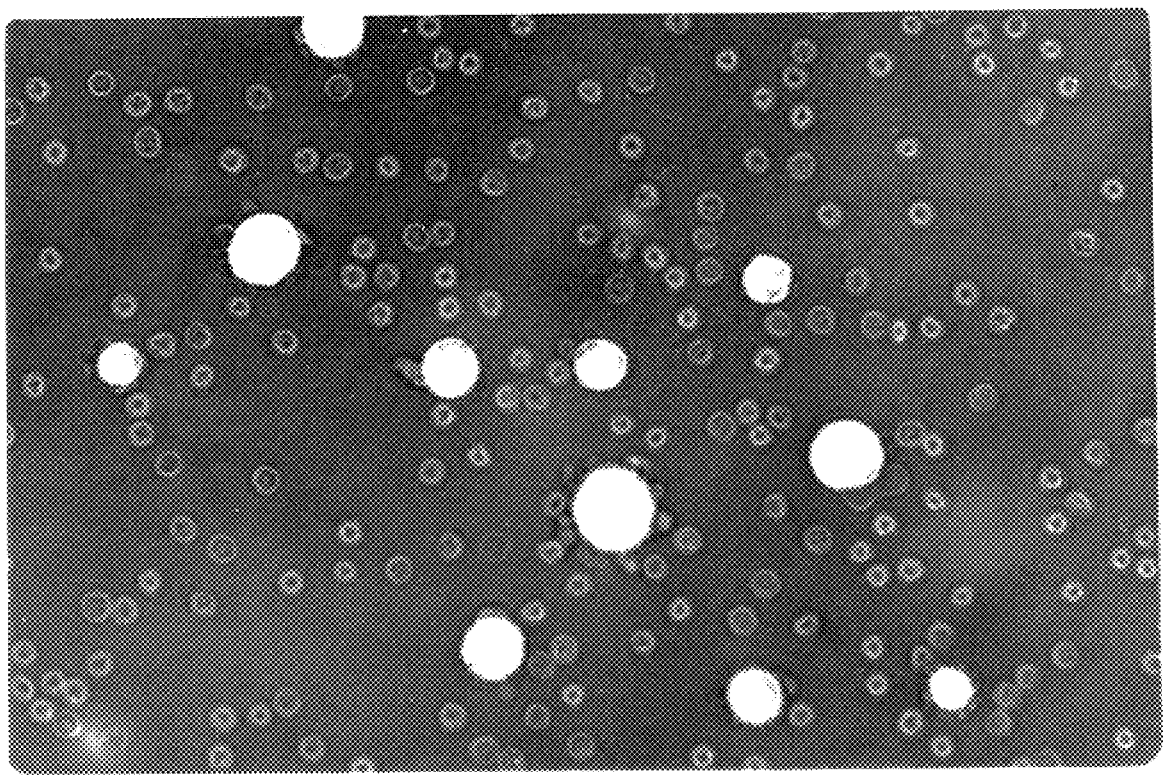

FIG. 11. Formation of IgE rosettes by transfected COS 7 cells and RBL cells. COS 7 cells were cotransfected with the coding portions of α, β and γ cDNAs and sensitized with mouse IgE anti-DNP before being exposed to red cells derivatized with TNP (FIG. 11A). As a positive control, RBL cells were similarly tested for rosette formation (FIG. 11C). The specificity of the rosetting assay was assessed by preincubating the cotransfected COS 7 cells (FIG. 11B) and RBL cells (FIG. 11D) with rat IgE (which lacks the anti-DNP activity) prior to the addition of the mouse anti-DNP IgE.

Figure 12A:
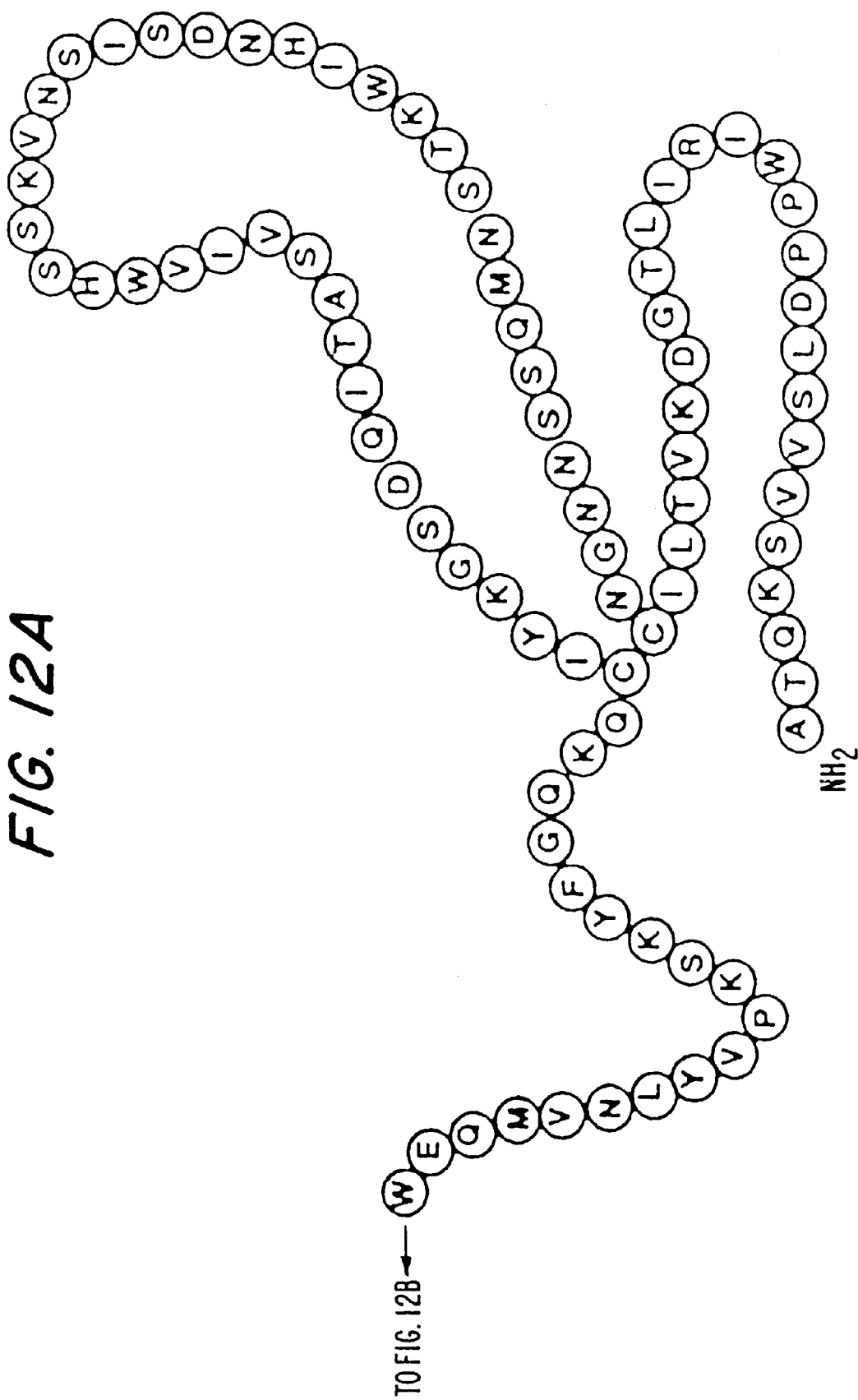
Figure 12C:
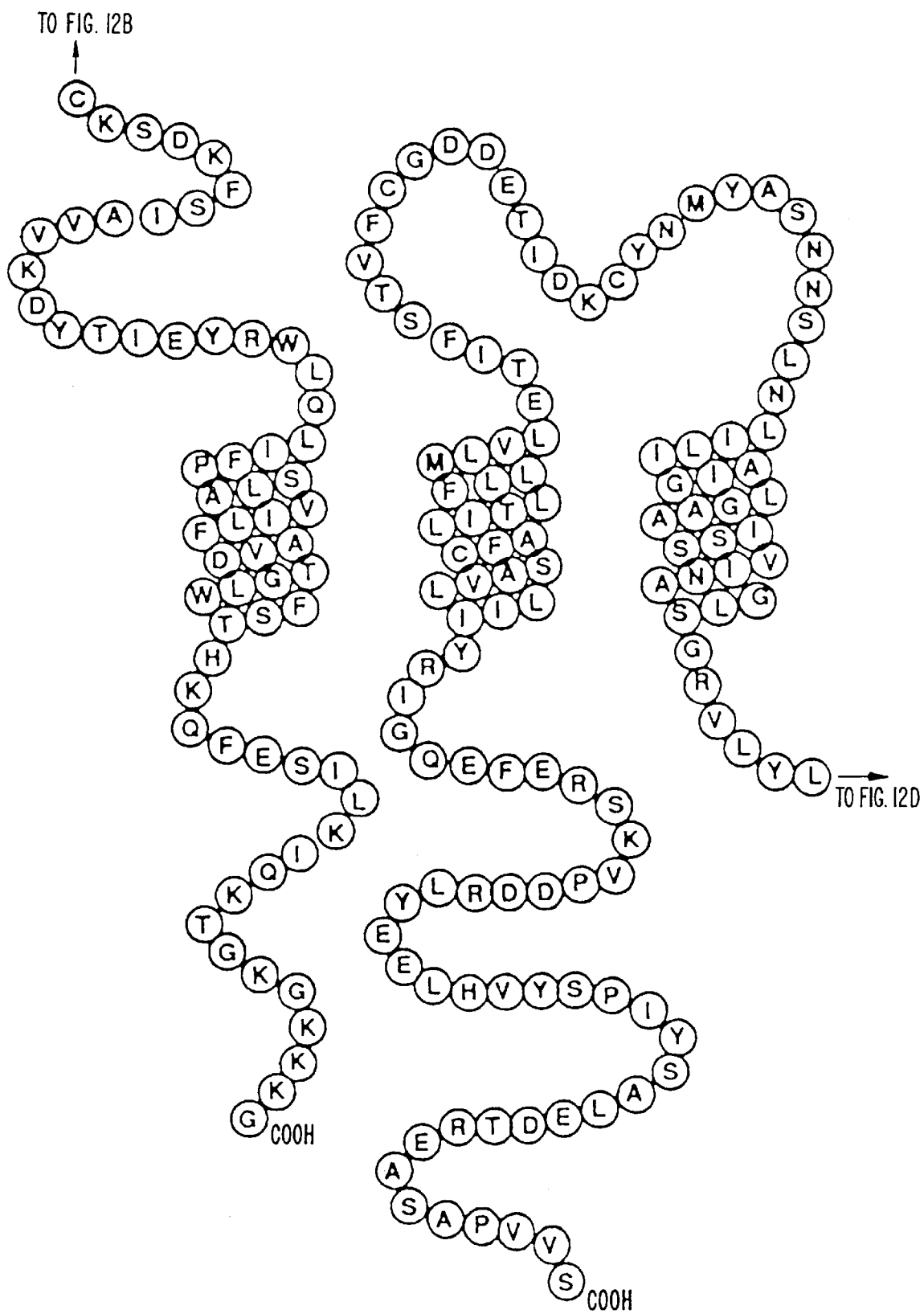
Figure 12D:
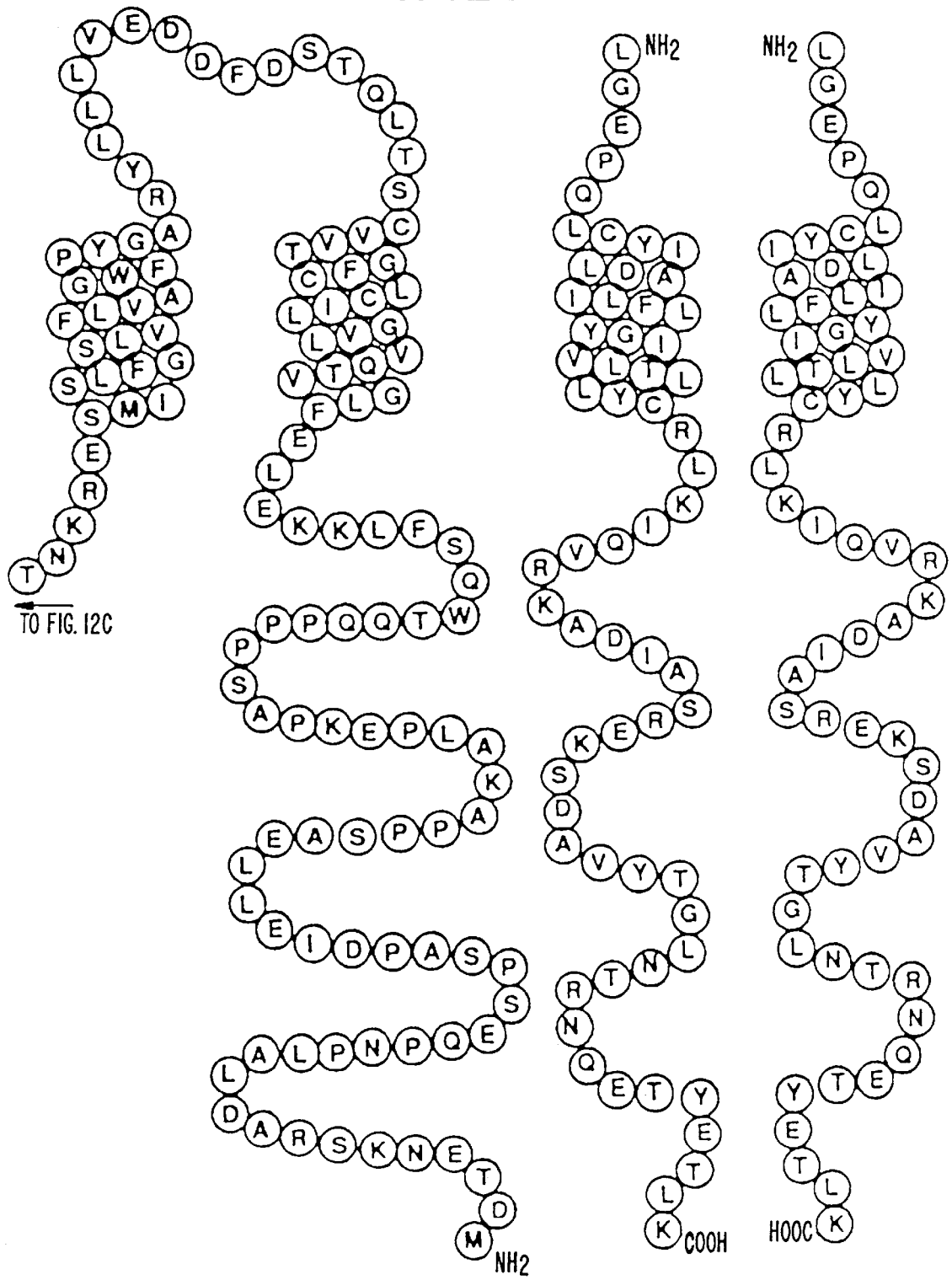

FIG. 12. Model of the tetrameric high affinity receptor for IgE. The polypeptides (SEQ ID NOs 28–30) are shown in their fully processed form. The receptor is oriented such that the large extracellular portion of the α subunit is shown at the top and the remainder of the chain on the left. To the right of the α subunit (SEQ ID NO:28) is the β subunit (SEQ ID NO:29) with its four transmembrane segments and to the right of it, the dimer of γ chains (SEQ ID NO:30). Cysteines 26 and 68 and cysteines 107 and 151 in the α chain are paired as they are likely to be disulfide linked, as are the homologous cysteines in the Fcγ receptors (M. Hibbs et al, J. Immunol. 140:544–550 (1988)). The putative transmembrane segments have all been shown as consisting of 21 residues and would be expected to be in an α-helical conformation. The single letter code for amino acids is used (M. Dayhoff et al., in Atlas of Protein Sequence and Structure, Suppl. 3, ed. M. Dayhoff, 363–373, Natl. Biomed. Res. Fndtn., Washington D.C. (1978)). Every 10th residue (starting from the N-terminus) is shaded.

Figure 13:
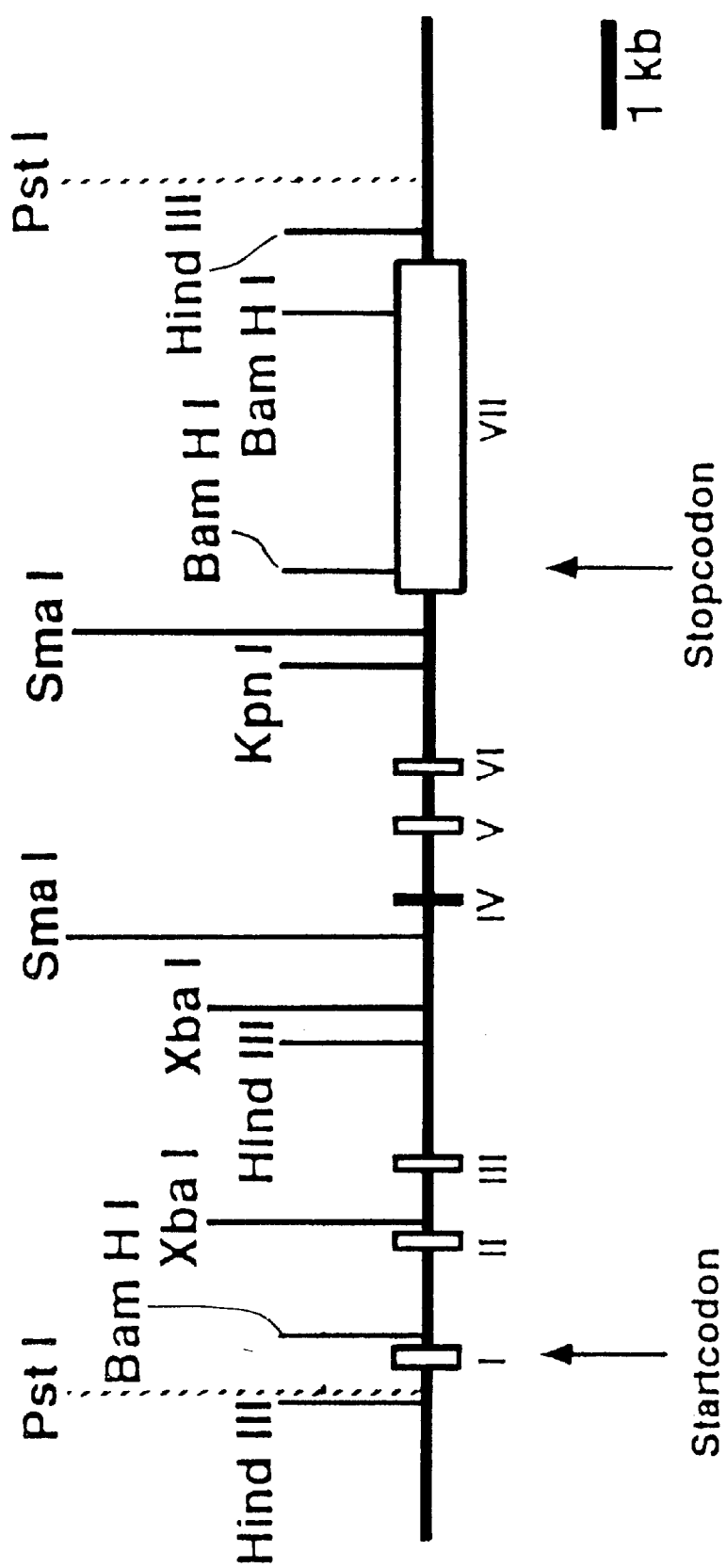

FIG. 13. Restriction map structure of the human β gene and exon-intron are shown. The positions of the 7 exons are depicted by boxes. The location of the start and stop codon is indicated.

FIGS. 14A–14Q. Nucleotide sequence (SEQ ID NO:31) of the human FcεRI β chain gene. The 7 exons are shown in bold. The numbering of nucleotides is relative to the start codon. The TATAA box, translation initiation codon (ATG), termination codon (TAA) and the potential polyadenylation signals (AATAAA) are underlined. Bases which not determined with certainty are denoted as N.

Figure 15:
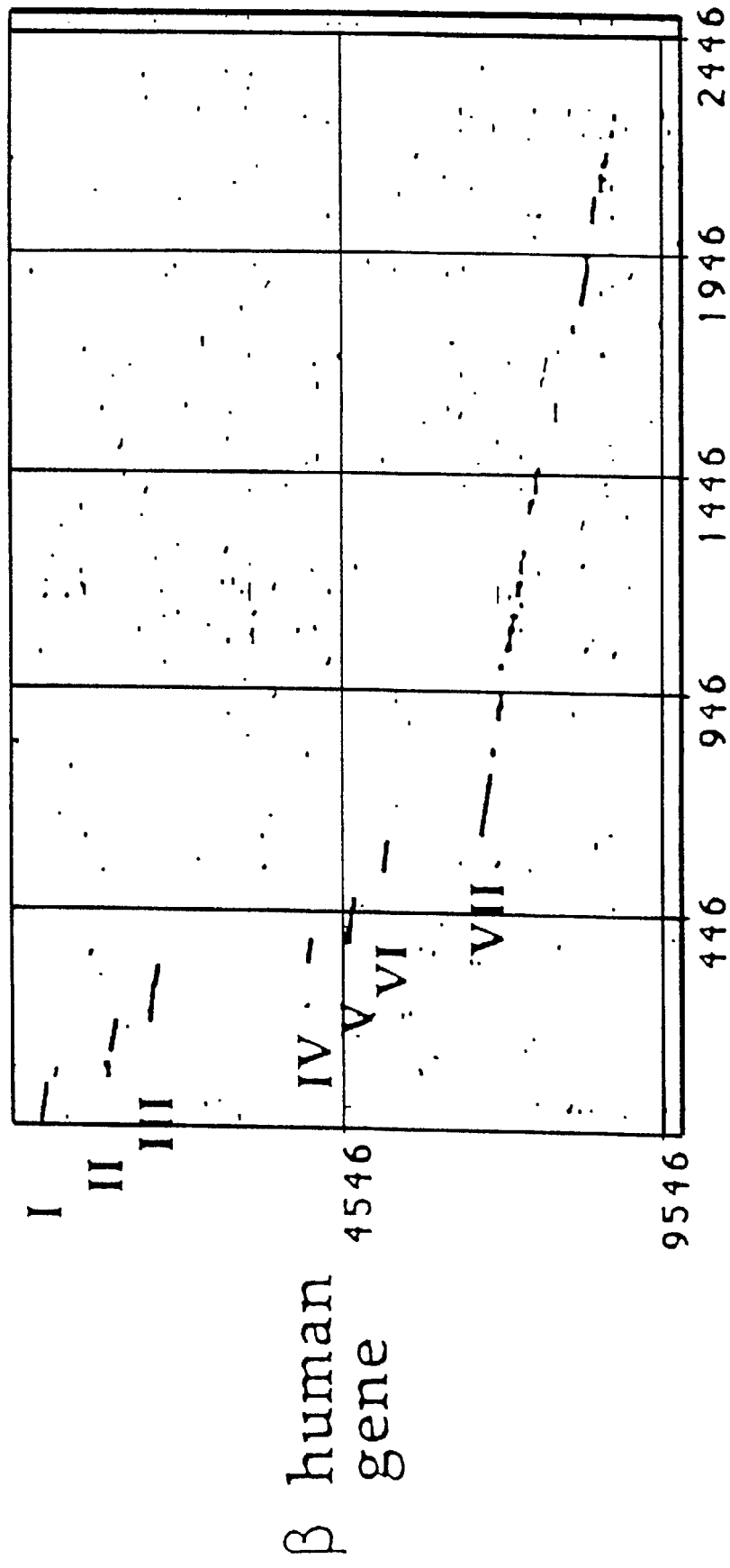

FIG. 15. Comparison of the human β gene and rat β cDNA sequences by a dot matrix blot. The Pustell DNA Matrix of the Macvector program was used with a window of 30 nucleotides and a minimum score of 63%. The Roman numerals indicated on the left correspond to the seven exons.

Figure 16A:
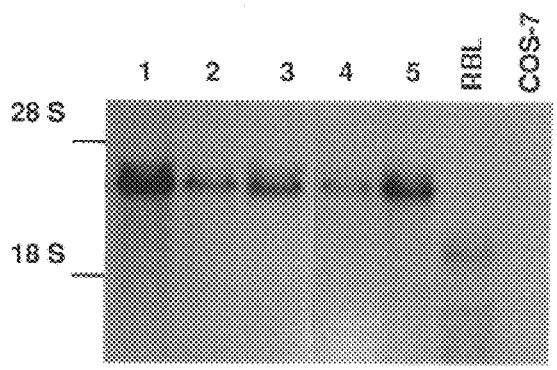
Figure 16C:
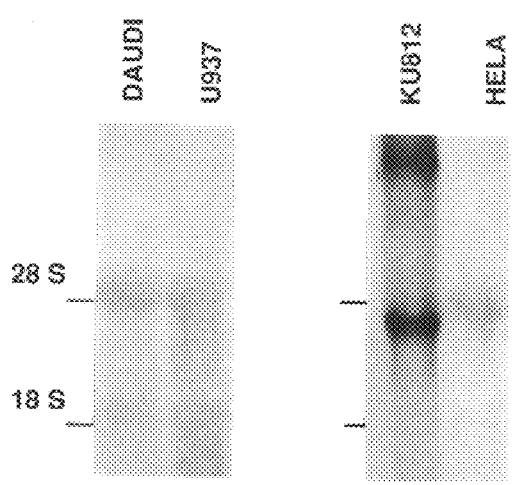
Figure 16B:
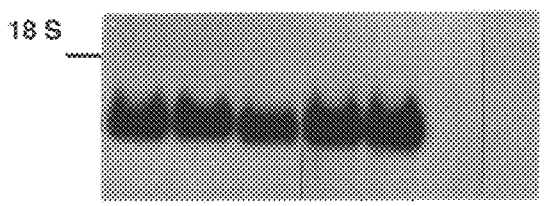

FIG. 16. Presence of transcripts in basophils are shown. Ten micrograms of total RNA from basophil enriched leukocytes and various other cells were fractionated on a denaturing agarose gel before being transferred to Nytran membranes and hybridized with human β cDNA probes (nucleotides +306 to +456 for FIG. 16A and nucleotides −2 to +790 in FIG. 16C). The membrane shown in Panel A was stripped and rehybridized with a full length human α cDNA probe (FIG. 16B).

FIG. 17. Determination of the transcription initiation site.

Figure 17A:
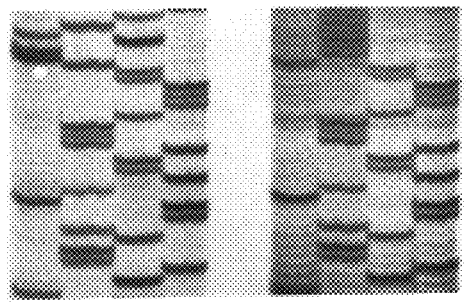
Figure 17B:
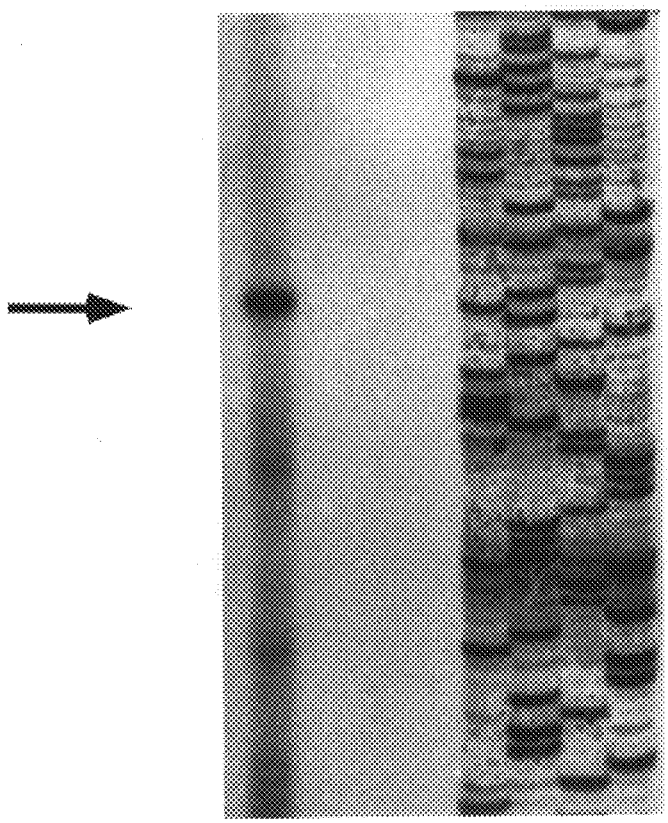

FIG. 17A. RNA from basophils was reverse transcribed, poly A+ tailed at both ends with terminal transferase and amplified with PCR. The amplified product (cDNA) and the genomic DNA (gene) ware sequenced with an identical primer and the respective sequencing reactions were run in parallel on a 8% acrylamide gel. The arrow marks the transcription start site. FIG. 17B RNA from basophils (lane 1) or tRNA (lane 2) were used in the primer extension and the extended products analyzed on a 5% polyacrylamide urea gel in parallel with the sequencing reactions of the genomic DNA. The arrow marks the transcription start site.

Figure 18:
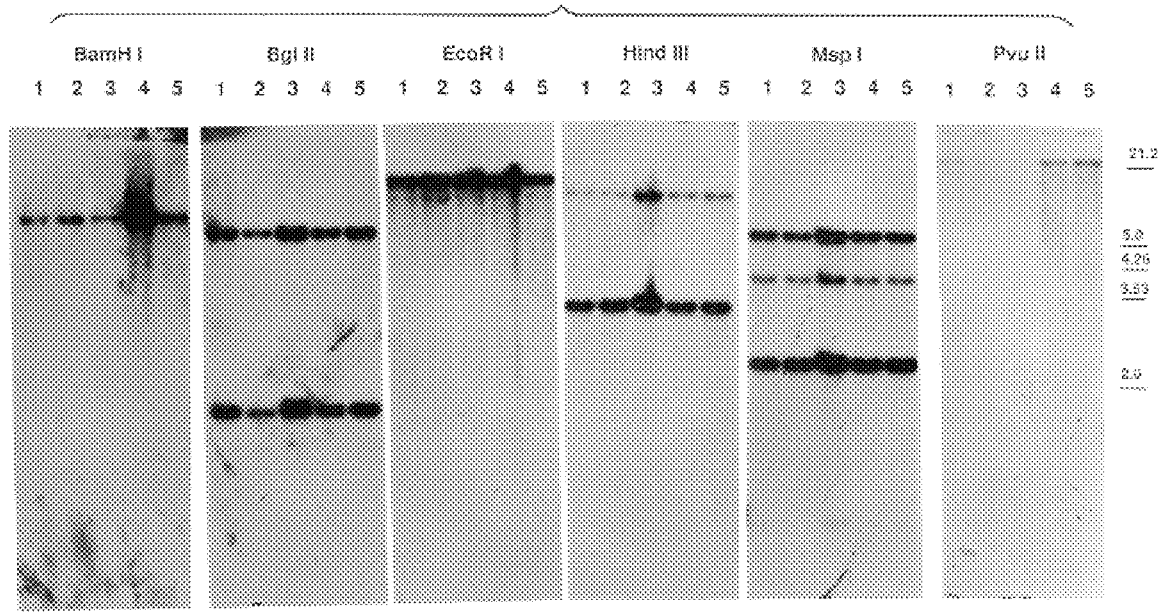

FIG. 18. Southern blot analysis of genomic DNA obtained from five different individuals. The DNAs were subjected to distinct restriction endonuclease digestions, blotted and hybridized with the human full length cDNA for the beta subunit. The numbers on the top indicate the different individuals while each panel corresponds to a different restriction digest. Size standards are indicated on the right.

FIG. 19A–19B. Amino acid sequence of the FcεRI human β subunit (SEQ ID NO:32) and alignment with rat (SEQ ID NO:33) and mouse (SEQ ID NO:34) β. Identical and non-identical amino acid residues are indicated by capital and lower case letters respectively. The identities and closely related exchanges are marked ˆ in the query line while the distantly related exchanges are denoted by a dot. Non-homologous exchanges shown no marking in the query line. The gaps are indicated by a hyphen. The transmembrane domains are underlined and the splice sites indicated with vertical bars.

Figure 20:
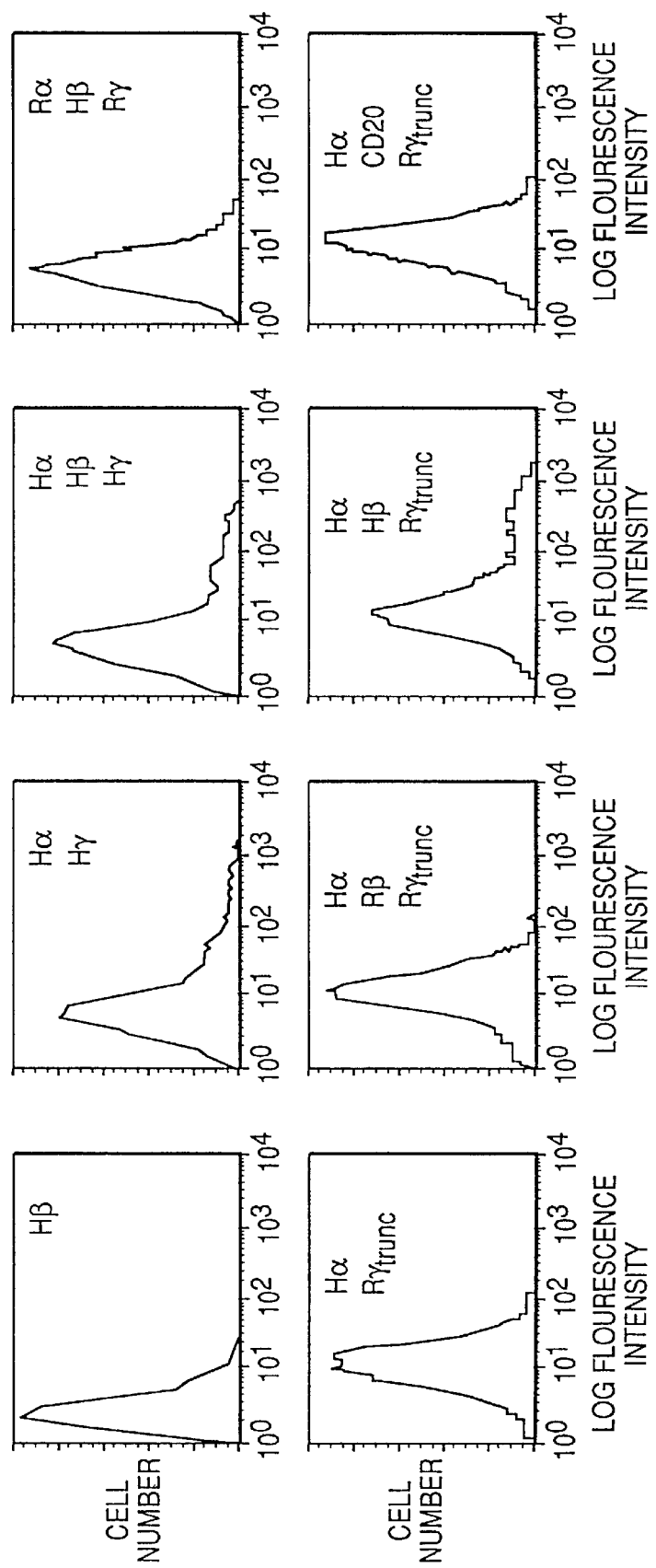

FIG. 20. Results of FACS analysis showing IgE binding in cells of a basophil line (KU812) transfected with various combinations of $Fc_\epsilon RI$ subunits.

Figure 21:
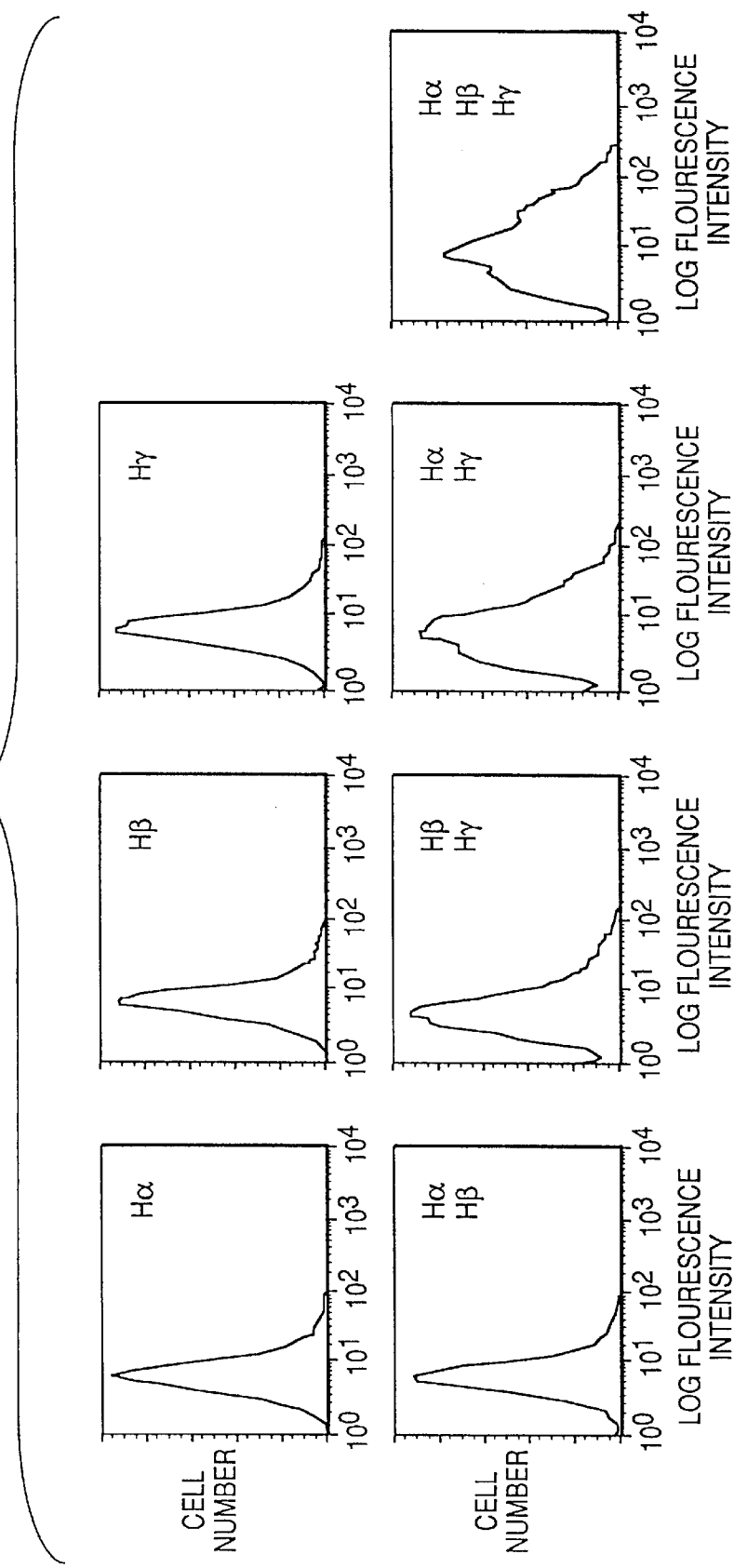

FIG. 21. Results of FACS analysis showing IgE binding in COS-7 cells transfected with various combinations of $Fc_\epsilon RI$ subunits.

DETAILED DESCRIPTION OF THE INVENTION

The present invention relates, in part, to DNA sequences which code for polypeptides corresponding to the subunits of human $Fc_\epsilon RI$.

More specifically, the present invention relates to DNA segments (for example, cDNA molecules) coding for polypeptides having amino acid sequences corresponding to the α, β and γ subunits of $Fc_\epsilon RI$. In one embodiment, the DNA segments have the sequence shown in FIGS. 1A–1C, 6A–6G, 9, or 14A–14Q 14 (SEQ ID NOs. 10, 22, and 24, 26, and 31, respectively), allelic or species variation thereof, or a unique portion of such a sequence (unique portion being defined herein as at least 15–18 bases). In another embodiment, the DNA segments encode the amino acid sequence shown in FIGS. 1A–1C, 6A–6G, 9, or 19A–19B (SEQ ID NO:11) (SEQ ID NOs. 23 and 24) (SEQ ID NO:27) or 19 (SEQ ID NOs. 11, 23, and 24, 27, and 32–34, respectively), or allelic or species variation thereof, or a unique portion of such a sequence (unique portion being defined herein as at least 5–6 amino acids).

Allelic or species variations are defined as substitutions, deletions, or other alterations in the nucleotide or amino acid sequence that do not eliminate the function of the subunits as defined herein. For some uses, the nucleotide sequence may be deliberately altered to, e.g., test the effects of such alteration on the function of the beta subunit, or to produce subunits which are inactivated for certain purposes.

In another embodiment, the present invention relates to polypeptides having amino acid sequences corresponding to the α, β and γ subunits of $Fc_\epsilon RI$. In one preferred embodiment, the polypeptides have amino acid sequences as shown in FIGS. 1A–1C, 6A–6G, 9, and 19A–19B, and 19 (SEQ ID NOs. 11, 23, and 24, 27, and 32–34, respectively), or allelic or species variations thereof, or a unique portion of such sequences (unique portion being defined herein as at least 5–6 amino acids).

In another embodiment, the present invention relates to a recombinant DNA molecule comprising a vector (for example—plasmid or viral vector) and a DNA segment coding for a polypeptide corresponding to the α, β or γ subunit of $Fc_\epsilon RI$, as described above. In a preferred embodiment, the encoding segment is present in the vector operably linked to a promoter.

In a further embodiment, the present invention relates to a cell containing the above described recombinant DNA molecule. Suitable host cells include procaryotes (such as bacteria, including *E. coli*) and both lower eucaryotes (for example yeast) and higher eucaryotes (for example, mammalian cells). Introduction of the recombinant molecule into the host cell can be effected using methods known in the art.

In another embodiment, the present invention relates to a method of producing the above described polypeptides, comprising culturing the above described host cells under conditions such that said polypeptide is produced, and isolating said polypeptide.

In a further embodiment, the present invention relates to a method of producing a functional $Fc_\epsilon RI$ receptor comprising introducing into a host cell DNA segments encoding the α, β and γ subunits of $Fc_\epsilon RI$ and effecting expression of said segments under conditions such that said receptor is formed.

The nucleic acid sequences and polypeptides according to this invention exhibit a number of utilities including but not limited to:

1. Utilizing the polypeptide or a fragment thereof as an antagonist to prevent allergic response, or as a reagent in a drug screening assay.
2. Utilizing the polypeptide as a therapeutic agent.
3. Utilizing the polypeptide for monitoring IgE levels in patients.
4. Utilizing the nucleic acid sequence to synthesize polypeptides which will be used for the above purposes.
5. Utilizing the nucleic acid sequences to synthesize cDNA sequences to construct DNA useful in diagnostic assays.

The present invention will be illustrated in further detail in the following examples. These examples are included for illustrative purposes and should not be considered to limit the present invention.

EXAMPLE 1

Isolation of cDNA Clones for the Alpha Subunit of Human $Fc_\epsilon RI$

RNA was extracted from FUB12 cells as described by Kishi, *Leukemia Research*, 9, 381 (1985) by the guanidium isothiocyanate procedure of Chirgwin, et al., *Biochemistry*, 18,5294 (1979) and poly(A) mRNA was isolated by oligo-dt chromatography according to the methods of Aviv, et al., *P.N.A.S. U.S.A.*, 69,1408 (1972). cDNA synthesis was performed as previously described kinet, et al., *Biochemistry*, 26,2569 (1987). The resulting cDNA molecules were ligated to EcoRI linkers, digested with the restriction enzyme EcoRI, size fractioned and ligated to λgt11 EcoRI arms as set forth in Young et al., *Science*, 222,778 (1983). The cDNA insert containing λgt11 DNA was packaged into bacteriophage lambda particles and amplified on Y1090. A total of 1.2×10⁶ independent cDNA clones were obtained. The cDNA library was plated onto Y1090 on 150 mm$_2$ plates (10⁵ per plate) and transferred to nitrocellulase filters. The cDNA library filters were screened by in situ hybridization using a nick translated cDNA fragment as in Kochan, et al., *Cell,* 44,689 (1986). The cDNA fragment was obtained from the rat Fc$_\epsilon$RI alpha cDNA corresponding to nucleotides 119–781. Positive plaques were identified, purified and the cDNA inserts were subcloned, using standard techniques, into the pGEM vectors (Promega Biotech, Madison, Wis.). The cDNA insert was mapped by restriction enzyme analysis, subcloned into derivatives of pGEM and sequenced using the dideoxynucleotide method of Sanger et al., P.N.A.S., 74,5463 (1977) following the GemSeq double strand DNA sequencing system protocol from Promega Biotech (Madison, Wis.). The DNA sequence was determined for both strands of the cDNA clone pLJ663 (nucleotides 1–1151) and for 300 bp of each end of clone pLJ 587 (nucleotides 658–1198). No discrepancy in DNA sequence between the two cDNA clones was observed.

The sequence for the human Fc$_\epsilon$RI alpha cDNA is presented in FIGS. 1A–1C and SEQ ID NO:10. The predicted amino acid sequence for the human Fc$_\epsilon$RI alpha polypeptide is shown below the nucleotide sequence and in SEQ ID NO:11, beginning with methionine at nucleotide 107–109 and ending with asparagine at nucleotide 875–877. The site of the predicted mature N-terminus was determined to be valine at nucleotide 182–184 according to the rules set forth by von Heijne, *Eur. Journal of Biochem:* 137,17; and *Nucleic Acid Research,* 14,4683 (1986).

Figure 2:
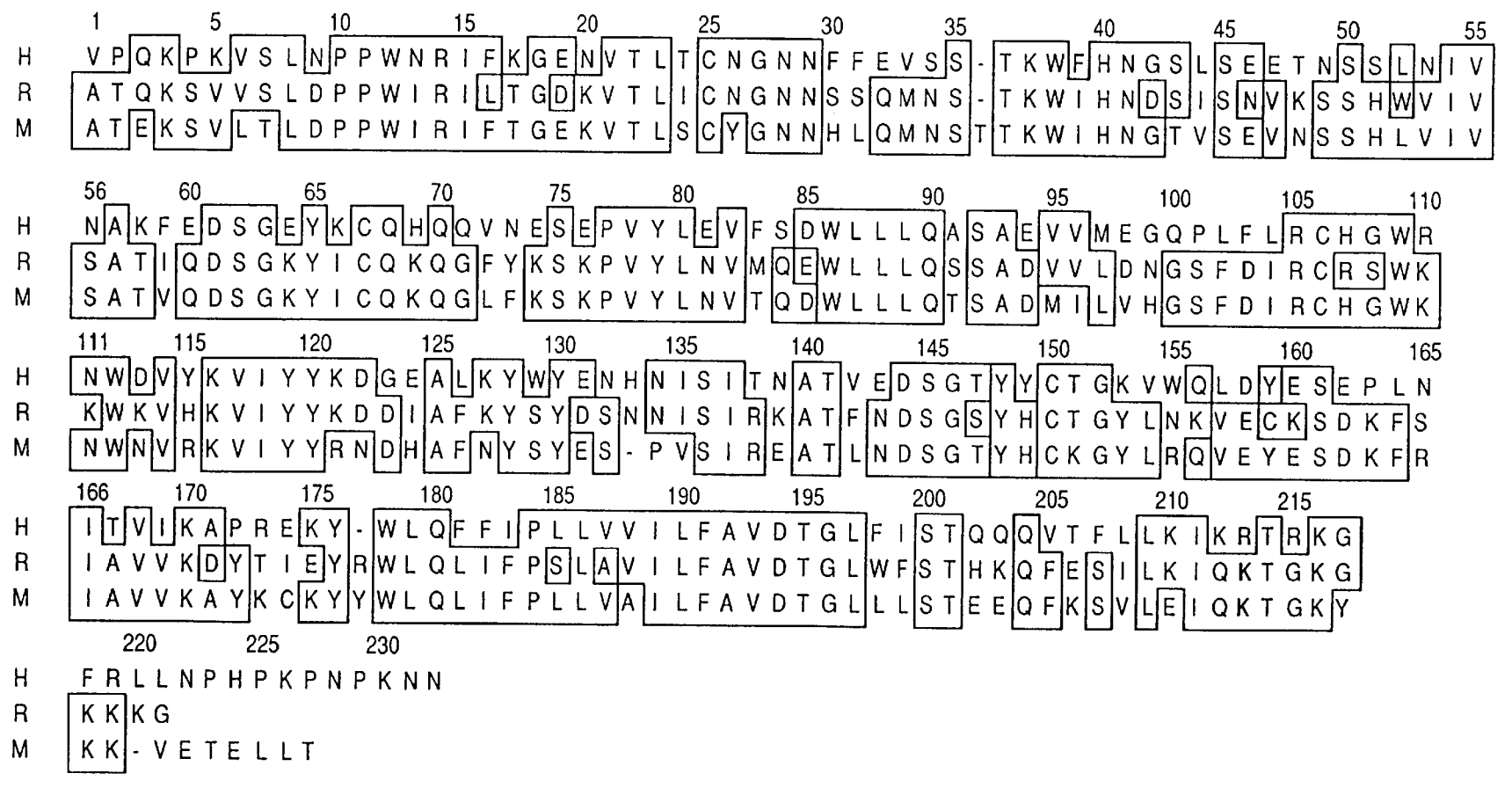

These results predict a 25 amino acid signal peptide. The rest of the cDNA sequence suggests that the human Fc$_\epsilon$RI alpha chain contains about 179–224 residues with 2 homologous domains (14 out of 25 residues are identical; residues 80–104 and 163–190), a 20-residue transmembrane segment (residues 205–224) and a 33 residue cytoplasmic domain containing 8 basic amino acids. Overall, there is 47% identity between the human and rat Fc$_\epsilon$RI alpha sequences, and 46% identity between the human FRI alpha and mouse FcGR alpha (FIG. 2 and SEQ ID NOs:12–14). The greatest level of homology is within the transmembrane region where 9 amino acids surrounding the common aspartic acid residue are identical.

EXAMPLE 2

Expression of the Human Fc$_\epsilon$RI Alpha Complete and Soluble Forms in Eukaryotic Cells Using the recombinant cDNA clone for the human Fc$_\epsilon$RI alpha chain, it is possible to introduce these coding sequences into an appropriate eukaryotic expression vector to direct the synthesis of large amounts of both a complete and soluble form of the alpha chain. For surface expression it may necessary that the alpha subunit be complexed with the beta or gamma subunit whereas for the eukaryotic expression of the secreted form of the alpha subunit this may not necessary. An appropriate vector for the purpose is pBC12BI which has previously been described in Cullen, (1987) *Methods in Enzymology* 152, Academic Press, 684. Construction of expression vectors coding for the complete alpha chain can be isolated as follows (FIG. 3): A unique BglII-SspI fragment (nucleotides 65–898) is isolated from pLJ663, the BglII end is filled in with DNA polymerase I Klenow fragment and ligated into pBC12BI which has been restricted with either HINDIII-BamHI or HindIII-SmaI (the ends are made blunt by filling in with DNA polymerase I Klenow fragment). The reason for attempting two different constructions is that the former contains a 3' intron while the latter does not. The presence or absence of introns may affect the levels of the alpha protein which are synthesized in cells transfected by these vectors. Construction of expression vectors coding for the soluble form of the alpha chain would be accomplished by introducing a termination codon at nucleotides 719–721 of the coding region in the alpha chain of the expression vectors noted above (pHAI, pHAII, FIG. 3). This would remove the putative transmembrane and cytoplasmic regions resulting in the synthesis of a secreted soluble form of the human alpha chain. Introduction of a termination codon is accomplished by oligonucleotide-directed site specific mutagenesis as outlined by Morinaga et al., *Bio. Tech.,* 2, 636 (1984). The sequence of the oligonucleotide will be 5' AAGTACTGGCTATGATTTTTTATC-CCATTG 3' (SEQ ID NO:1). The resulting expression vectors are pHASI and pHASII (FIG. 3) and these will direct the synthesis of a truncated alpha protein corresponding to amino acids 1–204. Expression of this protein in eukaryotic cells will result in synthesis of a mature, IgE binding protein encompassing amino acid residues 26–204.

The expression vectors are then introduced into suitable eukaryotic cells such as CHO or COS by standard techniques such as those set forth in Cullen, (1987), *Methods in Enzymology,* Academic Press, NY 152:684, in the presence of a selectable marker such as G418 or Methotrexate resistance. The selectable marker for Methotrexate resistance has an added advantage, since the levels of expression can be amplified by introducing the cells to higher levels of drugs. The synthesis of protein is monitored by demonstrating the ability of human IgE (or rat IgE) to bind to these cells (in the case of the complete alpha chain), or in the case of the soluble form of the alpha chain, to demonstrate that the protein secreted from these cells has the ability to bind IgE in the presence or absence of the beta.

EXAMPLE 3

Figure 4:
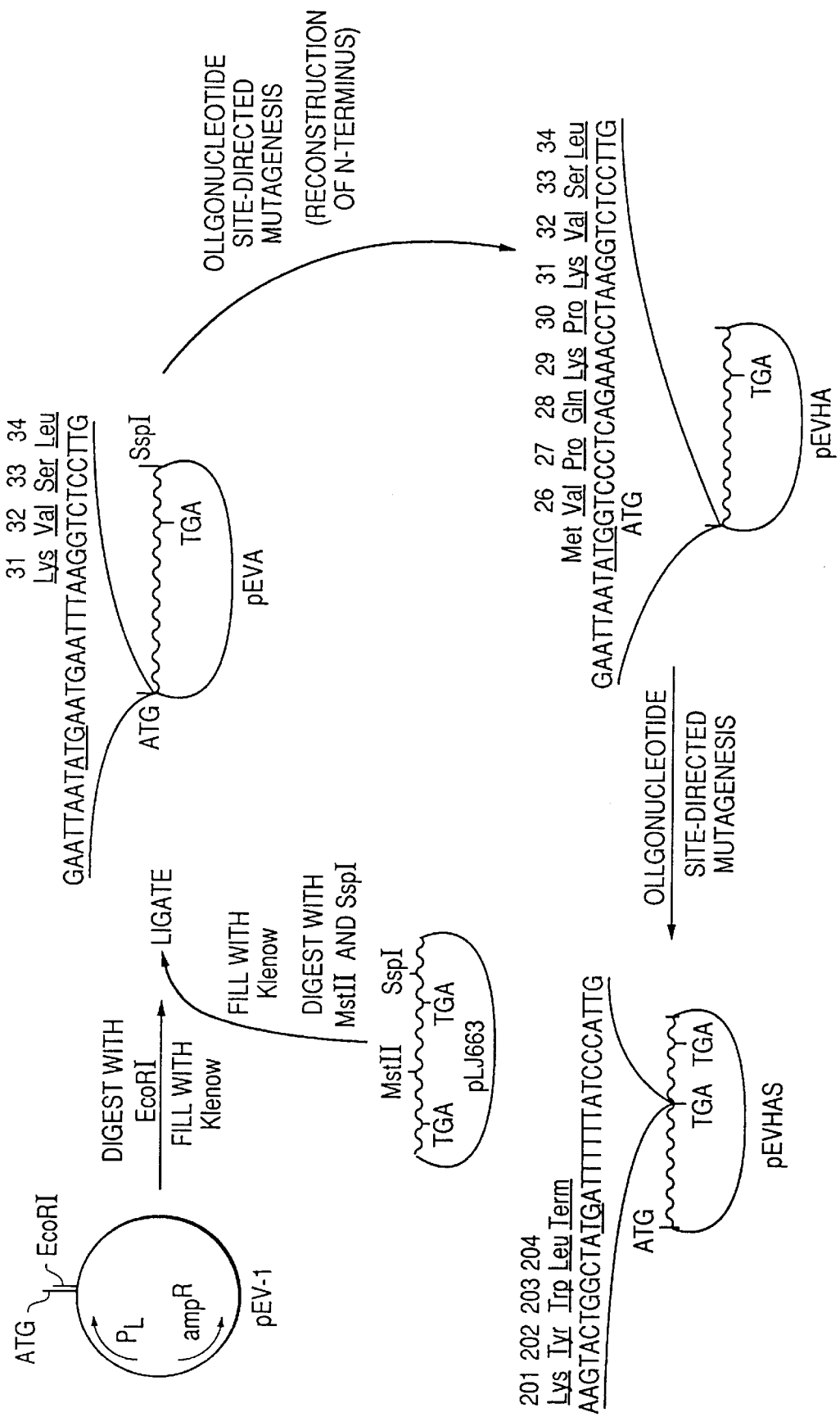
FIG. 4. A flow chart showing the construction of a prokaryotic expression vector which directs the synthesis of a soluble biologically active Fc$_\epsilon$RI alpha chain (which consists of amino acid residues 26–204) is presented.

Expression of the Human Fc$_\epsilon$RI Alpha Soluble Form in Prokaryotic Cells Using the recombinant cDNA clone for the human Fc$_\epsilon$RI alpha chain, it is possible to introduce these coding sequences into an appropriate prokaryotic expression vector to direct the synthesis of large amounts of a soluble (non-membrane bound) IgE binding polypeptide derived from the alpha chain. An appropriate vector for this purpose is pEV-1 which has been described by Crowl, et al., *Gene,* 38, 31 (1985). Construction of an expression vector coding for a soluble alpha chain can be isolated as set forth in FIG. 4: a unique MstII-SspI fragment (nucleotides 195–898 is isolated from pLJ663, the MstII end is filled in with DNA polymerase I Klenow fragment and ligated into pEV-1 which has been restricted with EcoRI, and the ends filled in with Klenow (FIG. 4, pEVA). The N-terminus of the mature alpha chain is reconstructed by oligonucleotide directed-site specific mutagenesis. The sequence of the oligonucleotide will be 5' GAATTAATATGGTCCCTCAGAAAC-CTAAGGTCTCCTTG 3' (SEQ ID NO:2). Introduction of this sequence into the expression vector pEVA aligns the Methionine residue of the EV-1 vector next to Valine-26 (the predicted mature N-terminus of the alpha chain) followed by amino acid residues 27–204 (pEVHA, FIG. 4). Reconstruction of the soluble form Fc$_\epsilon$RI alpha is accomplished by oligonucleotide site-directed mutagenesis. The sequence of the oligonucleotide will be 5'-AAGTACTGGCTATGATTTTTATCCCATTG-3' (SEQ ID NO:3). Introduction of this sequence into the expression vector, terminates polypeptide synthesis just prior to the start of the transmembrane region. The protein thus encoded by expression vector pEVHAS, should faithfully direct the synthesis of a soluble form of the alpha chain, corresponding to amino acid residues 26–204. This expression vector is then transformed into suitable hosts.

EXAMPLE 4

Isolation and Sequence Analysis of Peptides of the Beta Subunit of $FC_eRI$

Since repeated attempts to sequence intact β chains were unsuccessful, peptides were isolated from tryptic digests. Electroeluted β subunits from polyacrylamide gels were prepared as described (Alcaraz et al. (1987) Biochemistry 26:2569–2575). Tryptic peptides were separated by high-pressure liquid chromatography and sequenced as before (Kinet et al. (1987) Biochemistry 26:4605–4610). A peptide (no. 1) isolated from an initial digest had the sequence (SEQ ID NO:4) Tyr-Glu-Glu-Leu-His-Val-Tyr-Ser-Pro-ILe-Tyr-Ser-Ala-Leu-Glu-Asp-Thr. The same peptide from later digests showed an additional leucine at the $NH_2$ terminus and an arginine at the COOH terminus. The sequences of three other peptides, each isolated in substantial yields, are indicated in a subsequent figure.

EXAMPLE 5

Cloning and Sequencing of cDNA clones of the Beta Subunit of $Fc_eRI$

Figure 5:
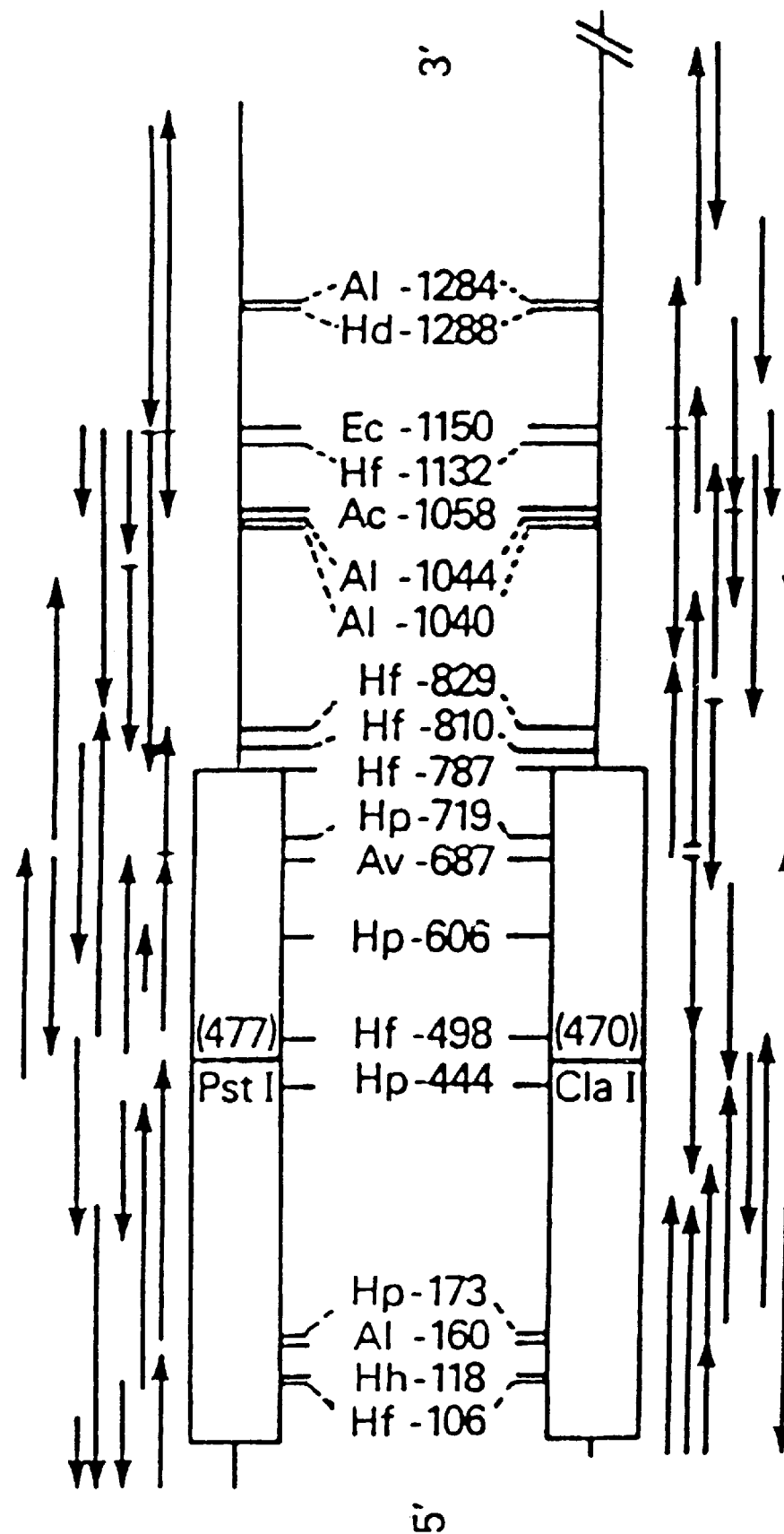
FIG. 5. Restriction maps for β cDNAs and strategy by which they were sequenced. The open rectangle indicates the sequence predicted to code for the β subunit; the lines indicate the 5' and 3' untranslated regions. The upper scheme shows the 1.5 kilobase (kb) clone containing a Pst I cleavage site. The lower scheme shows a 2.4-kb clone containing a ClaI cleavage site. The 3' region of the latter has been truncated as indicated by the slashes. Its untranslated portion was sequenced as completely as the rest of the clone. Restriction sites are indicated by vertical bars: Hf, Hinfl; Hh, Hha I; Al, Alu I; Hp, HphI; Av, Ava II; Ac, Acc I; Ec, EcoRI; Hd, HindIII. The horizontal arrows show the direction and extent of sequencing by the dideoxynucleotide chain-termination method.

RNA extracted from rat basophilic leukemia (RBL) cells by the guanidinium isothiocyanate method (Chirgwin et al. (1979) Biochemistry 18:5294–5299) was fractionated on an oligo (dT)—cellulose column (Maniatis et al. (1982) Molecular Cloning: A Laboratory Manual (Cold Spring Harbor Lab., Cold Spring Harbor, N.Y.) and used to construct a pUC-9 and a λgtll library (Maniatis et al. (1982) Molecular cloning: A Laboratory Manual (Cold Spring Harbor Lab., Cold Spring Harbor, N.Y.; Young and Davies (1983) Proc. Natl. Acad. Sci. USA 80:1194–1198). The initial sequence obtained for peptide 1 was used to construct two 26-mer oligonucleotides of 32-fold degeneracy: 5'-GGIGA(A/G) TA(G/C) ACATGIA(A/G) (C/T) TC (C/T) TCATA-3' (SEQ ID NO:5) and 5'-GGICT(A/G)TA(G/C) ACATGIA(A/G) (C/T)TC(C/T)TCATA 3' (SEQ ID NO:6). A λgtll library constructed from mRNA of RBL cells was screened with 1:1 mixture of these 15 oligonucleotides. Colonies were screened as in Kinet et al. (1987) Biochemistry 26:4605–4610, using oligonucleotides prepared on a model 380A automated DNA synthesizer (Applied Biosystems, Foster City, Calif.). Six positive clones gave similar restriction patterns. cDNA inserts were subcloned into pGEM-4 or pGEM-3Z and the resulting double-stranded DNA was sequenced with the GemseqRT sequencing system according to the method recommended by the supplier (Promega Biotec, Madison, Wis.). Twenty-mer oligonucleotides, corresponding to previously sequenced regions by this method, were used as primers to generate overlapping sequences otherwise difficult to obtain. In some instances, DNA sequencing was performed using Sequenase as recommended by the supplier (United States Biochemical, Cleveland). The clone containing the longest insert was sequenced according to the strategy shown in the upper portion of FIG. 5. The sequence predicts possible starting codons at nucleotides 46–48 and 55–57, which would yield a polypeptide of 246 or 243 residues, respectively (FIGS. 6A–6F and SEQ ID NO:22). The predicted $M_r$ of about 27,000 is some 20% less than the apparent molecular weight of β subunits when analyzed on polyacrylamide gels (Holowka and Metzger (1982) Mol. Immunol. 19:219–227). In addition, no in-frame stop codon was apparent upstream of the start codon. To rule out the possibility that the true start codon was still further 5', the cDNA library was rescreened with a restriction fragment (nucleotides 7–474) and with a synthetic oligonucleotide probe (nucleotides 3–32). Twenty-eight additional clones were isolated and their restriction patterns were examined. Twenty were similar to the original clones. Only six additional nucleotides at the 5' end (nucleotides 1–6, FIG. 6A were identified. Early termination was found in six clones, which otherwise had the same sequence through nucleotide 375 (FIG. 6G and SEQ ID NO:24). One 2.4-kb clone had cytidine 473 substituted with an adenine. This substitution abolishes the Pst I site and creates a new Cla I site at nucleotide 470. Also thereby, Ala-140 would become Asp-140 (FIG. 6B).

Finally, one clone extended ≈350 base pairs (bp) in the 5' direction. The junction with the sequence shown in FIG. 6A–6F was (SEQ ID NO:7) AATAAAACAAAAAAAAAAAAAATG, the last two nucleotides of the newly generated ATG corresponding to nucleotides 8 and 9 of the previous sequence. It is likely that this clone simply resulted from the ligation of two independent cDNAs. Screening of the pUC-9 library revealed three clones. However, the sequence of none of these extended 5' beyond nucleotide 84.

EXAMPLE 6

RNA Transfer Blotting

RNA transfer blotting was performed under high stringency using a Pst I fragment probe (nucleotides 1–474). Thirty micrograms of total RNA was run on a 1% agarose gel containing 2% formaldehyde and blotted to nitrocellulose filters (Maniatis et al. (1982) Molecular Cloning: A Laboratory Manual (Cold Spring Harbor Lab., Cold Spring Harbor, N.Y.). The filters were hybridized with a restriction fragment of the β cDNA (nucleotides 1–474) as described (Maniatis et al. (1982) Molecular Cloning: A Laboratory Manual (Cold Spring Harbor Lab., Cold Spring Harbor, N.Y.) and washed with 15 mM NaCl/1.5 mM sodium citrate at 65° C. RBL cells yielded two major bands at ≈2.7 kb and 1.75 kb with the upper band having about twice the intensity of the lower one. A minor band 1.2 kb was also noted. Negative results were obtained with a variety of cells that do not express high-affinity IgE receptors: the rat pituitary line GH3 (American Type Culture Collection no. CCL82.1), the rat glial cell line C6 (no. CCL107), the mouse Leydig cell line 1–10 (no. CCL83), and, notably, the mouse monocytic line J774 (no. T1B67) and the rat lymphoma "NTD" (Rivera et al. (1988) Mol. Immunol.)

EXAMPLE 7

In vitro Transcription and Translation cDNAs corresponding to the β subunit and various mutated or truncated forms thereof were subcloned into either pGEM-4 or pGEM-3Z transcript ion vectors (Promega Biotec). The β clone containing the Pst I site was transcribed in vitro with T7 RNA polymerase. Unlabeled RNAs were synthesized using either SP6 or T7 polymerase as recommended by the supplier. Capping reactions were performed as reported (Contreras et al. (1982) Nucleic Acids Res. 10: 6353–6362). After digestion of the template with RNase-free DNase I, the RNAs were purified further by extraction with phenol/chloroform and three precipitations from ethanol. The RNA was then translated with a micrococcal nuclease-treated lysate of rabbit reticulocytes in the presence of [$S^{35}$] methionine as recommended by the supplier (Promega Biotec). The products of translation were diluted 1:1 with 20 mM detergent {3-[3-(cholamidopropyl)dimethylammio]-1-propane sulfonate in borate-buffered saline (pH 8) containing 30 µl of aprotinin per ml, 175 µg of phenylmethyl-sulfonyl fluoride per ml, 10 µg of leupeptin per ml, and 5 µg of pepstatin per ml and immunoprecipitated with monoclonal antibodies as described (Rivera et al. (1988) Mol. Immunol.). The unfractionated translated material showed a major component at $M_r$ 32,000 compared to the control from which the RNA had been omitted or an alternative RNA (brome mosaic virus) had been substituted.

The isolation of antibodies was as follows: *Escherichia coli* transformed with an expression vector containing the desired restriction fragments (Crowl et al. (1985) Gene 38:31–38; Portnoy et al. (1986) J. Biol. Chem. 261:14697–14703) were cultured and induced, and the fraction enriched for the recombinant protein was prepared as described (Portnoy et al. (1986) J. Biol. Chem. 261: 14697–14703). After separation on polyacrylamide gels in sodium dodecyl sulfate ($NaDodSO_4$) the transformant-specific protein was eluted and used to immunize rabbits. Approximately 100 µg of protein was injected in complete Freund's adjuvant; this was followed by a booster injection of 25 µg of protein in incomplete adjuvant. The isolation and characterization of monoclonal anti-β antibodies mAbβ (JRX) and mAbβ(NB) (the latter, was obtained from David Halowka, Cornell University) have been described (Rivera et al. (1988) Mol. Immunol. 25:647–661).

The monoclonal anti-β antibodies mAbβ(JRk) and mAbβ (NB) (Rivera et al. (1988) Mol. Immunol.) (FIG. 7A, lanes 2 and 3)—but not an irrelevant antibody (lane 5)—precipitated radioactive material, which on polyacrylamide gels in $NaDodSO_4$ showed a major band at $M_4$ 32000. This band had the identical mobility as the upper band of the doublet precipitated by mAbβ(JRK) from an extract of labeled RBL cells (lane 1). Although not seen well in the reproduction, the autoradiogram showed that the material synthesized in vitro also contained the lower molecular weight component seen the in vivo synthesized 0 chains. The mobility of the in vitro synthesized protein was unaltered by reduction as has been previously observed with the β subunit. The clone containing the Cla I site (which lacks the first ATG codon) led to the synthesis of a protein whose mobility on gels was indistinguishable from that for the clone containing the Pst I site. On the other hand, an aberrant clone containing the newly generated ATG (above) induced the synthesis of a somewhat larger protein with an apparent $M_r$, of 33,500. In vitro translation of a transcript coding for the $NH_2$-terminal 21 amino acids of the β subunit led to a product precipitable by mAbβ(JRK) (FIG. 7B).

EXAMPLE 8

Expression of the Beta Subunit of $Fc_\epsilon RI$ in *E. coli*

Two HinfI fragments (A, nucleotides 106–498; B, nucleotides 499–787) were individually subcloned into an *E. coli* expression vector, and extracts were prepared from the induced cultures. The results of one immunoblotting experiment are shown in FIG. 7C. The material extracted from the bacteria transformed with a vector containing the HinfI fragment B exhibited a $M_r$ 14,000 component reactive with mAbβ(NB) but not with mAbβ(JRK) (FIG. 7C, lane 3). The extract from the transformants containing the more $NH_2$-terminal HinfI fragment A (residues 17–148) reacted with neither antibody (compare with above). Rabbit antibodies generated by fragment A reacted on immunoblots with purified receptors exactly at the position where the two monoclonal anti-β antibodies reacted (FIG. 7D, lanes 1–3) and quantitatively precipitated intact $^{125}$I-labeled IgE-receptor complex from unfractionated detergent extracts of RBL cells.

EXAMPLE 9

Biosynthetic Incorporation

Biosynthetic incorporation of labeled amino acids and monosaccharides was described (Perez-Montfort et al. (1983) Biochemistry 27:5722–5728). The purification and analysis on gels and by immunoblotting of the IgE-receptor complexes have also been described (Rivera et al. (1988) Mol. Immunol.).

By using biosynthetic incorporation of two different amino acids labeled distinguishably, their ratio in the subunits of the receptor (Table 1, right part) was determined. The ratios of four distinctive amino acids to each other was in satisfactory agreement with the ratios predicted from the β cDNA clone (Table 1, right part, columns 1–3). Because the cDNA for the β subunit predicts three potential glycosylation sites, a double-labelling experiment using ($^3$H] mannose and ($^{35}$S) cysteine was also performed. Based on the relative carbohydrate data reported for the α subunit (Kaneilopoulos et al. (1980) J. Biol. Chem. 255:9060–9066) and correcting them on the basis of the peptide molecular weight for this chain predicted from the cDNA, it was calculated that the α subunit contains ≈20 mol of mannose per mol. It was therefore possible to determine the mannose/cysteine ratio in the β subunit from the double-labeling experiment. The results showed only 0.05 mol/mol of cysteine or 0.3 mol/mol of the β subunit (Table 1, right part, column 4).

TABLE I

Amino Acid composition of β Subunits cDNA versus compositional analysis for the β subunit

|  | Asx | Thr | Ser | Glx | Pro | Gly | Ala | Val | Met | Ile | Leu | Tyr | Phe | His | Lys | Arg | Cys | Trp |
|---|---|---|---|---|---|---|---|---|---|---|---|---|---|---|---|---|---|---|
| Deduced from β cDNA | 20 | 12 | 23 | 24 | 15 | 12 | 19 | 17 | 4 | 15 | 36 | 9 | 12 | 1 | 8 | 8 | 6 | 2 |
| Direct analysis* Double-labeling studies+ | 22 | 13 | 22 | 27 | 13 | 19 | 18 | 14 | 4 | 13 | 31 | 7 | 10 | 2 | 10 | 10 | 5 | ND | cDNA versus incorporation data

|  | Met/His | Cys/His | Cys/Trp | Man/Cys |
|---|---|---|---|---|
| Deduced from β cDNA | 4 | 6 | 3 | — |
| Direct analysis* Double-labeling studies+ | 4.2 | 5.1 | 2.5 | 0.05 |

*The mol % of each amino acid as reported by Alcaraz et al. ((1987) Biochemistry 26:2569–2575) was multiplied by 241 - the number of residues, excluding tryptophan - predicted from the cDNA.
ND, not determined.
+IgE-receptor complexes were purified from RBL cells incubated with a mixture of two precursors labeled with differentiable radioisotopes. The subunits were separated on a polyacrylamide gel. The gel was sectioned into 2-mm slices, extracted, and assayed for radioactivity by scintillation spectroscopy. The ratio of cpm of $^{35}S/^{3}H$ was individually calculated for α, β, and γ subunits. The ratio in the α, subunit is proportional to the known molar ratio of the $^{35}S$-labeled and $^{3}H$-labeled residues in the α subunit. Hence, the corresponding ratio in the β subunit (and the γ subunit) predicts the ratio of the same residues in the latter subunits.

EXAMPLE 10

Sequence Characteristics

There is ample evidence that the cDNAs that were isolated code for the β subunit. (i) In vitro transcription of the cDNA and translation of the derived mRNA produce a protein whose apparent molecular weight on gel electrophoresis is indistinguishable from that of authentic β chains (FIG. 7A). (ii) The cDNA accurately predicts the sequence of four peptides isolated from a tryptic digest of β chains (FIGS. 6A–6F and SEQ ID NO:22) and a composition that agrees well with direct analyses and biosynthetic incorporations (Table I). (iii) Two monoclonal antibodies reactive with discrete epitopes on the β subunit (Rivera et al. (1988) Mol. Immunol.,) precipitate the protein synthesized in vitro from the cloned cDNA (FIG. 7A), and one of them reacts with a fragment of the protein expressed in E. coli (FIG. 7C). (iv) Polyclonal antibodies raised against a fragment of the β subunit synthesized by E. coli transformants react with β chains on immunoblots (FIG. 7D) and with IgE-receptor complex in solution.

The nucleotide sequence at the 5' end of the cloned cDNA (clone 1) does not in itself define the start of the open reading frame unambigously. There is no leader sequence and no "in frame" stop codon preceding the presumptive start codon. In addition, the molecular weight deducted from the cDNA ($M_r$ 27,000) is substantially lower than the one observed on NaDodSO$_4$ gels ($M_r$ 32,000), although the β subunit is not glycosylated. Therefore, it was possible that the start codon had been missed. Nevertheless, the aggregate data provide strong evidence that the full coding sequence for the β subunit has been recovered. (i) Extensive attempts failed to reveal cDNAs in either of two separate libraries with a more extended 5' sequence. (ii) The major species generated by 5' extension studies terminated precisely at the point at which most of our clones started. (iii) The second ATG codon at the 5' end meets the consensus characteristics of known initiation sites (Kozak (1987) Nucleic Acids Res. 15:8125–8148). That it is preceded by a nearby 5' ATG codon is uncommon, but not rare (Kozak (1987) Nucleic Acids Res. 15: 8125–8148), and has been observed for the human α subunit (Shimizu et al. (1988) Proc. Natl. Acad. Sci. USA 85:1907–1911; Kochan et al. (1988) Nucleic Acids Res. 16:3584). (iv) As already noted, in vitro translation of an mRNA transcribed from the cDNA containing only the second ATG codon gives a polypeptide indistinguishable in length from the authentic β chains. An aberrant clone containing a start codon 48 nucleotides 5' to the presumed start codon directed the in vitro synthesis of a polypeptide with an apparent molecular weight appropriately greater than that of the β subunit. Therefore, the correspondence in apparent molecular weight between authentic β chains and the protein synthesized in vitro from clone 1 is meaningful. The RNA transfer blotting data show an mRNA of ≈2.7 Kb, precisely what would be anticipated from the cDNA that was sequenced (FIGS. 6A–6F), given a poly (A) tail of ≈200 nucleotides. In the discussion that follows it is assumed that the β chain beings with the methionine residue coded for by the second ATG and is, therefore, 243 residues long.

Only a single clone containing the Cla I restriction site was observed among the 37 clones analyzed. This clone likely resulted from a single base mutation during the cloning and is unlikely to represent a normally occurring mRNA. Conversely, six clones showing the deleted sequence (FIG. 6B) were observed and likely reflected an authentic species of mRNA. If translated, it would code for a $M_r$ 14,000 protein with only a single transmembrane segment.

The sequence of the β subunit contains potential sites for N-linked glycosylation at residues 5, 151, and 154. However, past and new incorporation data give no evidence for carbohydrate in the β subunit (Perez-Montfort et al. (1983) Biochemistry 27:5722–5728; Holowka and Metzger (1982) Mol. Immunol. 19:219–227; and Table I). The sequence shows no unusual features or homology to previously reported sequences, in particular to those associated with Fc receptors or with Fc binding factors.

A hydropathicity analysis suggests that the β subunit crosses the plasma membrane four times (FIG. 8). The hydrophilic NH$_2$ and COOH terminus would therefore be on the same side of the membrane. Expression of fragments of the β cDNA indicate that mAbβ-(NB) reacts within amino acids residues 149–243 (FIG. 7C) and that mAbβ(JRK) reacts with fragment containing residues 1–21 (FIG. 7B). Because neither antibody reacts appreciably with intact cells but both react strongly with cell sonicates, the combined results are consistent with the $NH_2$ and COOH terminus being on the cytoplasmic side of the plasma membrane.

Earlier studies had suggested that the β chain contained a $M_r$-20,000 "β," domain resistant to proteolysis while membrane bound (Holowka and Metzger (1982) Mol. Immunol. 19:219–227). This portion also contained those residues that were modified by an intrabilayer labeling reagent (Holowka and Metzger (1982) Mol. Immunol. 19:219–227; Holowka et al. (1981) Nature (London) 289:806–808) and became linked to the β and/or γ subunit when chemical crosslinking reagents were used (Holowka and Metzger (1982) Mol. Immunol. 19:219–227) and to the γ subunit when spontaneous disulfide linkage between the β and $γ_2$, subunits occurred (Kinet et al. (1983) Biochemistry 22:5729–5732). The remainder, "$β_2$,", appeared to contain the serine residues that became phosphorylated in situ (Perez-Montfort et al., (1983) Biochemistry 22:5733–5737; Quarto and Metzger (1986) Mol. Immunol. 23:1215–1223) but has never been positively identified as a discrete fragment. The sequence predicted by the cDNA for the β subunit suggest that part or all of either the $NH_2$-terminal 59 residues or the COOH-terminal 44 residues, or of both, is cleaved off to generate the β1 fragment.

EXAMPLE 11

Contransfection Experiments

The full-length coding sequences of the α and the β subunits were cotransfected in COS 7 cells by using a vector for transient expression. No IgE-binding sites were expressed at the surface of transfected cells.

Studies of the receptor with low affinity for IgE on macrophages revealed a component that could be chemically crosslinked to the IgE-binding portion and that had an apparent molecular weight similar to the β subunit of the high-affinity receptor (Finoloom and Metzger (1983) J. Immunol. 130:1489–1491). The peptides generated from this component by protease digestion appeared to differ from those released from β subunits, but it raised the possibility that other Fc receptors also contained β-like subunits that had heretofore escaped detection (Rivera et al. (1988) Mol. Immunol.). Evidence for this from RNA transfer blot experiments conducted at high stringency is not available. In particular, J774 cells are known to contain Fcγ receptors whose immunoglobul in-binding chain shows considerable homology to the α chain of the high-affinity receptor for the IgE (Kinet et al., (1987) Biochemistry 26: 4605–4610). However, it was not possible to detect mRNA for β chains by the methods that were employed. Similarly, NTD lymphoma cells gave negative results even though they have Fcγ receptors and show a low molecular weight component that reacts with mAbβ(JRK) on immunoblots.

EXAMPLE 12

Isolation and Sequence Analysis of Peptides of the Gamma Subunit of $Fc_εRI$ $Fc_εRI$ was purified by affinity chromatography using TNP-lysine beads as described in G. Alcaraz et al., Biochemistry 26:2569–2575 (1987). The eluate was applied to sepharose 4B beads coupled by cyanogen bromide to monoclonal anti-β (JRK) (J. Rivera et al., Mol Immunol. 25:647–661 (1988)). After washing the beads with 2 mM CHAPS in borate buffered saline at pH8, the bound material was eluted at 65° C. with 0.1% sodium dodecyl sulfate, phosphate buffered saline, pH 6.5. The subunits from $Fc_εRI$ were then separated by HPLC size chromatography, the β and γ containing fractions recovered, reduced, alkylated and digested with trypsin (J.-P. Kinet et al., Biochemistry 26:4605–4610 (1987)). The resulting peptides were separated by HPLC reverse phase chromatography as in J.-P. Kinet et al, Biochemistry 26:4605–4610 (1987). The chromatograms from the β and γ digests were compared and the non-overlapping q peptides were sequenced (J.-P. Kinet et al., Biochemistry 26: 4605–4610 (1987)).

EXAMPLE 13

Cloning and Sequence of cDNA Clones of the Gamma Subunit of $FC_εRI$

Oligonucleotide probes were synthesized according to the sequences of peptide 3 (residues 41 to 47 of SEQ ID NO:27) and of peptide 4 (residues 54 to 62 of SEQ ID NO:27). The sequences were GA(A/G)AA(A/G)TCIGA(T/C) GCTCTCTA and (SEQ ID NO:8) AA(T/C)CA(A/G) GA(A/G)ACITA(T/C)GA(A/G)ACI(T/C)TIAA (SEQ ID NO:9). The methods used to screen the λgt11 library, to purify, subclone and sequence the positive clones are known in the art (J. P. Kinet et al., Biochemistry 26:4605–4610 (1987)). Peptide 3 and peptide 4 were also synthesized using a peptide synthesizer ABI 431A. The purity of the synthetic peptides was assessed by HPLC reverse phase chromatography, amino acid composition and mass spectroscopy. The peptides were conjugated either to ovalbumin using m-Maleimidobenzoyl-N-hydroxysuccinimide ester (F. T. Liu et al., Biochemistry 18:690–697 (1979)) at a molar ratio of 5:1 or to sepharose 4B with cyanogen bromide. Rabbits were immunized with the ovalbumin-conjugated peptides, the antisera collected and the antipeptide antibodies purified by affinity chromatography using sepharose 4B conjugated peptides. The antipeptide antibodies were tested for reactivity with the γ subunit of $Fc_εRI$ by Western blotting and for their ability to immunoprecipitate $^{125}$I-IgE receptor complexes (J. Rivera et al., *Mol. Immunol.* 25:647–661 (1988)). The nucleotide sequence of the γ subunit of rat $Fc_εRI$ (SEQ ID NO:26) obtained using the method of this invention, as well as the amino acid sequence (SEQ ID NO:27) that it predicts, are shown in FIG. 9. The nucleotide sequence for the γ subunit of the human $Fc_εRI$ is shown in SEQ ID NO:35 (Küster et al., 1990).

In order to isolate and characterize the cDNA for the γ subunit, cDNAs for the $Fc_εRI$ γ subunit were isolated from a λgt11 library prepared from rat basophilic leukemia (RBL) cells (J. P. Kinet et al., Biochemistry 26:4605–4610 (1987)) using oligonucleotide probes. Four peptide sequences were identified in a tryptic digest of the $Fc_εRI$ γ subunits, and two of the peptides were used to synthesize two oligonucleotide probes (FIG. 9). The library was screened in duplicate with these two probes and overlapping plaques identified. Three discrete plaques were purified, subcloned and found to contain similar inserts of 0.6 to 0.7 kilobases (Kb).

FIG. 9 shows the complete nucleotide sequence (SEQ ID NO:26) of the γ cDNA, the deduced amino acid sequence (SEQ ID NO:27) and the position in the sequence of the four original tryptic peptides. Analysis of the sequence (FIG. 10C) indicates an N-terminal hydrophobic signal peptide of 18 residues and a putative transmembrane domain separating a short extracellular portion of 5 residues from an intracytoplasmic domain. As predicted by earlier studies, the N-terminal processed—subunit contains two cysteines, no methionine and no tryptophan residues (G. Alcaraz et al., Biochemistry 26:2569–2575 (1987)). Compositional analysis suggested that the γ subunit might contain one histidine residue (G. Alcaraz et al., Biochemistry 26:2569–2575 (1987)). However, biosynthetic dual labeling studies of the receptor using $^{35}$S methionine and $^3$H histidine, clearly indicated that no trace of histidine was incorporated into the receptor-associated γ subunit. Since the open reading frame derived from three independent clones, each predicts a histidine six residues from the C-terminal end, it is expected that the γ subunit undergoes a C-terminal processing which clips off the histidine-containing segment. Furthermore, because the peptide immediately preceding this histidine was recovered (FIG. 9), the C-terminal segment must be cleaved after Lys 63. The predicted molecular weight of the fully processed γ would therefore be 7139 Da, in close agreement with values obtained for the purified reduced γ on sodium dodecyl sulfate—urea gels (G. Alcaraz et al, Biochemistry 26:2569–2575 (1987)).

Polyclonal antipeptide antibodies to a heptamer and to a nonamer peptide of the γ subunit (FIG. 9) were prepared and tested for reactivity with IgE receptor complexes for RBL cells. Both purified antipeptide antibodies reacted in a Western blot assay with the unreduced dimer and the reduced monomer of partially purified γ subunits. In addition, both antibodies quantitatively precipitated receptor-bound $^{125}$I-IgE, either from an extract of RBL cells or from a preparation of partially purified receptors. Taken together, these results leave no doubt that the cDNAs isolated according to the present invention code for the γ subunit of Fc$_\epsilon$RI.

EXAMPLE 14

Expression of Receptor

In order to achieve expression of the receptor on the surface of COS 7 cells, the coding region of the α, β, and γ cDNAs were first subcloned separately into the SV 40 promoter-driven expression vector pSVL, prior to transfection into the COS-7 cells. The 810 bp EcoRI-Sty I restriction fragment of the α cDNA, the 965 bp EcoRI-EcoRV restriction fragment of the β cDNA and the 300 bp EcoRI-Dde I restriction fragment of the γ cDNA were subcloned separately into the Sma I site of the transient expression vector pSVL (Pharmacia, Uppsala, Sweden). These restriction fragments individually contained the entire coding sequence of the appropriate subunit and variable portions of untranslated sequences. The only foreign sequence was the starting EcoRI recognition sequence which belonged to the initial linker. Cultured COS7 monkey kidney cells were then transfected with 40 μl of DNA by the standard calcium phosphate precipitation technique (L. Davis et al., in Basic Methods in Molecular Biology, ed. L. Davis, Elsevier, New York (1986)). After 48 hrs, the transfected cells (FIGS. 11A and 11B), as well as RBL cells (FIGS. 11C and 11D), were examined for surface expression of IgE binding by an IgE rosetting assay. The cells (5×10$^6$ cells/ml) were incubated at room temperature with (FIGS. 11B and 11D) or without (FIGS. 11A and 11C) μg/ml of non-specific rat IgE for 30 min and then with 5 μg/ml of anti-DNP-IgE (F. T. Liu et al., J. Immunol. 124:2728–2736 (1980)). The cells were then rosetted with ox red blood cells that had been modified with 2,4,6-trinitrobenzene sulfonic acid according to a known method (M. Rittenberg et al., Proc. Soc. Exp. Biol. Med. 132:575–581 (1969)). The results are shown in FIGS. 11A–11D. FIG. 11A shows IgE-binding activity expressed by cells cotransfected with the α, β and γ subunits. Virtually all RBL cells, used as a positive control, formed rosettes (FIG. 11C). The rosettes were completely inhibited by preincubation of the cells with rat IgE (FIGS. 11B and D) but not with human IgE (not shown). This coincides with the species specificity for the rat Fc$_\epsilon$RI (A. Kulczycki et al., J. Exp. Med. 139:600–616 (1974)).

In order to study the requirements for surface expression of IgE-binding activity, the cells were transfected with different combinations of the cDNAs for the three subunits, as shown in Table 2.

COS-7 cells were transfected with different combinations of cDNAs for the three subunits of Fc$_\epsilon$RI (FIG. 11). The rosetting assay was performed for each transfection shown in Table 2. The assessment of the mRNA by Northern blotting was performed one time only (on 2×10$^7$ cells). Inhibitor was added to the cells in the experiments marked by an asterisk in Table 2 (50 μg/ml of non-specific rat IgE was added to the cells 30 minutes prior to the addition of the specific mouse anti-DNP IgE).

TABLE 2

Transfection Experiments

| Cells | Transfections cDNA | No. | Expression Receptor mRNA | Ige Binding (rosettes/cells counted) |
|---|---|---|---|---|
| COS 7 | 0 | 9 | 0 | 0/12,948 |
|  | α | 2 | α | 0/4,050 |
|  | αβ | 2 | αβ | 0/3,504 |
|  | α | 4 | α | 0/8,030 |
|  | β | 1 | β | 0/2,069 |
|  | αβ | 29 | αβ | 920/41,238 |
|  | αβ | 4 | αβ | 0/7,542* |
| RBL | 0 | — | αβ | "100%" |

*Experiments where inhibitor was added.

Table 2 summarizes the data derived from all the transfection experiments performed as described up to here. The success rate of the transfection experiments has improved since that data was collected so that there is now routinely achieved 5±2% expression of IgE binding when α, β and γ are simultaneously cotransfected.

Successful transfection was achieved for all combinations, as assessed by Northern blotting, but rosette forming cells were only detected after cotransfection of the full set of the cDNAs. These results indicate that the β and γ subunits are required for surface-expression of the IgE-binding α subunit. It is further indicated that only the fully assembled receptor reaches the plasma membrane. This phenomenon has also been observed in other systems (M. McPhaul et al., Proc. Natl. Acad. Sci. USA 83:8863–8867 (1986); Y. Minami et al., Proc. Natl. Acad. Sci. USA 84:2688–2692 (1987)) and may be generally applicable to polymeric membrane proteins.

The easy dissociability of β and γ, from α (B. Rivnay et al., Biochemistry 21:6922–6927 (1982)) has raised persistent uncertainty about whether conceptually, γ$_2$, and β should be considered as subunits of Fc$_\epsilon$RI or as "receptor associated" proteins. (An example of the latter is the CD3 complex which associates with the antigen receptor on thymus-derived lymphocytes (H. Clevers et al., Ann. Rev. Immunol. 6:629–662 (1988)). The subunit model for Fc$_\epsilon$RI has been favored, for example, on the basis of the coordinate biosynthesis and catabolism of α, β and γ, (R. Quarto et al., Molec. Immunol. 22: 1045–1052 (1985)). The new data on transfected cells obtained by the present invention provides the strongest evidence yet obtained that αβγ2 is the minimal structure for Fc$_\epsilon$RI.

The present model for the tetrameric Fc$_\epsilon$RI receptor is illustrated in FIGS. 12A–12D and SEQ ID NOS:28–30. In this model each of the 589 amino acid residues of which the expressed receptor is composed is shown as a circle. In the diagram, the exterior of the cell would be at the top, the plasma membrane in which the receptor is embedded would be in the middle, and the interior of the cell towards the bottom. Each of the polypeptide chains (the α, SEQ ID NO:28, on the left, the β, SEQ ID NO:29, chain in the middle and the two γ, SEQ ID NO:30, chains on the right) contains one or more transmembrane segments.

The α chain (SEQ ID NO:28) is believed to contain two intrachain disulfide loops, and the sequences of these loops show considerable homology with immunoglobulins (J. P. Kinet et al., Biochemistry 26:4605 (1987); A. Shimizu et al, Proc. Natl. Acad. Sci. USA 85:1907 (1988); J. Kochan et al., Nucleic Acids Res. 16:3584 (1988)). Thus, the α subunit is another member of the immunoglobulin superfamily (A. Williams et al., Ann. Rev. Immunol. 6:381 (1988)). The extracellular and transmembrane segments of the α chain show considerable homology with the immunoglobulin binding chain of Fc receptors that bind IgG (J. Ravetch et al., Science 234:178 (1986)), but the intracellular cytoplasmic tail is quite different. The carbohydrate residues that are covalently attached to the extracellular portion of the α chain are not indicated in FIGS. 12A–12D. There are seven potential sites for N-linked carbohydrates (J. P. Kinet et al., Biochemistry 26:4605 (1987); A. Shimizu et al., Proc. Natl. Acad. Sci. USA 85:1907 (1988)), but which of these that are actually used by the cell remains to be determined. Studies show that the carbohydrate is not essential for the binding of IgE by this chain (B. Hempstead et al, J. Biol. Chem. 256:10717 (1981)).

The β chain (SEQ ID NO:29) contains four transmembrane segments (J. P. Kinet et al., Proc. Natl. Acad. Sci. USA 85:6483 (1988)) and previous studies with monoclonal antibodies (J. P. Kinet et al., Proc. Natl. Acad. Sci. USA 85:6483 (1988); J. Rivera et al., Mol. Immunol. 25:647 (1988)) show that the amino- and carboxyltermini which are respectively 59 and 43 residues long, protrude from the cytoplasmic face of the plasma membrane. Similarly, the γ chains (SEQ ID NO:30) have an extensive intracellular extension but only very limited exposure to the exterior.

According to the general model, the putative transmembrane domains of the individual subunits are predicted from their respective hydropathicity plots (see FIGS. 10A–10C, wherein a net free energy of >20 kcal/mol for transfer to water suggests a transmembrane segment or a leader peptide (D. Engelman et al., Ann. Rev. Biophys. Biophys. Chem. 15:321–353 (1986)). These plots suggest one, four and one hydrophobic domains for the α, β and each γ, respectively (i.e., seven transmembrane domains for the entire receptor). Members of a family of receptors interacting with G proteins also contain seven transmembrane domains (I. Herskowitz et al., Cell 50:995–996 (1987)). This family includes β and α adrenergic, muscarinic receptors and rhodopsin. Although no sequence homology between Fc$_\epsilon$RI and these receptors is found, it is significant that an interaction between Fc$_\epsilon$RI and G proteins has been postulated to explain at least some of the biochemical pathways activated by this receptor (S. Cockcroft et al., Nature 314:534–536 (1985)). The topology of the α and β subunits has been discussed in J. P. Kinet et al., Biochemistry 26:4605–4610 (1987) and A. Shimizu et al., Proc. Natl. Acad. Sci. USA 85:1907–1911 (1988), in particular, the cytoplasmic localization of the C- and N-terminal portions of the β subunit. Two pieces of evidence support the topology of the γ-dimer as shown in FIGS. 12A–12D. The γ can be oxidatively iodinated on inverted vesicles but not on intact cells (D. Holowka et al.;, J. Biol. Chem. 259:3720–3728 (1984)) and, in vivo, γ becomes phosphorylated on threonine residues (R. Quarto et al., Mol. Immunol. 23:1215–1223 (1986)). None of the relevant residues are present in the small presumptive extracytoplasmic segment of γ but all are present on the presumptive cytoplasmic tail, i.e., two tyrosine and four threonine residues.

As a further means to examine the topology of the receptor, the putative extracellular and intracellular segments of the three subunits were analyzed for their relative content of basic residues, as suggested by G. von Heijne Biochim. Biophys. Acta 947:307–333 (1988). He found the ratio of basic/total residues varies as a function of the length of the segment studied, but in general was substantially higher in the non-translocated (intracellular) segments than in the translocated (extracellular) segments of membrane proteins. Table 3 below shows a good correspondence between the ratios calculated for the present model and the ratios expected on the basis of "known" membrane proteins (G. von Heijne, Biochim. Biophys. Acta 947:307–333 (1988)), thereby providing independent support for the topological model presented here.

TABLE 3

Ratio Lys + Arg/total in Translocated and Untranslocated Segments of Receptor Subunits

| Polypeptide | | Extracellular (translocated) | | | | Intracellular (untranslocated) | | |
|---|---|---|---|---|---|---|---|---|
| | | No. residues | Ratio found | Ratio expected | | No. residues | Ratio found | Ratio expected |
| α | | 179 | 0.13 | 0.11 | | 22 | 0.31 | 0.19 |
| β | loop 1 | 17 | 0.06 | 0.04 | N-term | 59 | 0.10 | 0.10 |
| | loop 3 | 28 | 0.03 | 0.04 | loop 2 | 12 | 0.25 | 0.20 |
| | | | | | C-term | 43 | 0.12 | 0.18 |
| γ | | 5 | 0 | 0.08 | | 36 | 0.22 | 0.16 |
| αβγ$_2$ | | 234 | 0.045 | 0.02–0.06 | | 208 | 0.17 | 0.12–0.16 |

TABLE 3-continued

Ratio Lys + Arg/total in Translocated and Untranslocated Segments of Receptor Subunits

| | Extracellular (translocated) | | | Intracellular (untranslocated) | | |
|---|---|---|---|---|---|---|
| | No. | Ratio | | No. | Ratio | |
| Polypeptide | residues | found | expected | residues | found | expected |

The expected values calculated from the data in FIG. 8 of G. von Heijne, Biochim. Biophys. Acta 947, 307–333 (1988), in which the ratio found for the extra-membrane segments from "known" proteins has been plotted as a function of the segments' length.

The model clarifies several important features with respect to the organization of the subunits. The β and dimer of γ interact with each other; in detergent solutions they dissociated from α as a unit before dissociating from each other (J. Rivera et al., Mol. Immunol. 25:647–661 (1988)), and occasionally, β and the γ dimer are observed to be disulfide-linked to each other (J. P. Kinet, Biochemistry 22:5729–5732 (1983)). The likeliest candidates for this bond are γ-cys7 and β-cys80 which are predicted to be topologically close. This would then require that at least the γ-cys26 residues are disulfide-linked in the γ dimer. Preliminary data on the receptor biosynthesis suggest that α and β interact with each other.

The functional properties of $Fc_\epsilon RI$ are broadly similar to those of several $Fc_\gamma R$. $Fc_{65}$ R appears to bind to homologous segments of the immunoglobulin's Fc region (B. Helm et al., Nature 331:180–183 (1988); A. Duncan et al., Nature 332:563–564 (1988)), and the binding site on the receptor is found on a homologous polypeptide having immunoglobulin-like domains (J. P. Kinet et al., Biochemistry 26:4605–4610 (1987); J. Ravetch et al., Science 234:718–725 (1986)). Both types of receptors need to be aggregated to initiate cell activation and, where studied, the latter appears to involve generation of broadly similar second messengers (H. Metzger et al., Ann. Rev. Immunol. 4:419–470 (1986); N. Hogg, Immunol. Today 9:185–187 (1988)). It is surprising, therefore, that whereas $Fc_\epsilon RI$ consists of four polypeptide chains, seven transmembrane segments and five cytoplasmic segments, $Fc_\epsilon RI$ appear to perform similar functions with a much simpler structure, i.e., an α-like subunit alone. The extreme case is that of $Fc_\gamma RIII$ which appears to lack even transmembrane and intracellular segments (P. Selvaray et al., Nature 333:565–567 (1988); D. Simmons et al., Nature 333:568–570 (1988); T. Huizinga et al., Nature 333:667–669 (1988)). It has been suggested that additional components of Fcγ receptors may have thus far been missed. Possibly such components are even more easily lost upon solubilization of the receptors than are the β and γ subunits of FRI (J. P. Kinet et al., Biochemistry 24:4117–4124 (1985)). A reasonable interpretation is that such hypothetical components would be homologous to β or γ or both. The availability of genetic probes for the latter components will now permit an in-depth exploration of this possibility.

The success in expression of IgE binding achieved according to the present invention has important therapeutic implications. Degranulation of mast cells and basophils triggered by $Fc_\epsilon RI$ accounts for many of the symptoms of allergy. Given the high incidence of this disorder, the discovery of a specific inhibitor of IgE binding is expected to yield enormous therapeutic benefits. The development of such an inhibitor has been hampered by the lack of a practical in vitro assay for the binding of human IgE to the human receptors. For example, a recent assessment of IgE-derived peptides of their inhibitory capacity had to be determined by skintesting (B. Helm et al., Nature 331:180–183 (1988)), a cumbersome and potentially dangerous procedure.

That the present invention achieves the expression of the transfected rodent receptor indicates that human $Fc_\epsilon RI$ can be similarly expressed. Alternatively, since at present only the cDNA coding for the human α subunit has been isolated (A. Shimizu et al., Proc. Natl. Acad. Sci. USA 85:1907–1911 (1988); J. Kochan et al., Nucl. Acids Res. 16:3584 (1988)), it is expected that it can be expressed in cotransfections with the cDNAs coding for the rodent β and γ chains.

A comparison between the human and rat α subunits is set forth in Table 4 below.

TABLE 4

Comparative Properties of Human and Rat Alpha Chains

| | Species | | |
|---|---|---|---|
| Domain | Human (amino acid residues 178–204 of SEQ ID NO:13) | Rat (amino acid residues 179–205 of SEQ ID NO:12) | % Homology |
| Extracellular | 180 | 181 | 49 |
| Transmembrane | 21 | 21 | 67+ |
| Intracellular | 31 | 20 | 23 |
| Total | 232 | 222 | 47* |

*Wt ave.
+Human: (amino acid residues 178–204 of SEQ ID NO:13) WLQFFIPLLVVILFAVDT-GLFISTQQQ
Rat: (amino acid residues 179–205 of SEQ ID NO:12) WLQLIFPSLA<u>VILFAVDTGL</u>WFSTHKQ It may be seen from the above Table that there is an overall homology between the human and rat alpha chains of about 47%, but an almost 70% homology in the presumed transmembrane domains. Indeed, when the transmembrane domains are examined closely, there is a stretch of 10 consecutive residues that are completely identical. This stretch of consecutive residues is underlined in Table 4.

Because the transmembrane segment is the region of the α chain that is most likely to interact with the β1 and γ chains, it was expected that the human α chain would be expressible, if transfected, along with the rat β and γ chains. This has proved to be the case as the present inventors have been able to express human IgE binding by COS cells transfected simultaneously with the human α and the rat β and γ subunits. It will be advantageous, of course, to have permanently transfected cell lines and for such lines, one will want to utilize the human β and γ subunits disclosed herein.

EXAMPLE 15

The Beta Subunit of FC$_\epsilon$R is Necessary for Expression in Mast Cells

FIGS. 20 and 21 present the results obtained from FACS analysis (IgE binding) of cells transfected with various combinations of Fc$_\epsilon$RI subunits.

FIG. 20: represents KU812 cells (a basophil line).

FIG. 21: represents COS-7 transfected cells.

The clone of Ku812 cells used does express the mRNA for the three subunits alpha, beta and gamma but the receptor is not naturally expressed on the surface.

In FIG. 21, the transfection of human alpha and gamma in COS-7 cells is confirmed to be sufficient for expression of the alpha-gamma complex on the surface of the transfectants. These results also show that human beta and not rat beta associates efficiently with human alpha and that therefore, rat beta cannot replace human beta.

FIG. 20 illustrates that transfection of alpha-gamma in KU812 results in very little expression of receptors. The level of expression is similar to the level obtained after transfection of beta and gamma. Therefore this level may be attributable to the endogenous alpha (for beta and gamma transfection) or to the endogenous beta (for alpha and gamma transfection). By contrast the level of expression after co-transfection of the three cDNAs is very substantial.

From these results, it may be concluded that:

1. in mast cells and basophils, regulation of the level of expression of the receptor may be different than in fibroblasts.
2. in human mast cells and basophils, receptor expression requires the presence of alpha, beta and gamma; whereas in transfected fibroblasts, human alpha and gamma are sufficient.

EXAMPLE 16

Isolation, Mapping and Sequencing of the Human FceRI β Gene

Initial attempts to isolate human β cDNA clones were by screening a human mast cell cDNA library with full-length rat and mouse cDNA probes. These probes were radiolabeled and used to screen 7×10$^5$ colonies. Four clones were isolated, all of which contained a 153 bp insert with 73% homology to rat β cDNA. The sequence of this insert corresponded to a portion of β which includes the intracellular loop and the third transmembrane domain. These four identical clones are the likely result of library amplification of a single clone generated by recombinations. Two additional libraries were screened: another mast cell cDNA library and a cDNA library derived from basophil-enriched leukocytes. The latter library was also used to isolate human γ cDNA clones. A total of 107 independent cDNA clones were screened with a panel of murine probes and oligonucleotides and with the 153 bp human β probe. However no additional clones were isolated.

6×10$^5$ independent genomic clones from a human genomic leukocyte library with the radiolabeled 153 bp human probe were subsequently screened, and 10 clones with an average size insert of 25 kb were isolated. These clones all hybridized with two 20 mer-oligonucleotide probes corresponding to the beginning and the end of the rat β coding γ sequence. Four different restriction patterns could be generated from the 10 clones. However, souther blots with various oligonucleotide probes scanning different regions of the rat β coding sequence indicated that the four restricted patterns were not the product of different genes. Rather the clones showed differences in the lengths of the sequences flanking the β gene.

One clone containing a 25 kb insert was chosen for further characterization mapping and sequencing. A restriction map shown in FIG. 13 was constructed by complete and incomplete digestion with the restriction endonuclease Hind III, Pst I, BamH I, Xba I, Sma I and Kpn I. A 3.2 kb Hind III fragment was found to hybridize with oligonucleotide probes corresponding to the start codon, and transmembrane region I and II of rat β. A 2.8 kb Sma I fragment hybridized with rat β probes of transmembrane domain III and IV and a 4.5 kb Sma I fragment with probes of the stop codon region. The 3 fragments were subcloned into pGEM 3 zf (+) or (−) and sequenced in full (FIGS. 14A–14Q) and SEQ ID NO:31. The fragment corresponding to the 0.9 kb gap between the Hind III and 2.8 kb Sma I fragments was produced by PCR and sequenced. Analysis using PCR confirmed that the two Sma I fragments were adjacent to each other.

By comparing the sequences of the human β gene and the rat β cDNA (FIG. 15) seven homologous regions which were likely localized to correspond to seven different exons.

EXAMPLE 17

Synthesis of Human β cDNA Coding Sequence

In order to confirm the sequence of the exons and to define the intro-exon borders, human β cDNA was synthesized by reverse transcription of RNA purified from basophil-enriched leukocytes followed by an amplification of the reverse transcripts using the polymerase chain reaction (PCR) (described in Materials and Methods herein). This applied product extended from 2 nucleotides preceding the start codon to 32 nucleotides following the stop codon. The cDNA sequence was found to be identical to the corresponding sequence of human β gene. This confirmed that the coding sequence of human β is contained in seven exons. Furthermore, the comparison of cDNA and gene sequences and the detection of consensus sequences for intron-exon borders in the human β gene allow for a precise determination of these borders. The 5' borders of the six intervening introns invariably start with GT and the 3' borders end with AG.

EXAMPLE 18

Analysis of Human β Transcripts

To evaluate the length of 5' and 3' untranslated sequences, the size of human β transcripts was analyzed. RNA from basophil-enriched leukocytes obtained from different individuals were hybridized by northern blotting with the radiolabeled 153 bp human β probe (FIG. 16A) Two transcripts around 3.9 kb were found in human basophils but not in COS-7 cells. The human transcripts are substantially longer than their rodent counterparts (2.7 and 1.75 kb) (Ra. 1989, Kinet, 1988) as detected in RBL cells by crosshybridization. This longer size may explain initial failures to isolate human β cDNAs from the three oligo-dT primed libraries. Similar results were obtained with a full-length cDNA probe of human β. Hybridization of the same RNAs with a human α cDNA probe revealed transcripts for α of the expected size (1.1 kb) (FIG. 16B). RNA from different cell lines were also hybridized with a full length human β cDNA probe (FIG. 16C). The message for human β is only detected in the basophil line KU812 but not in U937, Daudi and Hela cells. An additional band is seen in KU812 which could correspond to unspliced transcripts.

With an open reading frame of 732 bp and assuming 200 bp for the poly A tail, human β transcripts should contain about 3 kb of untranslated sequences. FIG. 15 shows that most of the untranslated sequences are in the seventh exon. The possibility that additional exons of 3' or 5' untranslated sequences had not yet been identified was also explored.

EXAMPLE 19

A. Characterization of the (A) 5' End and of the Transcription Initiation Site

The transcription start site was determined by sequencing directly a PCR amplified product of the reverse transcribed RNA as described in "Experimental Procedures". RNA from basophil-enriched leukocytes was reverse transcribed from a primer of the human β coding sequence. Poly-A tails were added to the reverse transcripts by treatment with terminal transferase and the resulting cDNAs were amplified by PCR. Single stranded DNAs (positive strands poly dT tailed) were then produced by asymmetric PCR and directly sequenced. The cDNA sequence of the negative strand corresponding to the 5' end of the RNA is shown in FIG. 17A and is compared to the relevant sequence of the β gene. The perfect match between the two sequences ends after GGGTT. Then the cDNA sequence reproducibly shows a C, which is not present in the gene, followed by the expected poly-A tail. This additional C may correspond to the G of the cap structure and indicate the location of the start site.

Experiments of 5' extension (FIG. 17B) confirmed that there is a major start site in this area (about 11 nucleotides 3' of the position described above). It is difficult, though, to exclude the possibility that the faint bands seen below and above the major start site correspond to minor start sits. However the presence of a TATAAA box found in the 5' sequence supports the existence of a unique start site. In addition the location of the TATAAA box (usually 25 nucleotides 5' of the start site) is more consistent with the precise localization of the start site as shown.

Indeed the TATAAA box is located between nucleotides 29 and 24 upstream of this start site as shown in FIG. 17A. Taken together the data indicate that the human β mRNA start with the sequence AACCC (see FIGS. 14A–14Q, and SEQ ID NO:31, and FIG. 17A) and has 102 bp of 5' untranslated sequence.
B. Characterization of the 3' end A comparison between the rat β cDNA and human β gene sequences FIG. 15) shows that the seventh exon of the β gene extends at least from nucleotides 6773 to at least nucleotide 8910. But an additional 3' untranslated sequence (about 800 bp) had to be found to fully account for the 3.9 kb transcripts. To analyze whether the missing sequence was part of the seventh exon or of other undetected exons, three probes from the β gene were prepared to test their reactivity with β transcripts. These transcripts hybridized in northern blots with both the Hsil-BamHI fragment (nucleotides 8460–9250) and the BamHI-SphI fragment (nucleotides 9250–9714) but not with the fragment 3' of the SphI site. Interestingly two polyadenylation signals AATAAA are found at nucleotides 9663 and 9758 (FIG. 14 and SEQ ID NO:31). Therefore this region is likely to correspond to the end of exon 7. It is likely that both polyadenylation signals could be used to create the apparent doublet of transcripts around 3.9 kb (see FIG. 16A–16C).

EXAMPLE 20

Organization of the Human β Gene

Taken together the data presented herein indicate that the human β gene contains seven exons and six introns and spans about 10 kb. Exon 1 codes for 102 bp of 5' untranslated sequence and the first 18 amino acid residues of the N-terminal cytoplasmic tail. Exon 2 encodes the remaining of the cytoplasmic tail and the first three residue of TM1. Exon 3 codes for the remaining of TM1, the first extracellular loop and the first half of TM2. Exon 4 encodes the second half of TM2 and a portion of the cytoplasmic loop. Exon 5 codes for the last three residue of the cytoplasmic loop, TM3 and most of the second extracellular loop. Exon 6 codes for the last two residues of the extracellular loop, TM4 and the first quarter of the C-terminal cytoplasmic tail. Finally, exon 7 codes for the remaining of the cytoplasmic tail and the long untranslated 3' sequence.

EXAMPLE 21

The Human β Protein

The human β protein comprises 244 amino-acid (aa) residues and has a molecular mass of 26,532 daltons (FIG. 18). Similar to rat (243 aa) and mouse β (236 aa), human β contains four hydrophobic segment suggestive of transmembrane domains (TM) but no leader peptide. FIGS. 19A–19B shows an alignment of the human sequence (SEQ ID NO:32) with the rat (SEQ ID NO:33) and mouse (SEQ ID NO:34) sequence. The consensus sequence for β (not shown) from the three species (rat, mouse and human) shows that 91.4% of the amino-acid residues are homologous while 68.7% are identical.

EXAMPLE 22

Transfection in COS-7 Cells: Expression of Human and Hybrid $Fc_{\epsilon}RI$ Receptors

TABLE 5

Functional expression of FcεRI after transfection of various subunit combinations

| Transfected cDNAs | | | n | % Fluorescent cells (FACS) Mean ± SD |
|---|---|---|---|---|
| Human α | — | — | 1 | 0.2 |
| Human α | Human β | — | 1 | 0.2 |
| Human α | — | Human γ | 7 | 10.4 ± 8.7 |

TABLE 5-continued

Functional expression of FcεRI after transfection of various subunit combinations

| Transfected cDNAs | | | % Fluorescent cells (FACS) | |
|---|---|---|---|---|
| | | | n | Mean ± SD |
| Human α | Human β | Human γ | 7 | 8.3 ± 5.0 |
| Human α | Rat β | Human γ | 4 | 5.4 ± 3.4 |
| Rat α | Rat β | Rat γ | 8 | 18.0 ± 17.8 |
| Rat α | Human β | Rat γ | 10 | 2.4 ± 2.0 |
| Rat α | Human β | Human γ | 5 | 1.8 ± 1.3 |
| Mouse α | Mouse β | Mouse γ | 4 | 8.2 ± 5.6 |
| Mouse α | Human β | Mouse γ | 6 | 1.6 ± 1.2 |
| Mouse α | Human β | Human γ | 2 | 1.5 ± 0.8 |
| Human α | — | Rat $\gamma_{trunc}$ | 7 | 1.4 ± 1.0 |
| Human α | Rat β | Rat $\gamma_{trunc}$ | 5 | 3.2 ± 2.8 |
| Human α | Human β | Rat $\gamma_{trunc}$ | 7 | 7.4 ± 7.9 |
| Rat α | Rat β | Rat $\gamma_{trunc}$ | 2 | 9.3 ± 0.8 |
| Rat α | Human β | Rat $\gamma_{trunc}$ | 2 | 0.4 ± 0.5 |

It was found that co-transfection of α, β, and γ cDNAs is necessary to promote expression of rat or mouse Rc$_ε$RI on the surface of transfected COS-7 cells. By contrast, co-transfection of human α and β cDNAs results in the surface expression of αγ complexes without apparent need for γ. With the availability of human γ cDNAs, the question was explored whether human β would influence in any way the efficiency of surface expression of the human receptor complex. Table 5 shows that co-transfection of human α and γ cDNAs into COS-7 cells results in 10.4%±8.7 of the cells being fluorescent when analyzed by FACS after binding of fluoresceinated IgE. This level of expression is not significantly modified when human β cDNA is co-transfected with human α and γ cDNAs (8.3%±5.0). Thus, human β does not seem to influence the level of surface expression of human FcεRI in transfected COS-7 cells. Substituting rat β or human β reduces the level of expression (5.4%±3.4).

The effect of substituting human β for rat β was analyzed. Co-transfection of rat α, β, γ cDNAs result in much higher level of expression (18.0%±17.8) than co-transfection of rat α γ with human γ (2.5%±2.0) (Student's t statistic=2.75; p≦0.014). Similarly co-transfection of mouse α, β, γ cDNAs is more efficient (8.2%±5.6) than co-transfection of mouse α, γ with human β (1.6%±1.2) (Student's t statistic:2.91; p≦0.019). Because replacing rat γ or mouse γ with human γ does not restore expression (compare 2.4% with 1.8%, and 1.6% with 1.5%), it is likely that the problem of expression resides in the human β-rat α or human β-mouse α interaction.

It is known that truncation of the cytoplasmic tail of rat γ prevents the surface expression of human α in transfectants (Varni-Blank, 1990). The question was whether human β could complement the surface expression of human α in these conditions. It was confirmed that co-transfection of human α with truncated rat γ permit only very poor surface expression of αγ complexes (1.4%±1.0). When human β is co-transfected with the latter combination there is an increase of expression (7.4%±7.3, n=7). However this increase does not become significant (p≦0.035) when one aberrant point is not included in the seven experiments. The same increase is not observed when rat β is substituted for human β (3.2%±2.8) suggesting again that there may be specific points of interaction between human α and β. In other experiments using the truncated rat γ, it was found that human β cannot be substituted for rat β in its interaction with rat α (compare 9.3%±0.6 with 0.4%±0.4; (t=13.0; p≦0.006).

Taken together these data indicate that there is a tendency for human β to interact more efficiently with human α than does rat β, but the species specificity is weak. By contrast, there is a strong species specificity in the interaction between rat β and rat α or between mouse β and mouse α.

Human αγ complexes may be expressed on the surface of transfected cells. Moreover co-transfection of human α and γ with rat β results only 20% of the receptors being αβγ complexes, the remaining 80% being αγ complexes. Therefore, it is theoretically possible that αγ complexes occur naturally. However in view of the species specificity of interaction between human β and α (see above), previous results obtained from the co-transfection of human α and γ with rat β suggest the in vivo situation could be different.

These genetic results, of course, provides much more than an assay, as important as the latter may be. Through directed mutation it will, in addition, allow the development of further information regarding the critical binding regions. It is expected that, using this information, rational drug design will become possible. It is further expected that it will be possible to block the function of the receptor itself, i.e., it will be possible to interfere with the early biochemical signals that result from activation of the receptor.

EXAMPLE 23

Detection of a Candidate Inhibitor Substance

In still further embodiments, the present invention concerns a method for identifying new Fc$_ε$RI inhibitory compounds, which may be termed as "candidate substances." It is contemplated that this screening technique will prove useful in general identification of any compounds that will serve the purpose of inhibiting the formation of Fc$_ε$RI as measured by various cell activation assays. (Mouse Interleukin-2 ELISA kit, Alberts et al., pp. 179–180, Adamczewski et al. (in press), Barones et al., 1991).

Thus, in these embodiments, the present invention is directed to a method for determining the ability of a candidate substance to inhibit the formation of the human Fc$_ε$RI complex, the method including generally the steps of:
(a) obtaining a composition comprising the human alpha, beta and gamma subunits of Fc$_ε$RI that are capable of complexing to form a functional and/or expressed receptor;
(b) admixing a candidate inhibitor substance with the composition; and
(c) determining the functional or expressed ability of the admixture.

An important aspect of the candidate substance screening assay hereof is the ability to prepare a composition of alpha, beta and gamma subunits in a relative purified form, for example, in a manner discussed herein. An aspect of the candidate substance screening assay in that without at least a relatively purified preparation, one will not be able to assay specifically for Fc$_ε$RI inhibition, as opposed to the effects of the inhibition upon other substances in the extract which then might affect the receptor. In any event, the successful cloning and isolation of the beta subunit now allows for the first time the ability to identify new compounds which can be used for inhibiting the Fc$_ε$RI in specific ways, thereby inhibiting the effects of the Fc$_ε$RI when bound to IgE.

The candidate screening assay is quite simple to set up and perform, and is related in many ways to the assays discussed above for determining Fc$_ε$RI activity. After obtaining a relatively purified preparation of the alpha, beta and gamma subunits, one will desire to simply admix a candidate substance with the preparation, preferably under conditions which would allow the receptor to form but for inclusion of an inhibitory substance. Thus, for example, one will typically desire to use cell activation assays as indirect measures of the presence of a functional receptor, or receptor expression, or both.

Accordingly, one will desire to measure or otherwise determine the activity of the relatively purified receptor in the absence of the assayed candidate substance in order to assess the relative inhibitory capability of the candidate substance.

In still further embodiments, the present invention is concerned with a method of inhibiting receptor formation and/or function which include subjecting the subunits to an effective concentration of a candidate substance identified in accordance with the candidate screening assay embodiments. This is, of course, an important aspect of the invention in that it is believed that by inhibiting the receptor one will be enabled to treat or prevent various aspects of allergic reactions. It is believed that the use of such inhibitors to block the release of histamine by binding of IgE to $Fc_\epsilon RI$ and serve to treat or palliate the symptoms of an allergic response. Inhibitors may be useful by themselves or in conjunction with other therapies.

EXAMPLE 24

Identification and Use of $Fc_\epsilon RI$ Inhibitors

If the action of receptor of IgE is inhibited, the allergic reaction will be proceed. This inhibition may be either at the level of transcription, translation, or protein action. Interference with transcription would necessitate interference with mRNA formation on the DNA template. Preferably, interference with the translation would necessitate interfering with the synthesis of proteins on the mRNA template. Alternatively, the action of the receptor may itself be disrupted either by destroying the structure of the receptor, prohibiting its formation, or binding the receptor or components thereof irreversibly to inhibitors.

Specifically designed peptides which block the function of the receptor are extremely valuable in preventing and treating allergic diseases. Embodiments of these blockers (antagonists) include any substrate analogous or inhibitor, e.g., oligopeptides or their derivatives which contain the amino acid sequence of the IgE binding site. Methods for identifying suitable inhibitors form candidate substances are disclosed in Example 23.

EXAMPLE 25

Preparation of the Human β Polypeptide by Recombinant Techniques

It is an additional object of the present invention to provide a ready means for producing the human beta subunit for use in detecting inhibitors, to develop treatment modalities, to develop antibodies for detection of the subunit, and to develop inactive mutants of the human beta subunits, which may also be use to inhibit formation of the $Fc_\epsilon RI$. Such mutants may be introduced into transgenic animals, for example, to produce animals useful for β assays.

An exemplary embodiment for preparing the beta subunit protein is to prepare a nucleic acid segment which includes a nucleic acid sequence capable of encoding the desired protein or polypeptide. This segment may be that which encodes the entire subunit or only some portion of it, for example, the alpha or gamma binding domain of the subunit. The segment may be as small as that capable of triggering a positive signal with an antibody, thereby, identifying the presence of a beta subunit. Segments functionally equivalent to those shown in FIGS. 14A–14Q, may also be selected depending on the desired polypeptide to be produced. Functional equivalence may be determined by testing whether the segment can cause cell activation using techniques disclosed herein to detect inhibitors from among candidate substances.

The nucleic acid segment selected is transferred into an environment appropriate for expression of the segment as a polypeptide. This environment may be a vessel containing a mixture capable of inducing expression. Alternatively, the segment may be transferred to a host cell be transformation, transfection via a recombinant expression vector, electroporation, or a "gene gun." The host cell may be selected from CHO cells, T cells, KU812 cells, P815 cells, or the like.

The recombinant expression vector will generally include a promoter. Embodiments of promoters are the α4 promoter, or any other suitable prokaryotic or eukaryotic promoters.

EXAMPLE 26

Antibodies Against the Proteins of the Present Invention

In other embodiment, the invention concerns the preparation of antibodies to the bete subunits of $Fc_\epsilon RI$ and species derived therefrom, either recombinant or nonrecombinantly prepared.

Compositions which include monoclonal antibodies of the present invention may be prepared by first fusing spleen cells of a rodent with myeloma cells from the same rodent species, wherein the rodent providing the spleen cells have been immunized with the β subunit peptide, precursor, or related peptides. The rodent species utilized will generally be a mouse. Of course, where a beta subunits is prepared which incorporates structural variations over the ones disclosed herein, it will likely be able to successfully employ a hybridoma system according to the species of interest.

In addition, the present invention provides a method for isolating beta subunits from other species which may be found antigenically cross-reactive with that of the human or rodent subunit. This method includes preparing an immunoabsorbent material having attached thereto an antibody to the subunit. Numerous immunoabsorbent materials are known to those skilled in the art and include, for example, Affi-Gel, Cn-Sepharose, protein A=Sepharose, and numerous other well know immunoadsorbent techniques. All such techniques of the immuno cross-reactive species (for a more complete listing, see *Monoclonal Hybridoma Antibodies: Techniques and Applications,* John G. Hurrell, ed. CRC Press, 1982, incorporated herein by reference).

Materials and Methods
Screening of cDNA and genomic libraries

The human basophil cDNA library and the human leukocytes genomic library have been described before and are available (Kuster, 1990). The human lung cDNA library (Miller, 1989) and a human skin cDNA library were provided by L. B. Schwartz (Medical College of Virginia, Richmond).

The following probes were prepared for screening the various libraries: The EcoRI-EcoRV fragment of rat β (Kinet, 1988) and the EcoRI fragment of mouse β (Ra, 1989), both of which contain the entire coding sequence of β and part of the 3' untranslated region. Fragments of the coding region of rat β cDNA (bp 1–304) and mouse β cDNA (bp 433–708) were made by polymerase chain reaction (PCR). Multiple oligonucleotides corresponding to various regions of rat, mouse and human β were synthesized on a model 380A automated DNA synthesizer (Applied Biosystems, Foster City, Calif.). All double stranded DNA probes were radiolabeled by random primer labeling and the oligonucleotides by end labeling as described elsewhere (Davis, 1986).

Hybridization and washing conditions and procedures for plaque purification subcloning, sequencing and DNA analysis were as described previously (Kuster, 1990).

Southern blot analysis

Digestion of genomic DNA from five different individuals with BamH BgI II, Eco RI, Hind III, Msp I and Pvu II and hybridization of these digests with a human cDNA probe (from start to stop codon) supports the existence of a unique gene (FIG. 18). In addition the lengths of the restriction fragments detected on the southern blot are entirely consistent with the lengths predicted from the sequence of the gene. Three BamHI sites (nucleotide 156, 6908, 9250) are presenting the gene. As expected only one fragment (156–9250) is seen here because the other fragments should not hybridize with the cDNA probe. The two predicted BgI II fragments (+334 to +1766 and +1766 to +7419) and the two predicted Hind III fragments (−454 to +2724 and +2724 to 1000042) are readily detected. The results obtained after EcoRI and PuvII digestions are consistent the fact that none of these sites are found in the sequence of the gene. Finally the pattern observed after Msp I digestion is also consistent with predicted fragments of 2067 bp, 3870 bp and a larger 5' fragment extending from nucleotide 3622 to an undetermined MspI site upstream of the gene.

cDNA synthesis by using the Polymerase Chain Reaction (PCR)

Basophils from 240 ml of blood were purified by double Percoll gradients as previously described (Warner, 1987) and basophil RNA extracted by the guanidium isothiocyanate method (Davis, 1986). Two µg of total RNA were reverse transcribed with Superscript reverse transcriptase using a random 9-mer primer as recommended by the manufacturer (Bethesda Research Laboratories, Gaithersburg Md.). One twentieth of the reaction product was amplified using the following primers: a 23-mer complementary to nucleotide −2 to +21 of the human β coding sequence and as backward primer a degenerated 21-mer of the mouse and rat β sequences starting 32 nucleotides after the stop codon. Temperature cycles were as follows: 1 cycle of 2 min. 95°/2 min. 94°/5 min. 37°/40 min. 72°, 4 cycles of 40 sec. 94°/1 min. 37°/4 min. 72°, and 36 cycles of 40 sec. 94°/1 min. 50°/4 min. 72° followed by a singled 15 minute extension. One µl of this reaction was reamplified omitting cycles 2 to 5 and the amplification product subcloned into pCR1000 using the TA cloning kit (Invitrogen, San Diego, Calif.).

Direct sequencing of gene fragments obtained by PCR

Purified insert-containing phage DNA from the leukocyte genomic library was linearized with NotI and 100 ng amplified with primers flanking the region to be sequenced. DNA amplification was achieved using 40 of the following cycles: denaturation for 1 min. at 94° C., annealing or 2 min. at 45–50° C. and extension for 3–6 min. at 72° C. Subsequently 1 µl of the amplified material was reamplified in three separate reactions (50 µl) Under identical conditions omitting one of the 2 primers in order to generate single stranded DNA. The three reactions were pooled, applied to an Ultrafree MC 30.000 spin column (Millipore, Bedford Mass.), and washed four times before being evaporated by vacuum. The single stranded DNA was sequenced by using the omitted primer or an internal primer. The comparison of sequences obtained by this method or by sequencing non amplified fragments being subcloned in pGEM vectors revealed no differences.

Sequencing the transcription start site

PCR was used to define the transcription start site. Procedures published elsewhere (Frohman, 1987) were modified as follows: 5 µg RNA were reverse transcribed as detailed above by using a primer corresponding to nucleotide +451 to 429 of the coding region. The resulting product was washed on a Centricon 100 column (Amicon, Beverly Mass) and a poly-A tails were at both ends added using terminal transferase (Bethesda Research Laboratories, Gaithersburg Md.) as recommended by the manufacturer. One sixth of this reaction was amplified with the following 2 primers: a 33-mer consisting of the M13 primer sequence followed by 17 T's and for the 3' end a primer derived from nucleotide 331 to 308 of the human β coding region sequence. Subsequently an internal amplification was performed exchanging the 3' primer for one equivalent to nucleotide +189 to 169. Finally, single stranded DNA was produced for sequencing by using an oligonucleotide corresponding to nucleotide 54 to 33 as the only primer. For all PCR's the annealing temperature was 45° C., the extension time 3 min.

Analysis of the transcription start site by 5' extension

An end labeled oligonucleotide corresponding to the negative strand at nucleotide 54 to 33 after the start codon was hybridized overnight at 42° C. to either 10 µg total RNA from enriched basophils or 10 µg tRNA, followed by extension with Superscript reverse transcriptase (Bethesda Research Laboratories, Gaithersburg Md.) at 45° C. for 90 min. The primer-extended products were separated on a 5% polyacrylamide urea gel in parallel with the sequencing reactions of the genomic DNA.

Cell Line KU812

A new myeloid cell line (KU812) was established from a patient with blastic crisis of chronic myelogenous leukemia. His blasts were morphologically characteristic of immature basophils and basophil colonies were grown in agar culture of the blood mononuclear cells. Suspension culture of his blood cells was continue for more than 2.5 years. The KU812 cells morphologically showed a fine reticular nuclei with nucleoli, and some of them contained metachromatic granules with toluidine blue (TB) staining. These granules were positive for astra blue (AB) staining. Immunological marker studies revealed that there were no lymphoid characters except Fc receptors. The KU812 cells grew colonies in in vitro agar cultures, which were proved to be composed of basophils by TB staining and AB staining. Cytogenetic analysis showed marked aneuploidy and was positive for the Philadelphia chromosome ($Ph^1$). The cell lysate was proved to contain histamine. These data suggest that KU812 is a cell line from leukemic basophil precursors. This is the first human basophil cell line. KU812 is useful in clarifying the mechanism of basophilic differentiation of the stem cells. (Kishi, *Leuk, Res,* 1985, a: 381–390).

Other methods

Northern and Genomic Southern blots were performed as described elsewhere (Davis, 1986). The various cDNAs were subcloned into the eukaryotic expression vector pCDL-SR(α) for the transfection studies (Takebe, 1988). COS-7 cells were transfected by the standard DEAE-Dextran method (Maniatis, 1982), except that a 3 minute incubation of the transfected cells in 10% DMSO in media as added after the chloroquine treatment.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

REFERENCES

The references listed below are incorporated herein by reference to the extent that they supplement, explain, provide a background for, or teach methodology, techniques and/or compositions employed herein.

1. Adamczewski et al., Evidence for two distinct kinase/phosphatase pathways in the activation of receptors coupled to non-receptor-kinases, in press)
2. Alberts et al., *Molecular Biology of the Cell,* 1983, pp. 179–180.
3. Baranes and Razin, *Blood,* 78: 2354–2364 (1991), Collaborative Biomedical Products, Becton-Dickinson, Catalog No. 30032, lot 904092, Mouse Interleukin-2 ELISA kit.
4. Blank, U., Ra C., Miller, L., White, K., Metzger, H., and Kinet, J. P. (1989) Nature 337, 187–189.
5. Davis, L. G., Dibner, M. D., and Battey, J. F. (1986) Basic Methods in Molecular Biology, Elsevier Science Publishing Co., New York
6. Frohman, M. A., Dush, M. K., and Martin, G. R. (1988) Proc. Natl. Acad. Sci. 85, 8999–9002
7. Huppi, K., Siwarski, D., Mock, B. A., and Kinet, J. P. (1989) J. Immunol. 143, 3787–3791.
8. Huppi, J., Mock, B. A., Hilgers, J. Kochan, J., and Kinet, J. P. (1988) J. Immunol. 141, 2807–2810.
9. Kinet, J. P., Blank, U., Ra, C., White, K., Metzger, H., and Kochan, J. (1988) Proc. Natl. Acad. Sci. U.S.A. 85, 6483–6487.
10. Kinet, J. P. (1990) Curr. Opinion Immunology 2, 499–505.
11. Kinet, J. P. Metzger, H., Hakimi, J., and Kochan, J. (1987) Biochemistry 26, 4605–4610.
12. Kochan, J., Pettine, L. F., Hakimi, J., Kisshi, J., and Kinet, J. P. (1988) Nucleic Acids Res 16, 3584–3594.
13. Kuster, H., Thompson, H., and Kinet, J. P. (1990) J. Biol. Chem. 265, 6448–6452.
14. Le Coniat, M., Kinet, J. P., and Berger, R. (1990) Immunogenetics 32, 183–186.
15. Letourneu, O., Kennedy, I. C. S., Brini, A. T., Ortaldo, J. R., O'Shea, J. J. and Kinet, J. P. (1991) J. Immunol. in press
16. Liu, F. T., Albrandt, K., and Robertson, M. W. (1988) Proc. Natl. Acad. Sci. U.S.A. 85, 5639–5643.
17. Maniatis, T., Fritsch, E. F., & Sambrook, J. (1982) Molecular Cloning, a Laboratory Manual, Cold Spring Harbor Laboratory, Cold Spring Harbor, N.Y.
18. Miller, J. S., Westin, E. H., and Schwartz, L. B. (1989) J. Clin. Invest. 84, 1188–1195
19. Miller, L., Blank, U., Metzger, H. and Kinet, J. P. (1989) Science 244, 334–337
20. Orloff, D. G., Ra. C., Frank, S. J., Klausner, R. D., and Kinet, J. P. (1990) Nature 347, 189–191.
21. Ra, C., Jouvin, M. H. E., and Kinet, J. P. (1989) J. Biol. Chem 264, 15323–15327.
22. Ra, C., Jouvin, M. H. E., Blank, U., and Kinet, J. P. (1989) Nature 341, 752–754
23. Ravetch J. V. and Kinet, J. P. (1991) Ann. Rev. Immunol. 9, 457–492.
24. Shimizu, A., Tepler, I., Benfey, P. N., Berenstein, E. H., Siraganian, R. P., and Leder, P. (1988) Proc. Natl. Acad. Sci. U.S.A. 85, 1907–1911.
25. Takebe, Y., Seiki, M., Fujisawa, J.-I., Hoy, P., Yokota, K., Arai, K.-I., Yoshida, M., Arai, N. (1988) Mol. Cell. Biol. 8, 466–472
26. Tepler, I., Shimizu, A., and Leder, P. (1989) J. Biol. Chem. 264, 5912–5915.
27. Varin-Blank, N., Metzger, H. (1990) Expression of mutated subunits of the high effinity Mast cell receptor for IgE. J. Biol. Chem.
28. Warner, J. A., Reshef, A., and MacGlashan, D. W. J. (1987) J. Immunol. Methods 105, 107–110.

What is claimed is:

1. A method for determining the ability of a candidate substance to inhibit the formation or function of the human Fc$_\epsilon$RI, comprising:
   (a) conferring on a host cell the ability to express the α, β, and γ subunits of the human Fc$_\epsilon$RI;
   (b) combining the host cell after step (a) with the candidate inhibitor substance;
   (c) placing the combination in conditions suitable for expression of Fc$_\epsilon$RI;
   (d) performing on the host cell candidate inhibitor combination of step c an assay for cell expression or for cell activation of a type which requires a functional human Fc$_\epsilon$RI; and
   (e) determining whether the candidate substance has inhibited cell activation or receptor expression.

2. The method of claim 1 wherein the host cell is selected from the group consisting of CHO cells, T cells, KU818 and P815 cells, and the cell activation assay comprises measuring the phosphorylation of the Fc$_\epsilon$RI receptor or of PLC-γ (phospholipase c-γ) by $P^{32}$ label uptake.

3. The method of claim 1 wherein the host cell is selected from the group consisting of T cells, KU812 cells and P815 cells, and the cell activation assay comprises measuring calcium uptake response.

4. The method of claim 1 wherein the host cell is selected from the group consisting of T cells, KU812 cells and P815 cells, and the cell activation assay comprises measuring phosphatydil inositol metabolism.

* * * * *

UNITED STATES PATENT AND TRADEMARK OFFICE
CERTIFICATE OF CORRECTION

PATENT NO. : 6,171,803 B1
DATED : January 9, 2001
INVENTOR(S) : Jean-Pierre Kinet It is certified that error appears in the above-identified patent and that said Letters Patent is hereby corrected as shown below:

Column 1,
Line 61, "Fc$_\varepsilon$FI" should read -- Fc$_\varepsilon$RI --.

Column 3,
Lines 36-37, "Using what should be the beginning of the first exon from the putative human beta gene," should read -- Using what should be the beginning of the first exon and the end of the coding sequence in the seventh exon from the putative human beta gene, --.

Column 10,
Line 61, "kinet" should read -- Kinet --.

Column 11,
Line 65, "HINDIII" should read -- HindIII --.

Column 13,
Line 20, "ILe" should read -- Ile --.
Line 38, "cloning" should read -- Cloning --.

Column 16,
Line 31, "was described" should read -- was as described --.

Column 20,
Line 19, "Sequence" should read -- Sequencing --.

Column 22,
Line 14, "FIG. 11" should read -- FIGS. 11A-11D --.

Column 25,
Line 19, "dissociated" should read -- dissociate --.

Column 28,
Line 26, "endonuclease" should read -- endonucleases --.

Column 31,
Line 22, "Rc$_\varepsilon$RI" should read -- Fc$_\varepsilon$RI --.

UNITED STATES PATENT AND TRADEMARK OFFICE
CERTIFICATE OF CORRECTION

PATENT NO. : 6,171,803 B1
DATED : January 9, 2001
INVENTOR(S) : Jean-Pierre Kinet It is certified that error appears in the above-identified patent and that said Letters Patent is hereby corrected as shown below:

Column 33,
Line 30, "will be proceed" should read -- will not proceed --.

Column 34,
Line 14, "be" should read -- by --.
Line 26, "embodiment" should read -- embodiments --.
Line 29, "bete" should read -- beta --.

Column 35,
Line 28, "1000042" should read -- 100042 --.
Line 29, "PuvII" should read -- PvuII --.

Signed and Sealed this

Sixth Day of August, 2002

Attest:

JAMES E. ROGAN
Attesting Officer        Director of the United States Patent and Trademark Office

SEQUENCE LISTING

```
<160> NUMBER OF SEQ ID NOS: 35

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 1
aagtactggc tatgattttt tatcccattg                                       30

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 2
```
gaattaatat ggtccctcag aaacctaagg tctccttg                                38

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 3
aagtactggc tatgattttt tatcccattg                                         30

<210> SEQ ID NO 4
<211> LENGTH: 17
<212> TYPE: PRT
<213> ORGANISM: Rattus norvegicus

<400> SEQUENCE: 4

Tyr Glu Glu Leu His Val Tyr Ser Pro Ile Tyr Ser Ala Leu Glu Asp
 1               5                  10                  15

Thr

<210> SEQ ID NO 5
<211> LENGTH: 26
<212> TYPE: DNA
<213> ORGANISM: Artificial Sequence
<220> FEATURE:
<221> NAME/KEY: modified_base
<222> LOCATION: (3)..(15)
<223> OTHER INFORMATION: N represents inosine
<220> FEATURE:
<221> NAME/KEY: misc_feature
<222> LOCATION: (1)..(26)
<223> OTHER INFORMATION: r represents g or a; s represents g or c; y
      represents t/u or c.
<220> FEATURE:
<223> OTHER INFORMATION: Description of Artificial Sequence:
      oligonucleotide primer

<400> SEQUENCE: 5
ggngartasa catgnarytc ytcata                                             26

<210> SEQ ID NO 6
<211> LENGTH: 26
<212> TYPE: DNA
<213> ORGANISM: Artificial Sequence
<220> FEATURE:
<221> NAME/KEY: modified_base
<222> LOCATION: (3)..(15)
<223> OTHER INFORMATION: N represents inosine
<220> FEATURE:
<221> NAME/KEY: misc_feature
<222> LOCATION: (1)..(26)
<223> OTHER INFORMATION: r represents g or a;  s represents g or c; y
      represents t/u or c.
<220> FEATURE:
<223> OTHER INFORMATION: Description of Artificial Sequence:
      oligonucleotide primer

<400> SEQUENCE: 6
ggnctrtasa catgnarytc ytcata                                             26

<210> SEQ ID NO 7
<211> LENGTH: 23
<212> TYPE: DNA
<213> ORGANISM: Homo sapiens

-continued

```
<400> SEQUENCE: 7
aataaaacaa aaaaaaaaaa atg                                              23

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: modified_base
<222> LOCATION: (9)
<223> OTHER INFORMATION: n represents  inosine
<220> FEATURE:
<221> NAME/KEY: misc_feature
<222> LOCATION: (1)..(20)
<223> OTHER INFORMATION: r represents g or a; y represents t/u or c.

<400> SEQUENCE: 8
garaartcng aygctctcta                                                  20

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: modified_base
<222> LOCATION: (12)..(24)
<223> OTHER INFORMATION: n represents  inosine
<220> FEATURE:
<221> NAME/KEY: misc_feature
<222> LOCATION: (1)..(26)
<223> OTHER INFORMATION: y represents t/u or c; r represents g or a.

<400> SEQUENCE: 9
aaycargara cntaygarac nytnaa                                           26

<210> SEQ ID NO 10
<211> LENGTH: 1174
<212> TYPE: DNA
<213> ORGANISM: Homo sapiens
<220> FEATURE:
<221> NAME/KEY: CDS
<222> LOCATION: (107)..(880)

<400> SEQUENCE: 10
tactaagagt ctccagcatc ctccacctgt ctaccaccga gcatgggcct atatttgaag      60
ccttagatct ctccagcaca gtaagcacca ggagtccatg aagaag atg gct cct       115
                                                Met Ala Pro
                                                  1 gcc atg gaa tcc cct act cta ctg tgt gta gcc tta ctg ttc ttc gct      163
Ala Met Glu Ser Pro Thr Leu Leu Cys Val Ala Leu Leu Phe Phe Ala
  5                  10                  15 cca gat ggc gtg tta gca gtc cct cag aaa cct aag gtc tcc ttg aac      211
Pro Asp Gly Val Leu Ala Val Pro Gln Lys Pro Lys Val Ser Leu Asn
 20                  25                  30                  35 cct cca tgg aat aga ata ttt aaa gga gag aat gtg act ctt aca tgt      259
Pro Pro Trp Asn Arg Ile Phe Lys Gly Glu Asn Val Thr Leu Thr Cys
                 40                  45                  50 aat ggg aac aat ttc ttt gaa gtc agt tcc acc aaa tgg ttc cac aat      307
Asn Gly Asn Asn Phe Phe Glu Val Ser Ser Thr Lys Trp Phe His Asn
             55                  60                  65
```

-continued

```
ggc agc ctt tca gaa gag aca aat tca agt ttg aat att gtg aat gcc    355
Gly Ser Leu Ser Glu Glu Thr Asn Ser Ser Leu Asn Ile Val Asn Ala
         70                  75                  80 aaa ttt gaa gac agt gga gaa tac aaa tgt cag cac caa caa gtt aat    403
Lys Phe Glu Asp Ser Gly Glu Tyr Lys Cys Gln His Gln Gln Val Asn
 85                  90                  95 gag agt gaa cct gtg tac ctg gaa gtc ttc agt gac tgg ctg ctc ctt    451
Glu Ser Glu Pro Val Tyr Leu Glu Val Phe Ser Asp Trp Leu Leu Leu
100                 105                 110                 115 cag gcc tct gct gag gtg gtg atg gag ggc cag ccc ctc ttc ctc agg    499
Gln Ala Ser Ala Glu Val Val Met Glu Gly Gln Pro Leu Phe Leu Arg
                120                 125                 130 tgc cat ggt tgg agg aac tgg gat gtg tac aag gtg atc tat tat aag    547
Cys His Gly Trp Arg Asn Trp Asp Val Tyr Lys Val Ile Tyr Tyr Lys
            135                 140                 145 gat ggt gaa gct ctc aag tac tgg tat gag aac cac aac atc tcc att    595
Asp Gly Glu Ala Leu Lys Tyr Trp Tyr Glu Asn His Asn Ile Ser Ile
        150                 155                 160 aca aat gcc aca gtt gaa gac agt gga acc tac tac tgt acg ggc aaa    643
Thr Asn Ala Thr Val Glu Asp Ser Gly Thr Tyr Tyr Cys Thr Gly Lys
    165                 170                 175 gtg tgg cag ctg gac tat gag tct gag ccc ctc aac att act gta ata    691
Val Trp Gln Leu Asp Tyr Glu Ser Glu Pro Leu Asn Ile Thr Val Ile
180                 185                 190                 195 aaa gct ccg cgt gag aag tac tgg cta caa ttt ttt atc cca ttg ttg    739
Lys Ala Pro Arg Glu Lys Tyr Trp Leu Gln Phe Phe Ile Pro Leu Leu
                200                 205                 210 gtg gtg att ctg ttt gct gtg gac aca gga tta ttt atc tca act cag    787
Val Val Ile Leu Phe Ala Val Asp Thr Gly Leu Phe Ile Ser Thr Gln
            215                 220                 225 cag cag gtc aca ttt ctc ttg aag att aag aga acc agg aaa ggc ttc    835
Gln Gln Val Thr Phe Leu Leu Lys Ile Lys Arg Thr Arg Lys Gly Phe
        230                 235                 240 aga ctt ctg aac cca cat cct aag cca aac ccc aaa aac aac tga        880
Arg Leu Leu Asn Pro His Pro Lys Pro Asn Pro Lys Asn Asn
    245                 250                 255 tataattact caagaaatat ttgcaacatt agttttttc cagcatcagc aattgctact    940
caattgtcaa acacagcttg caatatacat agaaacgtct gtgctcaagg atttatagaa   1000
atgcttcatt aaactgagtg aaactggtta agtggcatgt aatagtaagt gctcaattaa   1060
cattggttga ataaatgaga gaatgaatag attcatttat tagcattgta aaagagatgt   1120
tcaatttcaa taaataaat ataaaaccat gtaaaaaaaa aaaaaaaaaa aaaa          1174

<210> SEQ ID NO 11
<211> LENGTH: 257
<212> TYPE: PRT
<213> ORGANISM: Homo sapiens

<400> SEQUENCE: 11

Met Ala Pro Ala Met Glu Ser Pro Thr Leu Leu Cys Val Ala Leu Leu
 1               5                  10                  15

Phe Phe Ala Pro Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Glu Thr Asn Ser Ser Leu Asn Ile
```

-continued

```
                 65                  70                  75                  80
Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn

<210> SEQ ID NO 12
<211> LENGTH: 222
<212> TYPE: PRT
<213> ORGANISM: Rattus sp.

<400> SEQUENCE: 12

Ala Thr Gln Lys Ser Val Val Ser Leu Asp Pro Pro Trp Ile Arg Ile
 1               5                  10                  15

Leu Thr Gly Asp Lys Val Thr Leu Ile Cys Asn Gly Asn Asn Ser Ser
                20                  25                  30

Gln Met Asn Ser Thr Lys Trp Ile His Asn Asp Ser Ile Ser Asn Val
            35                  40                  45

Lys Ser Ser His Trp Val Ile Val Ser Ala Thr Ile Gln Asp Ser Gly
        50                  55                  60

Lys Tyr Ile Cys Gln Lys Gln Gly Phe Tyr Lys Ser Lys Pro Val Tyr
65                  70                  75                  80

Leu Asn Val Met Gln Glu Trp Leu Leu Leu Gln Ser Ser Ala Asp Val
                85                  90                  95

Val Leu Asp Asn Gly Ser Phe Asp Ile Arg Cys Arg Ser Trp Lys Lys
            100                 105                 110

Trp Lys Val His Lys Val Ile Tyr Tyr Lys Asp Asp Ile Ala Phe Lys
        115                 120                 125

Tyr Ser Tyr Asp Ser Asn Asn Ile Ser Ile Arg Lys Ala Thr Phe Asn
    130                 135                 140

Asp Ser Gly Ser Tyr His Cys Thr Gly Tyr Leu Asn Lys Val Glu Cys
145                 150                 155                 160

Lys Ser Asp Lys Phe Ser Ile Ala Val Val Lys Asp Tyr Thr Ile Glu
                165                 170                 175

Tyr Arg Trp Leu Gln Leu Ile Phe Pro Ser Leu Ala Val Ile Leu Phe
```

```
                    180                 185                 190
Ala Val Asp Thr Gly Leu Trp Phe Ser Thr His Lys Gln Phe Glu Ser
            195                 200                 205
Ile Leu Lys Ile Gln Lys Thr Gly Lys Gly Lys Lys Gly
        210                 215                 220
```

<210> SEQ ID NO 13
<211> LENGTH: 232
<212> TYPE: PRT
<213> ORGANISM: Homo sapiens

<400> SEQUENCE: 13

```
Val Pro Gln Lys Pro Lys Val Ser Leu Asn Pro Pro Trp Asn Arg Ile
  1               5                  10                  15
Phe Lys Gly Glu Asn Val Thr Leu Thr Cys Asn Gly Asn Asn Phe Phe
                 20                  25                  30
Glu Val Ser Ser Thr Lys Trp Phe His Asn Gly Ser Leu Ser Glu Glu
             35                  40                  45
Thr Asn Ser Ser Leu Asn Ile Val Asn Ala Lys Phe Glu Asp Ser Gly
         50                  55                  60
Glu Tyr Lys Cys Gln His Gln Gln Val Asn Glu Ser Glu Pro Val Tyr
 65                  70                  75                  80
Leu Glu Val Phe Ser Asp Trp Leu Leu Leu Gln Ala Ser Ala Glu Val
                 85                  90                  95
Val Met Glu Gly Gln Pro Leu Phe Leu Arg Cys His Gly Trp Arg Asn
                100                 105                 110
Trp Asp Val Tyr Lys Val Ile Tyr Tyr Lys Asp Gly Glu Ala Leu Lys
            115                 120                 125
Tyr Trp Tyr Glu Asn His Asn Ile Ser Ile Thr Asn Ala Thr Val Glu
        130                 135                 140
Asp Ser Gly Thr Tyr Tyr Cys Thr Gly Lys Val Trp Gln Leu Asp Tyr
145                 150                 155                 160
Glu Ser Glu Pro Leu Asn Ile Thr Val Ile Lys Ala Pro Arg Glu Lys
                165                 170                 175
Tyr Trp Leu Gln Phe Phe Ile Pro Leu Leu Val Val Ile Leu Phe Ala
            180                 185                 190
Val Asp Thr Gly Leu Phe Ile Ser Thr Gln Gln Gln Val Thr Phe Leu
        195                 200                 205
Leu Lys Ile Lys Arg Thr Arg Lys Gly Phe Arg Leu Leu Asn Pro His
    210                 215                 220
Pro Lys Pro Asn Pro Lys Asn Asn
225                 230
```

<210> SEQ ID NO 14
<211> LENGTH: 227
<212> TYPE: PRT
<213> ORGANISM: Mus sp.

<400> SEQUENCE: 14

```
Ala Thr Glu Lys Ser Val Leu Thr Leu Asp Pro Pro Trp Ile Arg Ile
  1               5                  10                  15
Phe Thr Gly Glu Lys Val Thr Leu Ser Cys Tyr Gly Asn Asn His Leu
                 20                  25                  30
Gln Met Asn Ser Thr Thr Lys Trp Ile His Asn Gly Thr Val Ser Glu
             35                  40                  45
Val Asn Ser Ser His Leu Val Ile Val Ser Ala Thr Val Gln Asp Ser
```

```
                50                      55                      60
Gly Lys Tyr Ile Cys Gln Lys Gln Gly Leu Phe Lys Ser Lys Pro Val
 65                      70                      75                      80

Tyr Leu Asn Val Thr Gln Asp Trp Leu Leu Gln Thr Ser Ala Asp
                     85                      90                      95

Met Ile Leu Val His Gly Ser Phe Asp Ile Arg Cys His Gly Trp Lys
                100                     105                     110

Asn Trp Asn Val Arg Lys Val Ile Tyr Tyr Arg Asn Asp His Ala Phe
                115                     120                     125

Asn Tyr Ser Tyr Glu Ser Pro Val Ser Ile Arg Glu Ala Thr Leu Asn
                130                     135                     140

Asp Ser Gly Thr Tyr His Cys Lys Gly Tyr Leu Arg Gln Val Glu Tyr
145                     150                     155                     160

Glu Ser Asp Lys Phe Arg Ile Ala Val Val Lys Ala Tyr Lys Cys Lys
                    165                     170                     175

Tyr Tyr Trp Leu Gln Leu Ile Phe Pro Leu Leu Val Ala Ile Leu Phe
                    180                     185                     190

Ala Val Asp Thr Gly Leu Leu Leu Ser Thr Glu Gln Phe Lys Ser
                195                     200                     205

Val Leu Glu Ile Gln Lys Thr Gly Lys Tyr Lys Lys Val Glu Thr Glu
210                     215                     220

Leu Leu Thr
225

<210> SEQ ID NO 15
<211> LENGTH: 32
<212> TYPE: DNA
<213> ORGANISM: Homo sapiens
<220> FEATURE:
<221> NAME/KEY: CDS
<222> LOCATION: (9)..(11)
<220> FEATURE:
<221> NAME/KEY: CDS
<222> LOCATION: (21)..(32)

<400> SEQUENCE: 15 gaattaat atg    aatgaattt aag gtc tcc ttg                                32
         Met              Lys Val Ser Leu
          1                5

<210> SEQ ID NO 16
<211> LENGTH: 1
<212> TYPE: PRT
<213> ORGANISM: Homo sapiens

<400> SEQUENCE: 16

Met
 1

<210> SEQ ID NO 17
<211> LENGTH: 4
<212> TYPE: PRT
<213> ORGANISM: Homo sapiens

<400> SEQUENCE: 17

Lys Val Ser Leu
 1

<210> SEQ ID NO 18
<211> LENGTH: 38
<212> TYPE: DNA
```

```
<213> ORGANISM: Homo sapiens
<220> FEATURE:
<221> NAME/KEY: CDS
<222> LOCATION: (9)..(38)

<400> SEQUENCE: 18 gaattaat atg gtc cct cag aaa cct aag gtc tcc ttg         38
        Met Val Pro Gln Lys Pro Lys Val Ser Leu
        1               5                   10

<210> SEQ ID NO 19
<211> LENGTH: 10
<212> TYPE: PRT
<213> ORGANISM: Homo sapiens

<400> SEQUENCE: 19

Met Val Pro Gln Lys Pro Lys Val Ser Leu
1               5                   10

<210> SEQ ID NO 20
<211> LENGTH: 30
<212> TYPE: DNA
<213> ORGANISM: Homo sapiens
<220> FEATURE:
<221> NAME/KEY: CDS
<222> LOCATION: (1)..(15)

<400> SEQUENCE: 20 aag tac tgg cta tga tttttatcc cattg                      30
Lys Tyr Trp Leu
  1           5

<210> SEQ ID NO 21
<211> LENGTH: 4
<212> TYPE: PRT
<213> ORGANISM: Homo sapiens

<400> SEQUENCE: 21

Lys Tyr Trp Leu
  1

<210> SEQ ID NO 22
<211> LENGTH: 2545
<212> TYPE: DNA
<213> ORGANISM: Homo sapiens
<220> FEATURE:
<221> NAME/KEY: sig_peptide
<222> LOCATION: (46)..(54)
<220> FEATURE:
<221> NAME/KEY: CDS
<222> LOCATION: (46)..(786)

<400> SEQUENCE: 22
acgtttctgt gtaacaatat cttttattcc tggatagtcc aatta atg aaa aaa atg     57
                                                Met Lys Lys Met
                                                1 gac aca gaa aat aag agc aga gca gat ctt gct ctc cca aac cca caa      105
Asp Thr Glu Asn Lys Ser Arg Ala Asp Leu Ala Leu Pro Asn Pro Gln
5                   10                  15                  20 gaa tcc ccc agc gca cct gac att gaa ctc ttg gaa gcg tcc cct cct      153
Glu Ser Pro Ser Ala Pro Asp Ile Glu Leu Leu Glu Ala Ser Pro Pro
            25                  30                  35 gca aaa gct cta cca gag aag cca gcc tca ccc cca cag cag aca           201
Ala Lys Ala Leu Pro Glu Lys Pro Ala Ser Pro Pro Gln Gln Thr
        40                  45                  50 tgg cag tca ttt ttg aag aaa gag ttg gag ttc ctg ggc gta acc caa      249
```

```
Trp Gln Ser Phe Leu Lys Lys Glu Leu Glu Phe Leu Gly Val Thr Gln
        55                  60                  65 gtt ctg gtt ggt ttg ata tgc ctt tgt ttt gga aca gtt gtc tgc tcc        297
Val Leu Val Gly Leu Ile Cys Leu Cys Phe Gly Thr Val Val Cys Ser
    70                  75                  80 aca ctc cag act tca gac ttt gac gac gaa gtg ctt tta tta tat aga        345
Thr Leu Gln Thr Ser Asp Phe Asp Asp Glu Val Leu Leu Leu Tyr Arg
85                  90                  95                 100 gca ggc tac cca ttc tgg ggt gca gtg ctg ttt gtt ttg tct gga ttt        393
Ala Gly Tyr Pro Phe Trp Gly Ala Val Leu Phe Val Leu Ser Gly Phe
                105                 110                 115 ttg tca att atg tcc gaa agg aaa aac aca ctg tat ctg gtg aga ggc        441
Leu Ser Ile Met Ser Glu Arg Lys Asn Thr Leu Tyr Leu Val Arg Gly
            120                 125                 130 agc ctg gga gca aac att gtc agc agc atc gct gca ggc ttg ggg atc        489
Ser Leu Gly Ala Asn Ile Val Ser Ser Ile Ala Ala Gly Leu Gly Ile
        135                 140                 145 gcc ata ttg att ctc aat ctg agc aac aac tcc gct tat atg aac tac        537
Ala Ile Leu Ile Leu Asn Leu Ser Asn Asn Ser Ala Tyr Met Asn Tyr
150                 155                 160 tgc aag gat ata acc gaa gac gat ggt tgc ttc gtg act tct ttc atc        585
Cys Lys Asp Ile Thr Glu Asp Asp Gly Cys Phe Val Thr Ser Phe Ile
165                 170                 175                 180 aca gaa ctg gtg ttg atg ttg ctg ttt ctc acc atc ctg gcc ttt tgc        633
Thr Glu Leu Val Leu Met Leu Leu Phe Leu Thr Ile Leu Ala Phe Cys
                185                 190                 195 agt gcc gtg ctg ctc att atc tat agg att gga caa gaa ttt gag cgt        681
Ser Ala Val Leu Leu Ile Ile Tyr Arg Ile Gly Gln Glu Phe Glu Arg
            200                 205                 210 agt aag gtc ccc gat gac cgt ctc tat gaa gaa tta cat gtg tat tca        729
Ser Lys Val Pro Asp Asp Arg Leu Tyr Glu Glu Leu His Val Tyr Ser
        215                 220                 225 cca att tac agt gcg ttg gaa gac aca agg gaa gcg tcc gca cca gtg        777
Pro Ile Tyr Ser Ala Leu Glu Asp Thr Arg Glu Ala Ser Ala Pro Val
230                 235                 240 gtt tca taa gaatcaaggg gccaggacaa tctgattcca gtctagtctt               826
Val Ser
245 gagagtcgat cttttttgcaa cattatggca acatttctgt ttcctccgca ctctatcaac    886 ttttcaattg gattgttctg tagataccccc tgtttcagtt atgatgcctc tggtctttaa    946 ttatctccct ttttgtggat atcgttcaat ccagtttttct tgttttgtgt cacagtctca   1006 catacaacct ttctggaaag tcatcaaaaa caagctagct tttattgcat gtctactttc   1066 atgaacaaaa ggaaggagga gttattttga gagtttaact aaacttagat aatcaggtaa   1126 tatttgactc ttagttcatt ttagaattct caacaatact tgtgcatgat atatgcccac   1186 catatcaagc cttctatata tatttaatat ggtatttact tttctatgta gatagatttt   1246 ccaccctcaa taataatggg ttttttcagag acataaagct ttatgaaaag acacatatta   1306 tctaattcat gggtatattc actaatacag ttgttgctca gtggtgttta ctacttggtg   1366 ggtagtaggt aatagagaac attattaaat cattcagtgt agtgagatgc ataggtaaaa   1426 tcagggacac tgtgagtgtg tatatctttt ggtaagacat gtgtgaaaat gaagaataaa   1486 ctgatgaaga cttgagctgg aaagtagtca atgggaatga caagaaatga ttgtgtataa   1546 cacttgtaga taaataacta ccaacaattg gtagagattg ccatgtatgc ctaaaatctc   1606 ccagcccaag gccagcctct gttacacagt gagttagagg ccagtctggg ctacacaaga   1666
```

-continued

```
tcatacatca aaggacgaaa gaagatgttg gttcaaactg ttaacacagt aagggatatt    1726
taaacaaaca gaagtttgac tgatatattg agtgcttgag ttttaataa aactgaatga     1786 ataacattgc gggggagggg agcagtgatg cagaagtctg gatgatggag gagtagcaga    1846
atcagatgaa acattgaaac gtatttccag acttttgttc tgagatggtt ataagagcaa    1906
tcaccattaa atgaagaagg tcaagacacc aaaagaatta ttttgagata gaattaagac    1966
agtcaaaatc cacatgccta tacttagaag gtgaagtaag gatcaaaagt agaaagccta    2026
acgattagtt ggaaaagcat attacgttag gcagcagatg tctatagtgg agaaaagtta    2086
aacaaggaga ataatgaac caccagagac tctacatgtt ggtttgggaa ataagagaaa     2146
atagcaattc taaacgaatg caaactctga agaagcattt cccaaagggt gtgggcagag    2206
gaccagaaca tttgcaaatg tacctagaga gcaaacctga ataggaggta aaatggggga    2266
aaagcagcta agaaaatgat tttgttgctg ttatttagat tttaaaagaa acaaaaagag    2326
tcattaaaaa tctgtttgct gggatcagtt attgtgttct ctgtgtatgt ccaaagtaca    2386
ggtaactttt ctaaatcttc ctgtaaggct cacctcatat gtctcttcac atagccacac    2446
ccttgattca cagttactct accacagtag taaactgtgc ttgtggtctc ccttatgtat    2506
cttcactagt gtttataaaa taaatcagaa ttatttaaa                           2545
```

<210> SEQ ID NO 23
<211> LENGTH: 246
<212> TYPE: PRT
<213> ORGANISM: Homo sapiens

<400> SEQUENCE: 23

```
Met Lys Lys Met Asp Thr Glu Asn Lys Ser Arg Ala Asp Leu Ala Leu
 1               5                  10                  15

Pro Asn Pro Gln Glu Ser Pro Ala Pro Asp Ile Glu Leu Leu Glu
                20                  25                  30

Ala Ser Pro Pro Ala Lys Ala Leu Pro Glu Lys Pro Ala Ser Pro Pro
            35                  40                  45

Pro Gln Gln Thr Trp Gln Ser Phe Leu Lys Lys Glu Leu Glu Phe Leu
        50                  55                  60

Gly Val Thr Gln Val Leu Val Gly Leu Ile Cys Leu Cys Phe Gly Thr
65                  70                  75                  80

Val Val Cys Ser Thr Leu Gln Thr Ser Asp Phe Asp Asp Glu Val Leu
                85                  90                  95

Leu Leu Tyr Arg Ala Gly Tyr Pro Phe Trp Gly Ala Val Leu Phe Val
                100                 105                 110

Leu Ser Gly Phe Leu Ser Ile Met Ser Glu Arg Lys Asn Thr Leu Tyr
            115                 120                 125

Leu Val Arg Gly Ser Leu Gly Ala Asn Ile Val Ser Ser Ile Ala Ala
        130                 135                 140

Gly Leu Gly Ile Ala Ile Leu Ile Leu Asn Leu Ser Asn Asn Ser Ala
145                 150                 155                 160

Tyr Met Asn Tyr Cys Lys Asp Ile Thr Glu Asp Gly Cys Phe Val
                165                 170                 175

Thr Ser Phe Ile Thr Glu Leu Val Leu Met Leu Leu Phe Leu Thr Ile
                180                 185                 190

Leu Ala Phe Cys Ser Ala Val Leu Leu Ile Ile Tyr Arg Ile Gly Gln
            195                 200                 205

Glu Phe Glu Arg Ser Lys Val Pro Asp Asp Arg Leu Tyr Glu Glu Leu
        210                 215                 220
```

-continued

His Val Tyr Ser Pro Ile Tyr Ser Ala Leu Glu Asp Thr Arg Glu Ala
225                 230                 235                 240

Ser Ala Pro Val Val Ser
                245

<210> SEQ ID NO 24
<211> LENGTH: 286
<212> TYPE: DNA
<213> ORGANISM: Homo sapiens
<220> FEATURE:
<221> NAME/KEY: CDS
<222> LOCATION: (1)..(18)

<400> SEQUENCE: 24 gtg aga aca tat ctg taa ttgtttctga aatgatgcta accagagatt         48
Val Arg Thr Tyr Leu
 1               5 ttattttaat caaagacaac taattttctt ttaatcaagt gcttatctct agcctttcaa   108
taatatctac agttcttcat ttatatgcac atagccatct ataaatgtag tttccaaagc   168
actctctaca tatactcatt aacaagagca aatacactca ccacagttaa ctatggttta   228
acccattact atacttttat tgactgaaaa ccttgagact gtacaaaaaa aaaaaaaa     286

<210> SEQ ID NO 25
<211> LENGTH: 5
<212> TYPE: PRT
<213> ORGANISM: Homo sapiens

<400> SEQUENCE: 25

Val Arg Thr Tyr Leu
 1               5

<210> SEQ ID NO 26
<211> LENGTH: 586
<212> TYPE: DNA
<213> ORGANISM: Rattus sp.
<220> FEATURE:
<221> NAME/KEY: sig_peptide
<222> LOCATION: (23)..(76)
<220> FEATURE:
<221> NAME/KEY: mat_peptide
<222> LOCATION: (77)..(283)
<220> FEATURE:
<221> NAME/KEY: CDS
<222> LOCATION: (23)..(283)

<400> SEQUENCE: 26
agcgctgcag ccccgccca gg atg atc cca gcg gtg atc ttg ttc ttg ctc    52
                        Met Ile Pro Ala Val Ile Leu Phe Leu Leu
                           -15                 -10 ctt ttg gtg gaa gaa gca gct gcc cta gga gag ccg cag ctc tgc tat   100
Leu Leu Val Glu Glu Ala Ala Ala Leu Gly Glu Pro Gln Leu Cys Tyr
         -5              -1   1               5 atc ctg gat gcc atc ctg ttt ttg tat ggt att gtc ctt acc ctg ctc   148
Ile Leu Asp Ala Ile Leu Phe Leu Tyr Gly Ile Val Leu Thr Leu Leu
         10                  15                  20 tac tgt cga ctc aag atc cag gtc cga aag gca gac ata gcc agc cgt   196
Tyr Cys Arg Leu Lys Ile Gln Val Arg Lys Ala Asp Ile Ala Ser Arg
     25                  30                  35                  40 gag aaa tca gat gct gtc tac acg ggc ctg aac acc cgg aac cag gag   244
Glu Lys Ser Asp Ala Val Tyr Thr Gly Leu Asn Thr Arg Asn Gln Glu
                 45                  50                  55 aca tat gag act ctg aaa cat gag aaa cca ccc caa tag ctttacaaca    293

```
Thr Tyr Glu Thr Leu Lys His Glu Lys Pro Pro Gln
            60                  65 cgtgttctca gctgcattcc ttttccgctt ttaattctct cctcgccctc atgattgacg    353
tggctgtgct acctccgtgc ttctggaact agctgacctt attcccagaa ccatgctagg    413
ctctaaatca atgtccccat atccaccaaa gacttactca ctgacatttc tcttctccca    473
tcctcctttg cttcattcct ctttccttcc ctgatcctct gtgctcacta aacaatggga    533
agggattacc cccaataaag ctgccagag atcacgctca aaaaaaaaaa aaa            586
```

```
<210> SEQ ID NO 27
<211> LENGTH: 86
<212> TYPE: PRT
<213> ORGANISM: Rattus sp.

<400> SEQUENCE: 27

Met Ile Pro Ala Val Ile Leu Phe Leu Leu Leu Val Glu Glu Ala
            -15                 -10                 -5

Ala Ala Leu Gly Glu Pro Gln Leu Cys Tyr Ile Leu Asp Ala Ile Leu
      -1  1              5                  10

Phe Leu Tyr Gly Ile Val Leu Thr Leu Leu Tyr Cys Arg Leu Lys Ile
 15                  20                  25                  30

Gln Val Arg Lys Ala Asp Ile Ala Ser Arg Glu Lys Ser Asp Ala Val
                 35                  40                  45

Tyr Thr Gly Leu Asn Thr Arg Asn Gln Glu Thr Tyr Glu Thr Leu Lys
             50                  55                  60

His Glu Lys Pro Pro Gln
            65
```

```
<210> SEQ ID NO 28
<211> LENGTH: 222
<212> TYPE: PRT
<213> ORGANISM: Homo sapiens

<400> SEQUENCE: 28

Ala Thr Gln Lys Ser Val Val Ser Leu Asp Pro Pro Trp Ile Arg Ile
 1               5                  10                  15

Leu Thr Gly Asp Lys Val Thr Leu Ile Cys Asn Gly Asn Asn Ser Ser
                 20                  25                  30

Gln Met Asn Ser Thr Lys Trp Ile His Asn Asp Ser Ile Ser Asn Val
             35                  40                  45

Lys Ser Ser His Trp Val Ile Val Ser Ala Thr Ile Gln Asp Ser Gly
         50                  55                  60

Lys Tyr Ile Cys Gln Lys Gln Gly Phe Tyr Lys Ser Lys Pro Val Tyr
 65                  70                  75                  80

Leu Asn Val Met Gln Glu Trp Leu Leu Leu Gln Ser Ser Ala Asp Val
                 85                  90                  95

Val Leu Asp Asn Gly Ser Phe Asp Ile Arg Cys Arg Ser Trp Lys Lys
             100                 105                 110

Trp Lys Val His Lys Val Ile Tyr Tyr Lys Asp Asp Ile Ala Phe Lys
         115                 120                 125

Tyr Ser Tyr Asp Ser Asn Asn Ile Ser Ile Arg Lys Ala Thr Phe Asn
 130                 135                 140

Asp Ser Gly Ser Tyr His Cys Thr Gly Tyr Leu Asn Lys Val Glu Cys
 145                 150                 155                 160

Lys Ser Asp Lys Phe Ser Ile Ala Val Val Lys Asp Tyr Thr Ile Glu
                 165                 170                 175
```

-continued

```
Tyr Arg Trp Leu Gln Leu Ile Phe Pro Ser Leu Ala Val Ile Leu Phe
            180                 185                 190

Ala Val Asp Thr Gly Leu Trp Phe Ser Thr His Lys Gln Phe Glu Ser
            195                 200                 205

Ile Leu Lys Ile Gln Lys Thr Gly Lys Gly Lys Lys Lys Gly
            210                 215                 220

<210> SEQ ID NO 29
<211> LENGTH: 243
<212> TYPE: PRT
<213> ORGANISM: Homo sapiens

<400> SEQUENCE: 29

Met Asp Thr Glu Asn Lys Ser Arg Ala Asp Leu Ala Leu Pro Asn Pro
  1               5                  10                  15

Gln Glu Ser Pro Ser Ala Pro Asp Ile Glu Leu Leu Glu Ala Ser Pro
             20                  25                  30

Pro Ala Lys Ala Leu Pro Glu Lys Pro Ala Ser Pro Pro Pro Gln Gln
         35                  40                  45

Thr Trp Gln Ser Phe Leu Lys Lys Glu Leu Glu Phe Leu Gly Val Thr
     50                  55                  60

Gln Val Leu Val Gly Leu Ile Cys Leu Cys Phe Gly Thr Val Val Cys
 65                  70                  75                  80

Ser Thr Leu Gln Thr Ser Asp Phe Asp Glu Val Leu Leu Leu Tyr
                 85                  90                  95

Arg Ala Gly Tyr Pro Phe Trp Gly Ala Val Leu Phe Val Leu Ser Gly
                100                 105                 110

Phe Leu Ser Ile Met Ser Glu Arg Lys Asn Thr Leu Tyr Leu Val Arg
            115                 120                 125

Gly Ser Leu Gly Ala Asn Ile Val Ser Ser Ile Ala Ala Gly Leu Gly
        130                 135                 140

Ile Ala Ile Leu Ile Leu Asn Leu Ser Asn Asn Ser Ala Tyr Met Asn
145                 150                 155                 160

Tyr Cys Lys Asp Ile Thr Glu Asp Asp Gly Cys Phe Val Thr Ser Phe
                165                 170                 175

Ile Thr Glu Leu Val Leu Met Leu Leu Phe Leu Thr Ile Leu Ala Phe
            180                 185                 190

Cys Ser Ala Val Leu Leu Ile Ile Tyr Arg Ile Gly Gln Glu Phe Glu
        195                 200                 205

Arg Ser Lys Val Pro Asp Asp Arg Leu Tyr Glu Glu Leu His Val Tyr
    210                 215                 220

Ser Pro Ile Tyr Ser Ala Leu Glu Asp Thr Arg Glu Ala Ser Ala Pro
225                 230                 235                 240

Val Val Ser

<210> SEQ ID NO 30
<211> LENGTH: 62
<212> TYPE: PRT
<213> ORGANISM: Homo sapiens

<400> SEQUENCE: 30

Leu Gly Glu Pro Gln Leu Cys Tyr Ile Leu Asp Ala Ile Leu Phe Leu
  1               5                  10                  15

Tyr Gly Ile Val Leu Thr Leu Leu Tyr Cys Arg Leu Lys Ile Gln Val
             20                  25                  30
```

Arg Lys Ala Asp Ile Ala Ser Arg Glu Lys Ser Asp Ala Val Tyr Thr
        35                  40                  45

Gly Leu Asn Thr Arg Asn Gln Glu Thr Tyr Glu Thr Leu Lys
        50                  55                  60

<210> SEQ ID NO 31
<211> LENGTH: 11298
<212> TYPE: DNA
<213> ORGANISM: Homo sapiens

<400> SEQUENCE: 31

| | | | | |
|---|---|---|---|---|
| aagcttttca | aaggtgcaat | tggataactt | ctgccatgag | aaatggctga attgggacac | 60 |
| aagtggggac | aattccagaa | gaagggcaca | tctctttctt | ttctgcagtt ctttctcacc | 120 |
| ttctcaactc | ctactaaaat | gtctcatttt | caggttctgt | aaatcctgct agtctcaggc | 180 |
| aaaattatgc | tccaggagtc | tcaaattttc | ttatttcata | ttagtctttta tttagtagac | 240 |
| ttctcaattt | ttctattcat | cacaagtaaa | agcctgttga | tcttaatcag ccaagaaact | 300 |
| tatctgtctg | gcaaatgact | tatgtataaa | gagaatcatc | aatgtcatga ggtaacccat | 360 |
| ttcaactgcc | tattcagagc | atgcagtaag | aggaaatcca | ccaagtctca atataataat | 420 |
| attctttatt | cctggacagc | tcggttaatg | aaaaaatgga | cacagaaagt aataggagag | 480 |
| caaatcttgc | tctcccacag | gagccttcca | ggtaggtaca | aggtattatt ttttttctacc | 540 |
| ctcagtcact | tgtggcaggg | gaagtcatag | tcacggtgct | taggagatga aactttattg | 600 |
| atttaggcat | ggatccatct | agtttaatta | atatatttggg | tatgaggaag ctacttgctg | 660 |
| tactttccat | gtggttctct | ctccctggag | aggaacattt | ttactcagct tgcaaactgg | 720 |
| aaatagattt | tctcacatta | gaagctcatt | ttctgggtat | gagacaggag agttcatact | 780 |
| gtgtatgtag | atctctggct | tctgggtctg | acatgtgctg | agggacacat atccttcaca | 840 |
| catgctttta | taaatacttg | ataaagtaac | ctgcttcttg | attggtcttt ataatccata | 900 |
| agctgtggga | tgcttctctg | aagatgaaaa | tagtaataga | gtcccatcta gctattcaaa | 960 |
| gccattcctt | cattgtattc | tgtgcacatg | aagttggggt | ttgttactga caaaatatat | 1020 |
| tcagatacat | ttctatgtta | aaaggattgt | gagatgcata | ggtaaatgtg tttatttttca | 1080 |
| gttttacttg | tcaacataga | tgaatgagaa | agaacttgaa | agtaacactg gattaagaat | 1140 |
| aggaaaattt | ggcatggatt | ttgctccatt | ttgtcccatc | taatcacttg gatagtgttc | 1200 |
| aggtgttctt | ggtcagttac | ttggatgctc | tgagctttag | tttcttggtg attacaatga | 1260 |
| agatttgaat | tacaggatgg | ctttgaaaaa | ataaacaaaa | ctccccttttc tgtctgtcga | 1320 |
| gaatgttgca | cagggagtta | cagaatgttc | tcatgactga | attgcttttta aatttcacag | 1380 |
| tgtgcctgca | tttgaagtct | tggaaatatc | tccccaggaa | gtatcttcag gcagactatt | 1440 |
| gaagtcggcc | tcatcccac | cactgcatac | atggctgaca | gttttgaaaa aagagcagga | 1500 |
| gttcctgggg | gtgagtgagc | ctcctccaac | tttgactaga | gtaagggttg ggtctagaaa | 1560 |
| agaatattga | gttgcatcaa | ctgttttccc | acttggattc | atgagaggtg ttaggtcctt | 1620 |
| taaaaaacat | ggtagataaa | gagttgacac | taactgggtc | cttttgggaa gagccagaag | 1680 |
| catttcctca | taaagacttt | aaattgctag | gacgagaatg | gccaacagga gtgaaggatt | 1740 |
| cataacttta | tctttactta | gatgtaaaga | acaattactg | atgttcaaca tgactacata | 1800 |
| cataaaggcg | catggagaaa | agtattggcc | ttccatgcat | taggtagtgc ttgtatcaat | 1860 |
| tcttatagtg | gctagggtat | cctggaaaat | cttacgtgtg | gatcatttct caggacagtc | 1920 |
| taggacacta | acgcagtttc | tcatgtttgg | cttctattat | aaaaaatga tacaatctcg | 1980 |

-continued

```
ggaaaatttt tttgatttttc atgaaattca tgtgtttttc tataggtaac acaaattctg      2040
actgctatga tatgcctttg ttttggaaca gttgtctgct ctgtacttga tatttcacac      2100
attgagggag acattttttc atcatttaaa gcaggttatc cattctgggg agccatattt      2160
gtgagtatat atctataatt gtttctgaaa taacactgaa cataggtttt tctctttctc      2220
agatctaacc agttgtttat tcccagtatt aagatgatat ttataattct taattataaa      2280
tatatgtgag catatataac atagatatgc tcattaacaa caacaaaaga ttcttttttac     2340 aattaacggt gggttaaaca tttagcccac agttttatcc catgagaaac ctgaatctaa      2400
tacaagttaa atgacttgcc taagggccac ttgactaata gtaattgaac ctaaactttc      2460
agaatccaac tccaggaaca tacttctagc actattcatc aataaagtta tatgataaat      2520
acatacaact ttatctgtca actaaaaata acaacagagg ctgggcatgg tggctcacac      2580
ccgtaatccc agcactttgg gaggctgagg caggtggatc acctgaggtc aggagtttga      2640
gaccagcctg accaacatgg tgaaacctca tctctactaa atataaaaaa ttagctgagt      2700
gtgatagtgc atacctgtaa tccagctact aagaggctg aggcaggagg cttgtttgaa       2760
cctggaaggc agaggttgca gtgagctgag attgtgccat tgcactccag cctgggcaat      2820
aagtgcgaac tctgtctcaa ataataata ataataatag aaaataaagt tgtcttcatg       2880
aaaaatgagg aaagagattg ctggggtgag aaacattaag atcaatgggc atatggtgac      2940
cttctatgcc ctagaaactc ttttanggta ttttctcctg gtatctcttt tacncatcgt      3000
tctatctgga aaaataggtg gatgagtgag ataataacgg tatatacttt ttaaaggtct      3060
aattgacata tataaattgc aagtatttca gatgtcaatt tgctaacctt gacacacata     3120
gacacacatg aaaacatcac cacattaata caatgtatgt atccatcatt ccaaaagctt     3180
ccctgtgtat ctttgtaact cttcttcct ccctccactc cttgtcctct cgttcccaag       3240
aaaacattga tctgcttcct gtgaatataa attaacttac atttttaga gctttatata       3300 agtatgttct ctttactgtt tgtcttcctt cgctgcacag ttattttgag attcttcaag      3360
ttttttcttt atatcgatac ttcattcaca agaatatatt ttaattctag actatgtcac      3420
attgactttg tcgtctgcta aatccttagt gctcagatga cttgttcagg actctccttg     3480
aacctgtacc tctgttanat tgaaacttgt ctctactgtc ttttattc aaacacagct       3540 tattaggtgt ctctcaaccc atcaaacnca caatctgagt cttaggaga ttgctttgaa       3600 tttgtgctat tgacttatat ntatatnaaa tntgtaaatg tttggtaaaa atatcatcat      3660
gtacnttttc ataattacgc tatntncaca tgatatatgt cagactctgg aaatatgcat     3720
gccacagaca cgtgtttctt gcctaaaggg gctgatggaa gacncacata cnaatagacg     3780
attgcagtag aatgagagtg gtggtctaan cagtacatgt cctgatgttg ctcggacagt      3840
tactacncca agagtacccc ctgcattgtc agggttagca tctcctggaa gcctcatgta      3900
aatgaagaat tcatgctcc atccaggacc taatgaataa gaatctgcat tttagcaaga      3960
ccctcatatg attcatatac acttttttt tttttttta gatggagtct cactcttgtc       4020
gcccaggctg gagtgcaatg gcatgatctt ggctcactgc aacctctgcc tcccgggttc      4080
aagtgattct cctgtctcag cctccctagt agctgggact acaggtgcat gccacagtgg     4140
ctggctaatt tttgtatttt tagtagagac agggtttcac cattttggtc aggctggtct     4200
tgaactcatg acctccggtg attccccgc ctcggcttcc caaagtgctg ggattacaga      4260
catgagccac cacacccgcc ttattcgtat acncatttaa ttctgagaag cactctatag     4320
```

```
aaaataagaa taagaaaata ttgggctcac aggtgacatt aataagtaac tttatcgagt   4380 acccccaaatt ttacctatgt tggaagatg gggttaaaag gacacattga aaacaagaac   4440
tcattgtggc tttttttttcc tccttttttga acagttttct atttctggaa tgttgtcaat  4500
tatatctgaa aggagaaatg caacatatct ggtgagttgc ccgtttctgt ctttgtccat   4560
ccttgaaaag ataagaagaa cagagtttta agagtcttaa gggaaacaca tctttgtctc   4620
ctatattact tgtgaatgtg gatatatgat tttgtttcaa tctattttgt gtcctaaggc   4680
tttttgcaac agaagttgga tatatcatta gaaacataaa ttgtaccatt aacatacat   4740 gaagtttatg tttaccttga cgttcttcta aaaagtgtcc tacaccggca ttgtccttgt   4800
aggcatattc acatgatcaa ataaaataat tagttttcaa ttaaggagaa tatttgagga   4860
aagaccgtac gtgttcatgt ggttcctgaa ggcagtccag tgagaaagta atatatgctt   4920
cattaaacaa tgcggacatt ttcagggttt cccttttttaa ccaaaatttg gaagcaatgt   4980
ggaatttact ggatgcatcc agccctgaaa tgaagatagg tttattgaat gtgccagcaa   5040
gtgcaggccc aggtctgagt gttcttcatt attatcaggt gagaggaagc ctgggagcaa   5100
acactgccag cagcatagct gggggaacgg gaattaccat cctgatcatc aacctgaaga   5160
agagcttggc ctatatccac atccacagtt gccagaaatt ttttgagacc aagtgcttta   5220
tggcttcctt ttccactgta tgtattttttt tttgtgtggg aagactaaga ttctgggtcc   5280
taatgtaagt aagaagccct cttctcctgt tccatgaaca ccatccttttt ctgtaacttc   5340 tattacacag tatagtggtt ctgtaagttc acacagccca gggagatgct ggctgcccac   5400 tccctcaac ccaggcaaat tcctcggggt taaagttatc tactgcaagt gacgatctct   5460 gggttttttct gtgcctgtgt ttgtgtgtgt gtgtgtgtgt gtgtgtgtgt gtatgtgtca   5520 cttaaaagg actggtcaga tggtagggag atgaaaacag gagatgctat aagaaaataa   5580
acttttgggg cgaataccaa tgtgactctt tttgtttgtc atttgttgct gttcaatagg   5640
aaattgtagt gatgatgctg tttctcacca ttctgggact tggtagtgct gtgtcactca   5700
caatctgtgg agctggggaa gaactcaaag gaaacaaggt agatagaagc ccgatataaa   5760
atcttgaatg acaggttaac gaattggagc tttattcctt aaaatatggc ctgggttttc   5820
tgaaacattt cttccagaaa atagtttctc caagtttttat tactttggtt tacaaatctc   5880
acatttaaat cacattttat accataagta gcacacattt cataatattc ctctgaatga   5940
gggttgggat aataggactg atatgttaga aatgccttaa agtgtgtgga gcatgagaga   6000
tggatgtaca gaaggcttgt gaggaaacca cccaggtatc tggccttgtt ttctgcccca   6060
gaactagccg cctattcctg tttctgttttt attccttttgt ttcttgactt ttccttttcca   6120 acttgctcta aaacctcagt tttctttcct ttctgattca tgactaccaa atgttttcac   6180
ttgcctcacc cgtccattac acctttgata gaaccacca gaccttgtgc tcatgtactt   6240
gcccatgtct gatggaagaa acatactctc tccatctgtc cactttcctg aggcattcaa   6300
gtctagccac ctttttaaaat cactctcctc caggctgggc acggtgtcac gcctgtaatc   6360
tcagcacttt gtgaggctga ggagggcgga tcacttgaag tcaggagttc aaaaccagcc   6420
tggccaaatg gcaaaccaa atcttcttca attataacca aatcttaaac caaatctcta   6480
ctaaaaaata caacaaaaca aaacaacaac aacaaaaaca gaaaggaaa cattagccca   6540 gcgtggtggc aggtacctga ggttccagat acttgggagg ctgaagcagg agaatcgctt   6600
gagcccaaga gatggaggtt gcagtgagcc gagatcatgc cactgcacca cagccagggt   6660
gacagagcca tacttcccag cacattggga ggccaaagct gaagaataat ttgaggtgag   6720
```

```
gatttggaga ccagcctggc aacatggtg aaactccgtc tgtactaaaa atataaaact    6780
tagtggggca tggggcaca cacctgtaat ttcagctact taggaggctg aggcaggaga    6840
attgcttgaa cccgggaggc ggaagttgca gtgagccaag atcgtggcca ctgcactcca    6900
gcctgggtga catagtgaga ttctgtctca aaaaaaataa aagaaattta aaaaatcact    6960
ctcttccaaa gatagataaa taagacagca gatatactaa ggaataacct caccaacttg    7020
tcattgactg acatgatttc ttttggccca cttggccagc tagtctggtt tggttttctg    7080
gaaatgaaag aaataatcag agtttaatga cagagagcgt gagacccaga aagacaaaag    7140
tagatgaggt aagtctcttg agcgagactt ctagggatgg gaaatttgtg gtgattgata    7200
tgaaatgatt tttcccttat caggttccag aggatcgtgt ttatgaagaa ttaaacatat    7260
attcagctac ttacagtgag ttggaagacc caggggaaat gtctcctccc attgatttat    7320
aagaatcacg tgtccagaac actctgattc acagccaagg atccagaagg ccaaggtttt    7380 gttaagggc tactggaaaa atttctattc tctccacagc ctgctggttt tacattagat    7440
ttattcgcct gataagaata ttttgtttct gctgcttctg tccaccttaa tatgctcctt    7500
ctatttgtag atatgataga ctcctattttt tcttgtttta tattatgacc acacacatct    7560
ctgctggaaa gtcaacatgt agtaagcaag atttaactgt ttgattataa ctgtgcaaat    7620
acagaaaaaa agaaggctgg ctgaaagttg agttaaactt tgacagtttg ataatatttg    7680
gttcttaggg ttttttttt tttagcatt cttaatagtt acagttgggc atgatttgta    7740
ccatccaccc atacccacac agtcacagtc acacacacat atgtattact tacactatat    7800
ataacttcct atgcaaatat tttaccacca gtcaataata catttttgcc aagacatgaa    7860
gttttataaa gatctgtata attgcctgaa tcaccagcac attcactgac atgatattat    7920
ttgcagattg acaagtagga agtggggaac ttttattaag ttactcgttg tctggggagg    7980
taaataggtt aaaaacaggg aaattataag tgcagagatt aacatttcac aaatgtttag    8040
tgaaacattt gtgaaaaaag aagactaaat taagacctga gctgaaataa agtgacgtgg    8100
aaatggaaat aatggttata tctaaaacat gtagaaaaag agtaactggt agattttgtt    8160
aacaaattaa agaataaagt tagacaagca actggttgac taatacatta agcgtttgag    8220
tctaagatga aaggagaaca ctggttatgt tgatagaatg ataaaaaggg tcgggcgcgg    8280
aggctcacgc ctgtaatccc agccctttgg gaggccgagg tgggcagatc acgaagtcag    8340
tagtttgaga ccagcctggc caacatagtg aaaccccgtc tctactaaaa atacaaaaaa    8400
aaaattagct gggtgtggtg gcagtcacct gtagtcccag ctacttggga ggatgaggca    8460
ggagaatcgc ttgaacctgg gaggcggagg ttgcagtgag ccgagatcgc accagtgcac    8520
tccagccttg gtgacaatgg gagactccat ctcaaaaaaa aaaaaaaaa aaaaagata    8580 aaaagtcaga atctgaaaa gtggaggaag agtacaaata gacctaaatt aagtctcatt    8640
ttttggcttt gattttgggg agacaaaggg aaatgcagcc atagagggcc tgatgacatc    8700
caatacatga gttctggtaa agataaaatt tgatacacgg tttggtgtca ttataagaga    8760
aatcattatt aaatgaagca agttaacact ctaagagaat tattttgaga tagaagtgaa    8820
gctaagctaa acttcacatg cctataattg gagggaaaaa ctaaggataa aatctagcct    8880
agaagataca ataattagtc ataaacatgc attgtgaaac tgtagagagc aggtagccca    8940
aaatagagaa agattagata aagagaaaat aagtatccat cagagacagt atctctaggc    9000
ttgggcaaga gaaaagtcca cagtgataag caactccacc taaggcatga atatgcggca    9060
```

-continued

```
gagaaaacag caatagtgaa tgaatgcaaa aggtgctgag caaattccac acatgagtat    9120
tgtgcatgag taaatgaata aaacatttgc aaagaccttt agagaaagag aatgggagca    9180
tatgtgcgaa ataagatagt tgattatgaa tagaaggtag tgaagaaaag caagctaaga    9240
aaaaattctg tttataaaag aaggaaaaga tagtttatgt ttttagccta agtataagag    9300
tcctacagat ggactgaaaa aaatcagtct gagagtatta gtcacaatta atgaaataat    9360
tacattttat gtattgagga tgccaagatt aaaggtgac aggtagatgt taatttccct     9420
agattgtgaa agtgatcacg acaatcacac aacaaataat taagtgactt ggtatgcttt    9480
atttaattgt agggcctgag gttttccatt ctcattttc taaaatacaa ttttgtttct     9540
ccaaatttga cagcagaata aaacccctac cctttcactg tgtatcatgc taagctgcat    9600
ctctactctt gatcatctgt aggtattaat cacatcactt ccatggcatg atgttcaca    9660
tacagactct taaccctggt ttaccaggac ctctaggagt ggatccaatc tatatcttta    9720
cagttgtata gtatatgata tctcttttat ttcactcaat ttatattttc atcattgact    9780
acatatttct tatacacaac acacaattta tgaatttttt ctcaagatca ttctgagagt    9840
tgccccaccc tacctgcctt ttatagtacg cccacctcag gcagacacag agcacaatgc    9900
tggggttctc ttcacactat cactgcccca aattgtcttt ctaaatttca acttcaatgt    9960
catcttctcc atgaagacca ctgaatgaac acctttcat ccagccttaa tttcttgctc    10020
cataactact ctatcccacg atgcagtatt gtatcattaa ttattagtgt gcttgtgacc    10080
tccttatgta ttctcaatta cctgtatttg tgcaataaat tggaataatg taacttgatt    10140
tcttatctgt gtttgtgttg gcatgcaaga tttaggtact tatcaagata atggggaatt    10200
aaggcatcaa taaaatgatg ccaaagacca agagcagttt ctgaagtcct cctttcatc    10260
agctctttat caaacagaac actctataaa caacccatag ccagaaaaca ggatgtagga    10320
acaatcacca gcacactcta taacaaccc atagccagaa aacagaatgt aaggacaatc     10380
accagccatc ttttgtcaat aattgatgga atagagttga aaggaactgg agcatgagtc    10440
atatttgacc agtcagtcct cactcttatt tacttgctat gtaaacttga gaaagctttt    10500
ttctctttgt gaacctcagg ttttacatct gaaaatgaga aatttggaac aaaagattcc    10560
taactggtct ttctgttccc atattctgtg attttttcaat atttaggatt tttggtaatc    10620
acaattactt agtttgtggt tgagatagca acacgaatca gaactatttg gtggacatat    10680
tttcaaagga gtagctctcc actttgggta agaagtgat gcnggtcgtg gtggctcacg     10740
cctgtaatcc cagcacttta gggaggccaa ggcgggtgga tcacgaggtc aggagatcga    10800
gaccatcctg gctaacacgg tgaaaccccg tctctactaa aaatacaaa aaattagcca     10860
ggcgtggtgg cgggcgcctg tagtcccacg tactcgggag gctgaggcag gagaatggca    10920
tgaaccaggg aggcggagct tgccgtgagc cgagatagcg ccactgcagt ccctcctggg    10980
caaaagagca agactgcgtc tcaaaaaaaa aaaaaaaaa aaaaaagaa gtgtgtggag      11040
tagcaggaca cctgcaacaa taatattttt ctaaatccct ctgaaaaatg ctaatcaaag    11100
ggttttttc ctaaaaattg tcttagaaat aaaatttccc ctttgggaga ccgaggctgg    11160
cagatcacga ggtcaggaga tagagaccac ggtgaaaccc cgtctctact aaaaatacta    11220
aaaattagcc ggggngtggt ggtgggtaca cctgtagtcc cagctacttg gaggctgagg    11280
ctggagaatc acgtgaac                                                  11298
```

<210> SEQ ID NO 32
<211> LENGTH: 244

-continued

```
<212> TYPE: PRT
<213> ORGANISM: Homo sapiens

<400> SEQUENCE: 32

Met Asp Thr Glu Ser Asn Arg Arg Ala Asn Leu Ala Leu Pro Gln Glu
 1               5                  10                  15

Pro Ser Ser Val Pro Ala Phe Glu Val Leu Glu Ile Ser Pro Gln Glu
                20                  25                  30

Val Ser Ser Gly Arg Leu Leu Lys Ser Ala Ser Ser Pro Pro Leu His
            35                  40                  45

Thr Trp Leu Thr Val Leu Lys Lys Glu Gln Glu Phe Leu Gly Val Thr
        50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
                100                 105                 110

Met Leu Ser Ile Ile Ser Glu Arg Arg Asn Ala Thr Tyr Leu Val Arg
            115                 120                 125

Gly Ser Leu Gly Ala Asn Thr Ala Ser Ser Ile Ala Gly Gly Thr Gly
        130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Asp Arg Val Tyr Glu Glu Leu Asn Ile
    210                 215                 220

Tyr Ser Ala Thr Tyr Ser Glu Leu Glu Asp Pro Gly Glu Met Ser Pro
225                 230                 235                 240

Pro Ile Asp Leu

<210> SEQ ID NO 33
<211> LENGTH: 243
<212> TYPE: PRT
<213> ORGANISM: Rattus sp.

<400> SEQUENCE: 33

Met Asp Thr Glu Asn Lys Ser Arg Ala Asp Leu Ala Leu Pro Asn Pro
 1               5                  10                  15

Gln Glu Ser Pro Ser Ala Pro Asp Ile Glu Leu Leu Glu Ala Ser Pro
                20                  25                  30

Pro Ala Lys Ala Leu Pro Glu Lys Pro Ala Ser Pro Pro Gln Gln
            35                  40                  45

Thr Trp Gln Ser Phe Leu Lys Lys Glu Leu Glu Phe Leu Gly Val Thr
        50                  55                  60

Gln Val Leu Val Gly Leu Ile Cys Leu Cys Phe Gly Thr Val Val Cys
65                  70                  75                  80

Ser Thr Leu Gln Thr Ser Asp Phe Asp Asp Glu Val Leu Leu Leu Tyr
                85                  90                  95

Arg Ala Gly Tyr Pro Phe Trp Gly Ala Val Leu Phe Val Leu Ser Gly
```

```
                100                 105                 110
Phe Leu Ser Ile Met Ser Glu Arg Lys Asn Thr Leu Tyr Leu Val Arg
            115                 120                 125
Gly Ser Leu Gly Ala Asn Ile Val Ser Ser Ile Ala Ala Gly Leu Gly
        130                 135                 140
Ile Ala Ile Leu Ile Leu Asn Leu Ser Asn Asn Ser Ala Tyr Met Asn
145                 150                 155                 160
Tyr Cys Lys Asp Ile Thr Glu Asp Asp Gly Cys Phe Val Thr Ser Phe
                165                 170                 175
Ile Thr Glu Leu Val Leu Met Leu Leu Phe Leu Thr Ile Leu Ala Phe
            180                 185                 190
Cys Ser Ala Val Leu Leu Ile Ile Tyr Arg Ile Gly Gln Glu Phe Glu
        195                 200                 205
Arg Ser Lys Val Pro Asp Asp Arg Leu Tyr Glu Glu Leu His Val Tyr
    210                 215                 220
Ser Pro Ile Tyr Ser Ala Leu Glu Asp Thr Arg Glu Ala Ser Ala Pro
225                 230                 235                 240
Val Val Ser

<210> SEQ ID NO 34
<211> LENGTH: 235
<212> TYPE: PRT
<213> ORGANISM: Mus sp.

<400> SEQUENCE: 34

Met Asp Thr Glu Asn Arg Ser Arg Ala Asp Leu Ala Leu Pro Asn Pro
  1               5                  10                  15
Gln Glu Ser Ser Ser Ala Pro Asp Ile Glu Leu Leu Glu Ala Ser Pro
                 20                  25                  30
Ala Lys Ala Ala Pro Pro Lys Gln Thr Trp Arg Thr Phe Leu Lys Lys
             35                  40                  45
Glu Leu Glu Phe Leu Gly Ala Thr Gln Ile Leu Val Gly Leu Ile Cys
         50                  55                  60
Leu Cys Phe Gly Thr Ile Val Cys Ser Val Leu Tyr Val Ser Asp Phe
 65                  70                  75                  80
Asp Glu Glu Val Leu Leu Leu Tyr Lys Leu Gly Tyr Pro Phe Trp Gly
                 85                  90                  95
Ala Val Leu Phe Val Leu Ser Gly Phe Leu Ser Ile Ile Ser Glu Arg
                100                 105                 110
Lys Asn Thr Leu Tyr Leu Val Arg Gly Ser Leu Gly Ala Asn Ile Val
            115                 120                 125
Ser Ser Ile Ala Ala Gly Thr Gly Ile Ala Met Leu Ile Leu Asn Leu
        130                 135                 140
Thr Asn Asn Phe Ala Tyr Met Asn Asn Cys Lys Asn Val Thr Glu Asp
145                 150                 155                 160
Asp Gly Cys Phe Val Ala Ser Phe Thr Thr Glu Leu Val Leu Met Met
                165                 170                 175
Leu Phe Leu Thr Ile Leu Ala Phe Cys Ser Ala Val Leu Phe Thr Ile
            180                 185                 190
Tyr Arg Ile Gly Gln Glu Leu Glu Ser Lys Lys Val Pro Asp Asp Arg
        195                 200                 205
Leu Tyr Glu Glu Leu Asn Val Tyr Ser Pro Ile Tyr Ser Glu Leu Glu
    210                 215                 220
Asp Lys Gly Glu Thr Ser Ser Pro Val Asp Ser
```

<210> SEQ ID NO 35
<211> LENGTH: 4550
<212> TYPE: DNA
<213> ORGANISM: Homo sapiens
<220> FEATURE:
<221> NAME/KEY: misc_feature
<222> LOCATION: (578)
<223> OTHER INFORMATION: n represents a, c, t or g.
<220> FEATURE:
<221> NAME/KEY: misc_feature
<222> LOCATION: (735)
<223> OTHER INFORMATION: n represents a, c, t or g.
<220> FEATURE:
<221> NAME/KEY: misc_feature
<222> LOCATION: (1362)
<223> OTHER INFORMATION: n represents a , c, t or g
<220> FEATURE:
<221> NAME/KEY: misc_feature
<222> LOCATION: (2479)
<223> OTHER INFORMATION: n represents a, c, t or g.
<220> FEATURE:
<221> NAME/KEY: misc_feature
<222> LOCATION: (2517)
<223> OTHER INFORMATION: n represents a, c, t or g.
<220> FEATURE:
<221> NAME/KEY: misc_feature
<222> LOCATION: (2526)
<223> OTHER INFORMATION: n represents a, c, t or g.
<220> FEATURE:
<221> NAME/KEY: misc_feature
<222> LOCATION: (2549)..(2552)
<223> OTHER INFORMATION: n represents a, c, t or g.
<220> FEATURE:
<221> NAME/KEY: misc_feature
<222> LOCATION: (2612)..(2614)
<223> OTHER INFORMATION: n represents a, c, t or g.
<220> FEATURE:
<221> NAME/KEY: misc_feature
<222> LOCATION: (2633)
<223> OTHER INFORMATION: n represents a, c, t or g.
<220> FEATURE:
<221> NAME/KEY: misc_feature
<222> LOCATION: (2920)
<223> OTHER INFORMATION: n represents a, c, t or g.
<220> FEATURE:
<221> NAME/KEY: misc_feature
<222> LOCATION: (3069)
<223> OTHER INFORMATION: n represents a, c, t or g.

<400> SEQUENCE: 35

| | | | | | |
|---|---|---|---|---|---|
| tgatcaacat | ggagaaaccc | catctctact | aaaaatacaa | aattagctgg | gcgtggtggt | 60 |
| gcatgcctgt | aatgccagct | actcgggagg | ctgagagaat | cgcttgaacc | tgggaggcgg | 120 |
| aggttgcggt | gagccgagat | ggcgccattg | cactccagcc | tgggcaacaa | agcaagagtc | 180 |
| cgtctcaaaa | aaaaaaaaaa | aaaaaaaaat | ctgaaccagg | tggagtggaa | aatggcagat | 240 |
| gtagacagcc | tttcctgagc | gtgagagtct | cctcattctg | tgggttagga | gttggtcatt | 300 |
| gaagggctga | cgcttaagag | cccagatctc | ccaactccct | tagttggcct | tccgggagcc | 360 |
| gcccggtctc | ttgtgcagga | aggggaaggg | gccaaagcat | gggggaaggc | gtggcaggaa | 420 |
| gagggggact | ctgtggtcag | ggaactgctc | gctgagcaca | gctgcacagt | gctgtcagaa | 480 |
| cggccgatct | ccagcccaag | atgattccag | cagtggtctt | gctcttactc | cttttggttg | 540 |
| aacaagcagg | taagagggtt | tgtgagggat | agcgtgantg | gctccaggt | ggaagtccag | 600 |
| agcttgggtc | tgagggccaa | gtcaaacaca | ggtgaaggaa | ggctgacagt | gggtaggtgg | 660 |
| gcatagggag | accctgaggc | tagtcctctc | cagccccgac | ccaggcact | agactcatag | 720 |
| ttccctcctt | tcttnttgcc | ttcttacttc | attccagact | tttctccgta | ttattattat | 780 |

-continued

```
tattttggag atggagtctt gctctgtcac ccaggctgga gtgcagtggc gcaatctcta   840
ctcactgcaa cctctgcctc ctgggttcaa gcgattctcc tgcctcaggc tcccgagtag   900
ctgggactac aggtgcccgc caccacgccc ggctaagtta agtattttg gtagaaaccg    960 ggtttcgtca tgttaccag ggtagtcttg aactcctgac tcaagtgatc cacccacctc   1020
gacctcccaa agtgctggga ttactggtgt gagccactgc acccagctat tattattatt  1080
aaaaaaagac agggtcttac tatgttggcc acatccgtct tgaactcctg gcctcaagca  1140
attctcccac ctcggcctcc caaagtgcta ctgtgcctgg ctgacttttc tcttttcagg  1200
gttgatagaa agtggcaggg gaagggtctg gttgtatggc atgaagagct ggtctggtga  1260
aacgcctcat ttctcatgat gagcatttcc catggggtgc ctttggtctt gtctgctggg  1320
agctgatctc tagctggttt aatatacaaa gcacccttgg tnctataatt ccagctactc  1380
agaaggctga ggcaggagaa tcacttgaac ccaggaggtg gaggttgcag tgagccaaga  1440
tcgcaccact gcactctagc ctggggggaca gagtgagact ccgtctcaaa aaaaaaaaa   1500 agattttaca tatatatctc tatctatcta tctatataca cacacacaca catacacaca  1560
cacacacaca cacacacaca catatatata tatatataga gagagagaga gagagagaga  1620
gagagagaga tacccttag gaaggtagga ctctgttctt gtgcttggga gtaaggcaag   1680
gatatagcca agacaaacag atgggattgc tgtttctatg ggtcattgtt aatgctccat  1740
tctgtcagca gttgataatg agggtgggca gcatgagatc cccagttcca gagacctgag  1800
cgtcagctga gaaatagagg cagaaatggg aaggtctctg aagctctaca gctccagcca  1860
ctatctaaga attctcactc ctcgttcact ctgtgttgtc tgtgctggat tggtgtgtgt  1920
gtgttggtgg cagctgggtg ttggggagga ggaggtcagt aaacttcagg gaaactgtga  1980
aattgaaaga gaatgactgg ggaggaattc cagcagccta gctgagaagg tgggagcaag  2040
tattaagtta gccactggtc tgctgccgag ggatgaggag ggaggaggcc cgcagaggca  2100
caaaggaaag catgggcttt agaggcagaa aacctgcatt tgagttccag ctctgtcact  2160
taactctgtg gctctgagtg agttacttag cttttccgag ccttggtttc gtcacccata  2220
aaatggcgat gatgatgttt ccctcacagg gtagttttaa gatttgtgca atatcgtgtg  2280
tgtgaaagag tgttgcagaa taaaaagtac ttgaccgatg tcagcaattg actgacgtta  2340
gtcacatgtt ccctactggt cctctgatac ggggtgagag cagtctctgg agcccagact  2400
tgatttgatt ttttaaattg cacaaaactt cccctctcag agacccagag agtgagtaat  2460
agggcagagt aacaggagnt ggaatccata tagctgtggt cattccccca gccttgngtt  2520
cagggncaaa ggtatctgta aggtctggnn nnaacagaca cactttttt tttttttttt   2580 ttttttaca tatttaagtg tcttgtggtg gnnnagaaag caacaaggct ganctaggag   2640
atgaccaatg atagagtaat tgccttctct cccttcccca gctcacatcc ttcctgtcca   2700
gccctcagcc acaggtcaca ggacttagta gagacacttc tgtggtttct tcactgaaat   2760
ttgccactac ctctccctcc cactacccat cttggctgag gttttggttt cagtccagtg   2820
gactcagatg ggtcccttga ggtggataaa gtgctcaatg gtgcctgaag aacccacagt   2880
gctaaaaaga aaaggttggg ggctgagggg gaaggcctcn attattagtc cgtgtgagtc   2940
ccatttcaat agaaccctca agcttcctat cctagcctga ccctatggtg tgggaggagg   3000
gaaaggtaag ggcagtggaa ggccagagag aaacagaatt tcttcccctta gacggctccc   3060 ctccaggcnc tgtcctacct cccagagccc cttccctttct ctcctctgag taccagatcc   3120
```

-continued

```
tccctgatac ccccgacccc atgggcatcc tctatcccct cagcggccct gggagagcct    3180
cagctctgct atatcctgga tgccatcctg tttctgtatg gaattgtcct caccctcctc    3240
tactgtcgac tgaaggtagc gctgggcagg gtggggtaag ggctggaagg ggaagtggga    3300
ggagggcagc agcaaggatt cgaagagaag gaataaaagg ggatcctcca caaagtttgg    3360
agggaagggg gatgggccat taacttaccc tttactgata acctttcccc cattccagat    3420
ccaagtgcga aaggcagcta taaccagcta tgaggtatgg accctcctac acctggtgtg    3480
gacaactttt cagaccctca gccctcctgg ggctctagcc tggggtttcc gggcctctgg    3540
gagggctgcc tctcaggtgc tgatctgcat acacctcaga ggcctccctc ccaccttacc    3600
tagccaagcc acaagtaaaa tatcagcagg tgacagggaa gaatcaagca tagagtgata    3660
aagaatatgt gagagacttg gatgtagtat gtcgggtgta tatgtgtgct tgtagccatg    3720
tgggcaaaca ggtatcatgt cccagagtgt ccatgtgagt gccctctagc ccaaggtggc    3780
tggctgccca cccccatgc ctccctgggt ggggcagatg ctgagggcc ctggagaaag    3840
tgtgggtctt taatgttttg cttcttttgt ctctgcagaa atcagatggt gtttacacgg    3900
taagtgtgcc tacctccccc acccaggaag tcagcagaag agggtgggat tttgagcgat    3960
ctttggaagg ccggtggggg gaggggggtc ctgtggaggt gggagggggcc tctgatggac    4020
tccagctcct gatcgccctt tgactcccat ctccagggcc tgagcaccag gaaccaggag    4080
acttacgaga ctctgaagca tgagaaacca ccacagtagc tttagaatag atgcggtcat    4140
attcttcttt ggcttctggt tcttccagcc ctcatggttg gcatcacata tgcctgcatg    4200
ccattaacac cagctggccc taccctata atgatcctgt gtcctaaatt aatatacacc    4260
agtggttcct cctccctgtt aaagactaat gctcagatgc tgtttacgga tatttatatt    4320
ctagtctcac tctcttgtcc caccttctt ctcttcccca ttcccaactc cagctaaaat    4380
atgggaaggg agaaccccca ataaaactgc catggactgg actctattca ttcattcatt    4440
catttatcat agatttattc agtctctgct aagcactaga tacagctttt cagttccaga    4500
actcacagtc taatggactt cagagctatt ttgctcgact gagggataaa                4550
```